United States Patent [19]

Steinmeyer et al.

[11] Patent Number: 5,583,125
[45] Date of Patent: *Dec. 10, 1996

[54] 25-CARBOXYLIC ACID DERIVATIVES IN THE VITAMIN D SERIES, PROCESS FOR THEIR PRODUCTION, INTERMEDIATE PRODUCTS FOR THESE PROCESSES, PHARMACEUTICAL PREPARATIONS CONTAINING THESE DERIVATIVES AS WELL AS THEIR USE FOR THE PRODUCTION OF PHARMACEUTICAL AGENTS

[75] Inventors: Andreas Steinmeyer; Günter Neef; Gerald Kirsch; Katica Schwarz; Ruth Thieroff-Ekerdt; Herbert Wiesinger; Martin Haberey, all of Berlin, Germany

[73] Assignee: Schering Aktiengesellschaft, Berlin, Germany

[*] Notice: The term of this patent shall not extend beyond the expiration date of Pat. No. 5,446,035.

[21] Appl. No.: 132,176

[22] Filed: Oct. 6, 1993

[30] Foreign Application Priority Data

Oct. 6, 1992 [DE] Germany ............ 42 34 382.8
May 18, 1993 [DE] Germany ............ 43 17 415.9

[51] Int. Cl.$^6$ ................. C07C 401/00; A61K 31/59
[52] U.S. Cl. ............................. 514/167; 552/653
[58] Field of Search ....................... 552/653; 514/167

[56] References Cited

U.S. PATENT DOCUMENTS

| 4,022,891 | 5/1977 | Takeshita et al. ............ 424/236 |
| 5,446,035 | 8/1929 | Neef et al. ................. 514/167 |

FOREIGN PATENT DOCUMENTS

| 0421561 | 4/1991 | European Pat. Off. . |
| 87/00834 | 2/1987 | WIPO . |

Primary Examiner—Kimberly J. Prior
Attorney, Agent, or Firm—Millen, White, Zelano, & Branigan, P.C.

[57] ABSTRACT

New 25-carboxylic acid derivatives of general formula I,

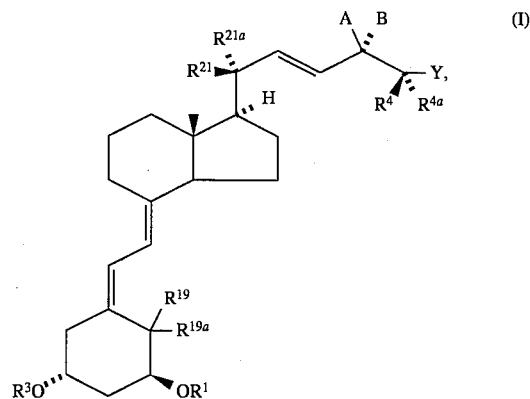

$R^{19}$ and $R^{19a}$ each mean a hydrogen atom or together form an exocyclic methylene group, $R^{21}$ and $R^{21a}$ independently of one another mean a hydrogen atom, a chlorine or fluorine atom, an alkyl group with 1 to 4 carbon atoms, together a methylene group, together with quaternary carbon atom 20 mean a 3–7 membered, saturated or unsaturated carboxylic ring, Y preferably means a derivatized carboxyl radical, and the other substituents have the meanings indicated in the description as well as process for their production, are described.

The new compounds have vitamin D activity as well as proliferation-inhibiting and cell-differentiating effects and are suitable for the production of pharmaceutical agents.

26 Claims, No Drawings

25-CARBOXYLIC ACID DERIVATIVES IN THE VITAMIN D SERIES, PROCESS FOR THEIR PRODUCTION, INTERMEDIATE PRODUCTS FOR THESE PROCESSES, PHARMACEUTICAL PREPARATIONS CONTAINING THESE DERIVATIVES AS WELL AS THEIR USE FOR THE PRODUCTION OF PHARMACEUTICAL AGENTS

This invention relates to 25-carboxylic acid derivatives of general formula I,

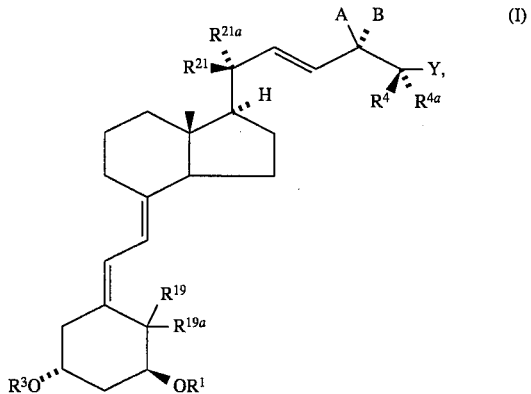

in which $R^1$ and $R^3$ independently of one another each mean a hydrogen atom, a straight-chain or branched-chain saturated alkanoyl group with 1 to 9 carbon atoms or an aroyl group, e.g., 6 to 10 carbon atoms, $R^{19}$ and $R^{19a}$ each mean a hydrogen atom or together an exocyclic methylene group, A and B together mean a keto oxygen atom or A means a group $OR^{24}$ and B a hydrogen atom, or A means a hydrogen atom and B a group $OR^{24}$ and $R^{24}$ is a hydrogen atom or a straight-chain or branched-chain saturated alkanoyl group with up to 9 carbon atoms or an aroyl group, $R^{21}$ and $R^{21a}$ independently of one another mean a hydrogen atom, a chlorine or fluorine atom, an alkyl group with 1 to 4 carbon atoms, together a methylene group, together with the carbon atom 20 mean a 3–7 membered, saturated or unsaturated carboxylic ring, $R^4$ and $R^{4a}$ simultaneously each mean a hydrogen atom, a chlorine or fluorine atom, a trifluoromethyl group, a straight-chain or branched-chain, saturated or unsaturated hydrocarbon radical with up to 4 carbon atoms or $R^4$ and $R^{4a}$ together with carbon atom 25 mean a 3 to 7 membered, saturated or unsaturated carboxylic ring, Y means one of the radicals $-C(O)-NR^5-R^{5'}$, $-C(O)OR^6$, $-C(O)SR^6$, or $-CN$, and $R^5$ and $R^{5'}$ independently of one another and $R^6$ each stand for a hydrogen atom or a linear or branched alkyl group with up to 8 carbon atoms and $R^6$ additionally stands for an unsaturated, linear or branched hydrocarbon dical with 3 to 8 carbon atoms or for the group

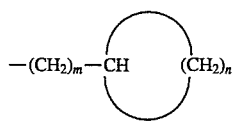

with m=0 or 1 and n=2, 3, 4, 5 or 6 and if m=1 additionally with n=1.

The invention also relates to a process for the production of compounds of formula I, intermediate products for this process, pharmaceutical preparations that contain these compounds as well as their use for the production of pharmaceutical agents.

Preferably, the radicals $R^1$, $R^3$ and $R^{24}$ each stand for a hydrogen atom.

The alkanoyl groups possible as radicals $R^1$, $R^3$ and $R^{24}$ are derived from saturated carboxylic acids, especially the acetic acid, propionic acid, butyric acid, isobutyric acid, pivalic acid or valeric acid.

The benzoyl radical is to be mentioned first as aroyl group.

Radicals $R^4$ and $R^{4a}$ preferably are methyl, ethyl, n-propyl, n-butyl, i-propyl, i-butyl and tert.butyl radicals. Also suitable for $R^4$ and $R^{4a}$ are the corresponding unsaturated hydrocarbon radicals containing double bond(s) and/or triple bond (s).

One of the $R^{21}$ and $R^{21a}$ radicals is preferably one of the meanings given immediately above for $R^4$ and $R^{4a}$ and the other of the $R^{21}$ and $R^{21a}$ radicals preferably is methyl.

Further, $R^{21}$ and $R^{21a}$ together preferably are a methylene group or they together with the carbon atom 20 form a cyclopropyl ring. Preferably, $R^{21}$ is a hydrogen atom and $R^{21a}$ is methyl; a 24-hydroxy group in the β-position is preferred as well in this case.

Further the following preferred substitution patterns are applicable:

$R^{21}$=F and $R^{21a}$=methyl; and $R^{21}$=methyl and $R^{21a}$=F.

$R^4$ and $R^{4a}$ each also preferably stand for a methyl or ethyl group or together with the carbon atom 25 form a cyclopropyl, cyclobutyl, cyclopentyl or cyclohexyl ring.

Alkyl groups for radicals $R^5$, $R^{5'}$ and/or $R^6$ are, for example, methyl, ethyl, n-propyl, n-butyl, i -propyl, i-butyl, tert.-butyl as well as higher straight-chain or branched chain alkyl groups.

Further, the following substituent combinations are preferred:

(a) if $R^{19}$ and $R^{19a}$ each stand for a hydrogen atom, then preferably $R^{21}$ is a hydrogen atom and $R^{21a}$ is a methyl group;

$R^{21}$ and $R^{21a}$ together are a methylene group;

$R^{21}$ and $R^{21a}$ are each a methyl group; or $R^{21}$ is a hydrogen atom and $R^{21a}$ is a fluorine atom or vice versa; and (b) if $R^{19}$ and $R^{21a}$ together stand for a methylene group, then preferably $R^{21}$ is a hydrogen atom and $R^{21a}$ is a methyl group;

$R^{21}$ and $R^{21a}$ together are a methylene group; or $R^{21}$ and $R^{21a}$ are each a methyl group.

The following compounds are especially preferred according to this invention:

(5Z,7E,22E) - (1S,3R,24R) -1,3,24-Trihydroxy-9,10-secocholesta-5,7,10 (19), 22-tetraene-25-carboxylic acid ethyl ester (5Z,7E,22E) - (1S,3R,24R) -26,27-Dimethyl-1,3,24-trihydroxy-9,10-secocholesta-5,7,10(19),22-tetraene-25-carboxylic acid methyl ester (5Z,7E,22E) - (1S,3R,24R) -1,3,24-Trihydroxy-9,10-secocholesta-5,7,10(19),22-tetraene-25-carboxylic acid-1-methyl ethyl ester (5Z,7E,22E) - (1S,3R,24R) -1,3,24-Trihydroxy-9,10-secocholesta-5,7,10(19),22-tetraene-25-carboxylic acid methyl ester (5Z,7E,22E) - (1S,3R,24S) -1,3,24-Trihydroxy-9,10-secochola-5,7,10(19),22-tetraene-24-acetic acid methyl ester (5Z,7E,22E) - (1S,3R,24R) -1,3,24-Trihydroxy-9,10-secocholesta-5,7,10(19),22-tetraene-25-carboxylic acid nitrile (5Z,7E,22E) - (1S,3R,24R) -1,3,24-Trihydroxy-9,10-secocholesta-5,7,10(19),22-tetraene-25-carboxylic acid propyl ester (5Z,7E,22E) - (1S,3R,24R) -1,3,24-Trihydroxy-9,10-secocholesta-5,7,10(19),22-tetraene-25-carboxylic acid (5Z,7E,22E) - (1S,3R,24R) -1,3,24-Trihydroxy-26,27-cyclo-9,10-secocholesta-5,7,10(19),22-tetraene-25-carboxylic acid methyl ester (5Z,7E,22E) - (1S,3R,24R) -1,3,24-Trihydroxy-26,27-cyclo-9,10-secocholesta-5,7,10(19),22-tetraene-25-carboxylic acid ethyl ester (5Z,7E,22E) - (1S,3R,24R) -1,3,24-Trihydroxy-26,27-cyclo-9,10-secocholesta-5,7,10(19),22-tetraene-25-carboxylic acid propyl ester (5Z,7E,22E) - (1S,3R,24R) -1,3,24-Trihydroxy-26,27-cyclo-9,10-secocholesta-5,7,10(19),22-tetraene-25-carboxylic acid butyl ester (5Z,7E,22E) - (1S,3R,24R) -1,3,24-Trihydroxy-26,27-cyclo-9,10-secocholesta-5,7,10(19),22-tetraene-25-carboxylic acid-2-methyl propyl ester (5Z,7E,22E) - (1S,3R,24R) -1,3,24-Trihydroxy-26,27-cyclo-9,10-secocholesta-5,7,10(19),22-tetraene-25-carboxylic acid pentyl ester (5Z,7E,22E) - (1S,3R,24R) -1,3,24-Trihydroxy-26,27-cyclo-9,10-secocholesta-5,7,10(19),22-tetraene-25-carboxylic acid hexyl ester (5Z,7E,22E) - (1S,3R,24R) -1,3,24-Trihydroxy-9,10-secocholesta-5,7,10(19),22-tetraene-25-carboxylic acid dimethyl amide (5Z,7E,22E) - (1S,3R,24R) -1,3,24-Trihydroxy-9,10-secocholesta-5,7,10(19),22-tetraene-25-carboxylic acid diethyl amide (5Z,7E,22E) - (1S,3R,24R) -1,3,24-Trihydroxy-26,27-cyclo-9,10-secocholesta-5,7,10(19),22 -tetraene-25 -carboxylic acid diethyl amide (5Z,7E,22E) - (1S,3R) -1,3-Dihydroxy-24-oxo-26,27-cyclo-9,10-secocholesta-5,7,10(19),22-tetraene-25-carboxylic acid-n-butylamide (5Z,7E,22E) - (1S,3R,24R) -20-Methyl-1,3,24-trihydroxy-9,10-secocholesta-5,7,10(19),22 -tetraene-25-carboxylic acid methyl ester (5Z,7E,22E) - (1S,3R,24S) -20-Methyl-1,3,24-trihydroxy-9,10-secocholesta-5,7,10(19),22-tetraene-25-carboxylic acid methyl ester (5Z,7E,22E) - (1S,3R,24R) -20-Methyl-1,3,24-trihydroxy-9,10-secocholesta-5,7,10(19),22-tetraene-25-carboxylic acid ethyl ester (5Z,7E,22E) - (1S,3R,24S) -20-Methyl-1,3,24-trihydroxy-9,10-secocholesta-5,7,10(19),22-tetraene-25-carboxylic acid ethyl ester (5Z,7E,22E) - (1S,3R,24R) -20-Methyl-1,3,24-trihydroxy-9,10-secocholesta-5,7,10(19),22-tetraene-25-carboxylic acid propyl ester (5Z,7E,22E) - (1S,3R,24S) -20-Methyl-1,3,24-trihydroxy-9,10-secocholesta-5,7,10(19),22-tetraene-25-carboxylic acid propyl ester (5Z,7E,22E) - (1S,3R,24R) -20-Methyl-1,3,24-trihydroxy-9,10-secocholesta-5,7,10(19),22-tetraene-25-carboxylic acid-1-methyl ethyl ester (5Z,7E,22E) - (1S,3R,24S) -20-Methyl-1,3,24-trihydroxy-9,10-secocholesta-5,7,10(19),22-tetraene-25-carboxylic acid-1-methyl ethyl ester (5Z,7E,22E) - (1S,3R,24R) -20-Methyl-1,3,24-trihydroxy-9,10-secocholesta-5,7,10(19),22-tetraene-25-carboxylic acid butyl ester (5Z,7E,22E) - (1S,3R,24S) -20-Methyl-1,3,24-trihydroxy-9,10-secocholesta-5,7,10(19),22-tetraene-25-carboxylic acid butyl ester (5Z,7E,22E) - (1S,3R,24R) -1,3,24-Trihydroxy-9,10-secocholesta-5,7,10(19),20,22-pentaene-25-carboxylic acid methyl ester (5Z,7E,22E) - (1S,3R,24S) -1,3,24-Trihydroxy-9,10-secocholesta-5,7,10(19),20,22-pentaene-25-carboxylic acid methyl ester (5Z,7E,22E) - (1S,3R,24R) -1,3,24-Trihydroxy-9,10-secocholesta-5,7,10(19),20,22-pentaene-25-carboxylic acid ethyl ester (5Z,7E,22E) - (1S,3R,24S) -1,3,24-Trihydroxy-9,10-secocholesta-5,7,10(19),20,22 -pentaene-25-carboxylic acid ethyl ester (5Z,7E,22E) - (1S,3R,24R) -1,3,24-Trihydroxy-9,10-secocholesta-5,7,10(19),20,22-pentaene-25-carboxylic acid propyl ester (5Z,7E,22E) - (1S,3R,24S) -1,3,24-Trihydroxy-9,10-secocholesta-5,7,10(19),20,22-pentaene-25-carboxylic acid propyl ester (5Z,7E,22E) - (1S,3R,24R) -1,3,24-Trihydroxy-9,10-secocholesta-5,7,10(19),20,22-pentaene-25-carboxylic acid-1-methyl ethyl ester (5Z,7E,22E) - (1S,3R,24S) -1,3,24-Trihydroxy-9,10secocholesta-5,7,10(19),20,22-pentaene-25-carboxylic acid-1-methyl ethyl ester (5Z,7E,22E) - (1S,3R,24R) -1,3,24-Trihydroxy-9,10-secocholesta-5,7,10(19),20,22-pentaene-25-carboxylic acid butyl ester (5Z,7E,22E) - (1S,3R,24S) -1,3,24-Trihydroxy-9,10-secocholesta-5,7,10(19),20,22-pentaene-25-carboxylic acid butyl ester (5Z,7E,22E) - (1S,3R,24R) -20,21-Methylene-1,3,24-trihydroxy-9,10-secocholesta-5,7,10(19),22-tetraene-25-carboxylic acid methyl ester (5Z,7E,22E) - (1S,3R,24S) -20,21-Methylene-1,3,24-trihydroxy-9,10-secocholesta-5,7,10(19),22-tetraene-25-carboxylic acid methyl ester (5Z,7E,22E) - (1S,3R,24R) -20,21 -Methylene-1,3,24-trihydroxy-9,10-secocholesta-5,7,10(19),22-tetraene-25-carboxylic acid ethyl ester (5Z,7E,22E) - (1S,3R,24S) -20,21-Methylene-1,3,24-trihydroxy-9,10-secocholesta-5,7,10(19),22-tetraene-25-carboxylic acid ethyl ester (5Z,7E,22E) - (1S,3R,24R) -20,21-Methylene-1,3,24-trihydroxy-9,10-secocholesta-5,7,10(19),22-tetraene-25-carboxylic acid propyl ester (5Z,7E,22E) - (1S,3R,24S) -20,21-Methylene-1,3,24-trihydroxy-9,10-secocholesta-5,7,10(19),22-tetraene-25-carboxylic acid propyl ester (5Z,7E,22E) - (1S,3R,24R) -20,21-Methylene-1,3,24-trihydroxy-9,10-secocholesta-5,7,10(19),22-tetraene-25-carboxylic acid-1-methyl ethyl ester (5Z,7E,22E) - (1S,3R,24S) -20,21-Methylene-1,3,24-trihydroxy-9,10 -secocholesta-5,7,10(19 ),22-tetraene-25-carboxylic acid-1-methyl ethyl ester (5Z,7E,22E) - (1S,3R,24R) -20,21-Methylene-1,3,24-trihydroxy-9,10-secocholesta-5,7,10(19 ),22- tetraene-25-carboxylic acid butyl ester (5Z,7E,22E) - (1S,3R,24S) -20,21-Methylene-1,3,24-trihydroxy-9,10-secocholesta-5,7,10(19),22-tetraene-25-carboxylic acid butyl ester (7E,22E) - (1R,3R,24R) -1,3,24-Trihydroxy-19-nor-9,10-secocholesta-5,7,22-triene-25-carboxylic acid methyl ester (7E,22E) - (1R,3R,24S) -1,3,24-Trihydroxy-19-nor-9,10-secocholesta-5,7,22-triene-25-carboxylic acid methyl ester (7E,22E) - (1R,3R,24R) -1,3,24-Trihydroxy-19-nor-9,10-secocholesta-5,7,22-triene-25-carboxylic acid ethyl ester (7E,22E) - (1R,3R,24S) -1,3,24-Trihydroxy-19 -nor- 9,10 -secocholesta-5,7,22 -triene-25 -carboxylic acid ethyl ester (7E,22E) - (1R,3R,24R) -1,3,24-Trihydroxy-19-nor-9,10-secocholesta-5,7,22-triene-25-carboxylic acid propyl ester (7E,22E) - (1R,3R,24S) -1,3,24-Trihydroxy-19-nor-9,10-secocholesta-5,7,22-triene-25-carboxylic acid propyl ester (7E,22E) - (1R,3R,24R) -1,3,24-Trihydroxy-19-nor-9,10-secocholesta-5,7,22-triene-25-carboxylic acid-1-methyl ethyl ester (7E,22E) - (1R,3R,24S) -1,3,24-Trihydroxy-19-nor-9,10-secocholesta-5,7,22-triene-25-carboxylic acid-1-methyl ethyl ester (7E,22E) - (1R,3R,24R) -1,3,24-Trihydroxy-19-nor-9,10-secocholesta-5,7,22-triene-25-carboxylic acid butyl ester (7E,22E) - (1R,3R,24S) -1,3,24-Trihydroxy-19-nor-9,10-secocholesta-5,7,22-triene-25-carboxylic acid butyl ester (7E,22E) - (1R,3R,24R) -1,3,24-Trihydroxy-19-nor-9,10-secocholesta-5,7,20,22-tetraene-25-carboxylic acid methyl ester (7E,22E) - (1R,3R,24 S) -1,3,24-Trihydroxy-19-nor-9,10-secocholesta-5,7,20,22-tetraene-25-carboxylic acid methyl ester (7E,22E) - (1R,3R,24R) -1,3,24-Trihydroxy-19-nor-9,10-secocholesta-5,7,20,22-tetraene-25-carboxylic acid ethyl ester (7E,22E) - (1R,3R,24S) -1,3,24-Trihydroxy-19-nor-9,10-secocholesta-5,7,20,22-tetraene-25-carboxylic acid ethyl ester (7E,22E) - (1R,3R,24R) -1,3,24-Trihydroxy-19-nor-9,10-secocholesta-5,7,20,22-tetraene-25-carboxylic acid propyl ester (7E,22E) - (1R,3R,24S) -1,3,24-Trihydroxy-19-nor-9,10-secocholesta-5,7,20,22-tetraene-25-carboxylic acid propyl ester (7E,22E) - (1R,3R,24R)-1,3,24-Trihydroxy-19-nor-9,10-secocholesta-5,7,20,22-tetraene-25-carboxylic acid-1-methyl ethyl ester (7E,22E) - (1R,3R,24S)-1,3,24-Trihydroxy-19-nor-9,10-secocholesta-5,7,20,22-tetraene-25-carboxylic acid-1-methyl ethyl ester (7E,22E)-(1R,3R,24R)-1,3,24-Trihydroxy-19-nor-9,10-secocholesta-5,7,20,22-tetraene-25-carboxylic acid butyl ester (7E,22E) - (1R,3R,24S)-1,3,24-Trihydroxy-19-nor-9,10-secocholesta-5,7,20,22-tetraene-25-carboxylic acid butyl ester (7E,22E) - (1R,3R)-1,3-Dihydroxy-24-oxo-19-nor-9,10-secocholesta-5,7,22-triene-25-carboxylic acid methyl ester (7E,22E) - (1R,3R)-1,3-Dihydroxy-24-oxo-19-nor-9,10-secocholesta-5,7,22-triene-25-carboxylic acid ethyl ester (7E,22E) - (1R,3R)-1,3-Dihydroxy-24-oxo-19-nor-9,10-secocholesta-5,7,22-triene-25-carboxylic acid propyl ester (7E,22E) - (1R,3R)-1,3-Dihydroxy-24-oxo-19-nor-9,10-secocholesta-5,7,22-triene-25-carboxylic acid-1-methyl ethyl ester (7E,22E) - (1R,3R)-1,3-Dihydroxy-24-oxo-19-nor-9,10-secocholesta-5,7,22-triene-25-carboxylic acid butyl ester (7E,22E) - (1R,3R)-1,3-Dihydroxy-24-oxo-19-nor-9,10-secocholesta-5,7,20,22-tetraene-25-carboxylic acid methyl ester (7E,22E) - (1R,3R)-1,3-Dihydroxy-24-oxo-19-nor-9,10-secocholesta-5,7,20,22-tetraene-25-carboxylic acid ethyl ester (7E,22E) - 1R,3R)-1,3-Dihydroxy-24-oxo-19-nor-9,10-secocholesta-5,7,20,22-tetraene-25-carboxylic acid propyl ester (7E,22E) - 1R,3R)-1,3-Dihydroxy-24-oxo-19-nor-9,10-secocholesta-5,7,20,22-tetraene-25-carboxylic acid-1-methyl ethyl ester (7E,22E) - (1R,3R)-1,3-Dihydroxy-24-oxo-19-nor-9,10-secocholesta-5,7,20,22-tetraene-25-carboxylic acid butyl ester (7E,22E) - (1R,3 R,20 S,24R) -20-Fluoro-1,3,24-trihydroxy-19-nor-9,10-secocholesta-5,7,22-triene-25-carboxylic acid ethyl ester (7E,22E) - (1R,3R,20S,24S) -20-Fluoro-1,3,24-trihydroxy-19-nor-9,10-secocholesta-5,7,22-triene-25-carboxylic acid ethyl ester (7E,22E) - (1R,3R,20R,24R) -20-Fluoro-1,3,24-trihydroxy-19-nor-9,10-secocholesta-5,7,22-triene-25-carboxylic acid ethyl ester (7E,22E) - (1R,3R,20R,24S) -20-Fluoro-1,3,24-trihydroxy-19-nor-9,10-secocholesta-5,7,22-triene-25-carboxylic acid ethyl ester (7E,22E) - (1R,3R,20S,24R) -20-Fluoro-1,3,24-trihydroxy-19-nor-9,10-secocholesta-5,7,22-triene-25-carboxylic acid-1-methyl ethyl ester (7E,22E) - (1R,3R,20S,24S) -20-Fluoro-1,3,24-trihydroxy-19-nor-9,10-secocholesta-5,7,22-triene-25-carboxylic acid-1-methyl ethyl ester (7E,22E) - (1R,3R,20R,24R) -20-Fluoro-1,3,24-trihydroxy-19-nor-9,10-secocholesta-5,7,22-triene-25-carboxylic acid-1-methyl ethyl ester (7E,22E) - (1R,3R,20R,24S) -20-Fluoro-1,3,24-trihydroxy-19-nor-9,10-secocholesta-5,7,22-triene-25-carboxylic acid-1-methyl ethyl ester (5Z,7E,22E) - (1S,3R,24R) -1,3,24-Trihydroxy-9,10-secocholesta-5,7,10(19),22-tetraene-25-carboxylic acid butyl ester (5Z,7E,22E) - (1S,3R,24S) -1,3,24-Trihydroxy-9,10-secocholesta-5,7,10(19),22-tetraene-25-carboxylic acid butyl ester (5Z,7E,22E) - (1S,3R,24R) -1,3,24-Trihydroxy-9,10-secocholesta-5,7,10(19),22-tetraene-25-carboxylic acid-2-methyl propyl ester (5Z,7E,22E) - (1S,3R,24S) -1,3,24-Trihydroxy-9,10-secocholesta-5,7,10(19),22-tetraene-25-carboxylic acid-2-methyl propyl ester (5Z,7E,22E) - (1S,3R,24R) -1,3,24-Trihydroxy-9,10-secocholesta-5,7,10(19),22-tetraene-25-carboxylic acid pentyl ester (5Z,7E,22E) - (1S,3R,24S) -1,3,24-Trihydroxy-9,10-secocholesta-5,7,10(19),22-tetraene-25-carboxylic acid pentyl ester (5Z,7E,22E) - (1S,3R) -1,3-Dihydroxy-24-oxo-9,10-secocholesta-5,7,10(19),22-tetraene-25-carboxylic acid methyl ester (5Z,7E,22E) - (1S,3R) -1,3-Dihydroxy-24-oxo-9,10-secocholesta-5,7,10(19),22-tetraene-25-carboxylic acid ethyl ester (5Z,7E,22E) - (1S,3R) -1,3-Dihydroxy-24-oxo-9,10-secocholesta-5,7,10(19),22-tetraene-25-carboxylic acid propyl ester (5Z,7E,22E) - (1S,3R) -1,3-Dihydroxy-24-oxo-9,10-secocholesta-5,7,10(19),22-tetraene-25-carboxylic acid-1-methyl ethyl ester (5Z,7E,22E) - (1S,3R) -1,3-Dihydroxy-24-oxo-9,10-secocholesta-5,7,10(19),22-tetraene-25-carboxylic acid butyl ester (5Z,7E,22E) - (1S,3R) -1,3-Dihydroxy-24-oxo-9,10-secocholesta-5,7,10(19),22-tetraene-25-carboxylic acid-2-methyl propyl ester (5Z,7E,22E) - (1S,3R) -1,3-Dihydroxy-24-oxo-9,10-secocholesta-5,7,10(19),22-tetraene-25-carboxylic acid pentyl ester (5Z,7E,22E) - (1S,3R) -1,3-Dihydroxy-20-methyl-24-oxo-9,10-secocholesta-5,7,10(19),22-tetraene-25-carboxylic acid ethyl ester (5Z,7E,22E) - (1S,3R) -1,3-Dihydroxy-20-methyl-24-oxo-9,10-secocholesta-5,7,10(19),22-tetraene-25-carboxylic acid-1-methyl ethyl ester (5Z,7E,22E) - (1S,3R,24R) -1,3,24-Trihydroxy-26a,27-cyclo-26a-homo-9,10-secocholesta-5,7,10(19),22-tetraene-25-carboxylic acid ethyl ester (5Z,7E,22E) - (1S,3R,24S) -1,3,24-Trihydroxy-26a,27-cyclo-26a-homo-9,10-secocholesta-5,7,10(19),22-tetraene-25carboxylic acid ethyl ester (5Z,7E,22E) - (1S,3R,24R) -1,3,24-Trihydroxy-26a,27-cyclo-26a-homo-9,10-secocholesta-5,7,10(19),22-tetraene-25-carboxylic acid-1-methyl ethyl ester (5Z,7E,22E) - (1S,3R,24S) -1,3,24-Trihydroxy-26a,27-cyclo-26a-homo-9,10-secocholesta-5,7,10(19),22-tetraene-25-carboxylic acid-1-methyl ethyl ester.

The natural vitamins $D_2$ and $D_3$ (cf. general formula of vit. D) are biologically inactive per se and are converted only after hydroxylation in 25-position in the liver or in 1-position in the kidney to the latter's biologically active metabolites. The action of vitamins $D_2$ and $D_3$ consists in the stabilization of the plasma-$Ca^{++}$ and plasma-phosphate level; they counteract a decline of the plasma-$Ca^{++}$ level.

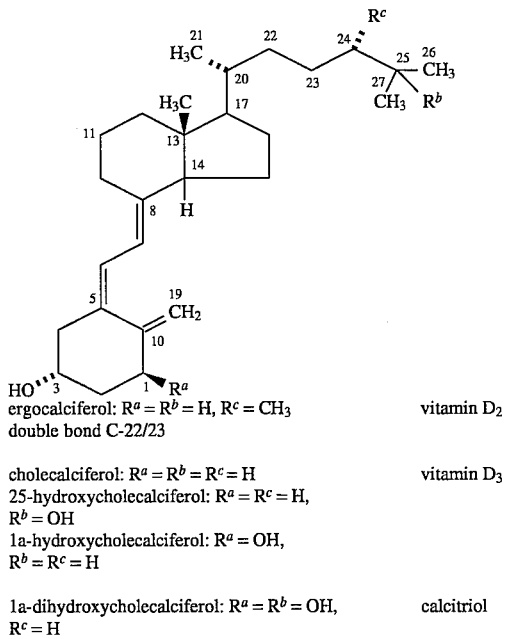

ergocalciferol: $R^a = R^b = H$, $R^c = CH_3$    vitamin $D_2$
double bond C-22/23 cholecalciferol: $R^a = R^b = R^c = H$    vitamin $D_3$
25-hydroxycholecalciferol: $R^a = R^c = H$, $R^b = OH$
1α-hydroxycholecalciferol: $R^a = OH$, $R^b = R^c = H$ 1α-dihydroxycholecalciferol: $R^a = R^b = OH$, $R^c = H$    calcitriol In addition to their pronounced effect on the calcium and phosphate metabolism, vitamins $D_2$ and $D_3$ and their synthetic derivatives also have proliferation-inhibiting and cell-differentiating effects (H. F. De Luca, The Metabolism and Function of Vitamin D in Biochemistry of Steroid Hormones, Editors H. L. J. Makin, 2nd Edition, Blackwell Scientific Publications 1984, pp. 71–116).

But, overdosage symptoms (hypercalcemia) can occur with use of vitamin D.

1α-Cholecalciferols hydroxylated in 24-position can be seen already from DE-A-25 26 981; they have a lower toxicity than the corresponding non-hydroxylated 1α-cholecalciferol. The hydroxylated compounds show a selective activation of the intestinal calcium absorption and a weaker bone absorption effect than 1α-cholecalciferol.

The 24-hydroxy vitamin D analogs described in international patent application WO 87/00834 can be used for the treatment of disorders in humans and animals caused by abnormal cell proliferation and/or cell differentiation.

For various 1,25-dihydroxy-homo-vitamin D derivatives, a dissociation relative to the properties of bone absorption effect and HL-60 cell differentiation have already been mentioned recently by De Luca. The bone absorption effect in vitro is in this case a direct measurement for the calcium mobilization in vivo.

Finally, 24-cycloalkylmethyl-substituted vitamin D derivatives are described in EP-A 0 421 561 that have a more favorable spectrum of activity than calcitriol. While their effects on the calcium and phosphate metabolism are markedly weakened in comparison with calcitriol, the proliferation- inhibiting and cell-differentiating effects are approximately retained.

In comparison with these structurally allied compounds, the 25-carboxylic acid derivatives according to the invention in the vitamin D series stand out in that they are even more strongly dissociated with respect to the cell differentiation in comparison to the hypercalcemic effect.

The vitamin D activity of the compounds according to the invention is determined by the calcitriol receptor test. It is performed with use of a specific receptor protein from the intestine of young pigs.

Receptor-containing binding protein is incubated in a test tube with $^3$H-calcitriol ($5\times10^{-10}$ mol/l) in a reaction volume of 0.270 ml in the absence and in the presence of test substances for two hours at 4° C. To separate free and receptor-bound calcitriol, a charcoal-dextran absorption is performed. For this purpose, 250 µl of a charcoal-dextran suspension is fed to each test tube and incubated at for 20 minutes. Then, the samples are centrifuged at 10,000×g for 5 minutes at 4° C. The supernatant is decanted and measured in a β-counter after 1 hour of equilibration in Picofluor 15 TM.

The competition curves obtained with various concentrations of the test substance as well as of the reference substance (unlabeled calcitriol) at a constant concentration of the reference substance ($^3$H-calcitriol) are placed in relation to one another and a competition factor (KF) is determined.

It is defined as a quotient of the concentrations of the respective test substance and the reference substance, which are necessary for 50% competition:

KF=Concentration of the test substance at 50% competition

Concentration of the reference substance at 50% competition

The compounds according to the invention have in common that all have at their disposal a considerable affinity for the calcitriol receptor.

To determine the acute hypercalcemic effect of various calcitriol derivatives, the test described below is performed:

The action of control (solvent base), reference substance (1.25 $(OH)_2$—$D_3$=calcitriol) and test substance is tested respectively after one-time subcutaneous administration in groups of 10 native male rats (140–170 g). During the testing time, the rats are kept in special cages to determine the excretion of water and mineral substances. The urine is collected in 2 fractions (0–16 hours and 16–22 hours). An oral calcium load (0.1 mmol of calcium in 6.5% α-hydroxypropyl cellulose, 5 ml/animal) replaces the calcium absorption lacking by food deprivation at 16 hours. At the end of the test, the animals are killed by decapitation and exsanguinated to determine the serum-calcium values. For the primary screen test in vivo, a single standard dose (200 µg/kg) is tested. For selected substances, the result is checked by drawing up a dose-effect correlation.

A hypercalcemic effect become apparent in serum-calcium level values elevated in comparison to the control.

The significance of differences between substance groups and controls as well as between test substance and reference substance is checked by suitable statistical methods. The result is indicated as dose ratio DR (DR=factor test substance dose/reference substance dose for comparable effects).

The differentiation-stimulating effect of calcitriol analogs is also detected quantitatively.

It is known in the literature (Mangelsdorf, D. J. et al., J. Cell. Biol. 98: 391–398 (1984)) that the treatment of human leukemia cells (promyelocyte cell line HL 60) in vitro with calcitriol induces the differentiation of cells to macrophages.

HL 60 cells are cultivated in tissue culture medium (RPMI-10% fetal calf serum) at 37° C. in an atmosphere of 5% $CO_2$ in air.

For substance testing, the cells are centrifuged off and $2.0 \times 10^5$ cells/ml are taken up in phenol-red-free tissue culture medium. The test substances are dissolved in ethanol and diluted with tissue culture medium without phenol red to the desired concentration. The dilution stages are mixed with the cell suspension in a ratio of 1:10 and 100 µl each of this cell suspension mixed with substance is pipetted in an indentation of a 96-hole plate. For the control, a cell suspension is mixed analogously with the solvent.

After incubation over 96 hours at 37° C. in 5% $CO_2$ in air, 100 µl of an NBT-TPA solution (nitrosoblue tetrazolium (NBT), end concentration in the batch of 1 mg/ml, tetradecanoyl phorbolmyristat-13-acetate (TPA), end concentration in the batch of $2 \times 10^{-7}$ mol/l) is pipetted in each indentation of the 96-hole plate to the cell suspension.

By incubation over 2 hours at 37° C. and 5% $CO_2$ in air, NBT is reduced to insoluble formazan because of the intracellular oxygen radical release, stimulated by TPA, in the cells differentiated to macrophages.

To end the reaction, the indentations of the 96-hole plate are suctioned off and the adhering cells are fixed by adding methanol and dried after fixing. To dissolve the formed intracellular formazan crystals, 100 µl of potassium hydroxide (2 val/l) and 100 µl of dimethyl sulfoxide are pipetted in each indentation and ultrasonically irradiated for 1 minute. The concentration of formazan is spectrophotometrically measured at 650 nm.

The concentration of formed formazan is considered a measurement for the differentiation induction of the HL 60 cells to macrophages. The result is also indicated as dose ratio (DR=factor test substance dose/reference substance dose for comparable effects).

The results of the calcitriol receptor test as well as the determination of the dose ratio of the differentiation induction of HL 60 cells and the dose ratio for hypercalcemia are summarized below: Test compounds:

(5Z,7E,22E)-(1S,3R,24R)-1,3,24-Trihydroxy-9,10-secocholesta-5,7,10(19),22-tetraene-25-carboxylic acid ethyl ester 10a (5Z,7E,22E) - (1S,3R,24R) -1,3,24-Trihydroxy-9,10-secocholesta-5,7,10(19),22-tetraene-25-carboxylic acid-1-methyl ethyl ester 13a (5Z,7E,22E) - (1S,3R,24R) -1,3,24-Trihydroxy-9,10-secocholesta-5,7,10(19),22-tetraene-25-carboxylic acid propyl ester 19a (5Z,7E,22E) - (1S,3R,24R) -1,3,24-Trihydroxy-9,10-secocholesta-5,7,10(19),22 -tetraene-25-carboxylic acid dimethyl amide 31a (5Z,7E,22E) - (1S,3R,24R) -20-Methyl-1,3,24-Trihydroxy-9,10-secocholesta-5,7,10(19),22-tetraene-25-carboxylic acid ethyl ester 46a (5Z,7E,22E) - (1S,3R,24R) -20-Methyl-I, 3,24-Trihydroxy-9,10-secocholesta-5,7,10(19 ),22-tetraene-25-carboxylic acid propyl ester 48a (5Z,7E,22E) - (1S,3R,24S) -20-Methyl-1,3,24-Trihydroxy-9,10-secocholesta-5,7,10(19),22-tetraene-25-carboxylic acid propyl ester 48b (5Z,7E,22E) - (1S,3R,24R) -20-Methyl-1,3,24-Trihydroxy-9,10-secocholesta-5,7,10(19),22-tetraene-25-carboxylic acid-1-methyl ethyl ester 50a (5Z,7E,22E) - (1S,3R,24R) -1,3,24-Trihydroxy-9,10-secocholesta-5,7,10(19),20,22-pentaene-25-carboxylic acid-1methyl ethyl ester 64a (7E,22E) - (1R,3R,20R,24S) -20-Fluoro-1,3,24-trihydroxy-19-nor-9,10-secocholesta-5,7,22-triene-25-carboxylic acid ethyl ester 111

(5Z,7E,22E) - (1S,3R) -1,3-Dihydroxy-24-oxo-9,10-secocholesta-5,7,10(19),22-tetraene-25-carboxylic acid methyl ethyl ester (5Z,7E,22E) - (1S,3R,24R) -1,3,24-Trihydroxy-9,10-secocholesta-5,7,10(19),22-tetraene-25-carboxylic acid 21a (5Z,7E,22E) - (1S,3R,24R) -1,3,24-Trihydroxy-26,27-cyclo-9,10-secocholesta-5,7,10(19),22-tetraene-25-carboxylic acid methyl ester 22a (5Z,7E,22E) - (1S,3R,24R) -1,3,24-Trihydroxy-26,27-cyclo-9,10-secocholesta-5,7,10(19 ),22-tetraene-25-carboxylic acid ethyl ester 23a (5Z,7E,22E) - (1S,3R,24R) -1,3,24-Trihydroxy-26,27-cyclo-9,10-secocholesta-5,7,10(19 ),22-tetraene-25-carboxylic acid propyl ester 24a (5Z,7E,22E) - (1S,3R,24R) -1,3,24-Trihydroxy-26,27-cyclo-9,10-secocholesta-5,7,10(19 ),22-tetraene-25-carboxylic acid butyl ester 25a (5Z,7E,22E) - (1S,3R,24R) -1,3,24-Trihydroxy-26,27-cyclo-9,10-secocholesta-5,7,10(19),22-tetraene-25-carboxylic acid-2-methyl propyl ester 26a

| | Comparison compound: calcitriol | | |
|---|---|---|---|
| Compound | Competition factor KF for receptor binding | Dose relation for HL 60 cells | Dose relation for hypercalcemia |
| 6a | 4.1 | 1.3 | 100 |
| 10a | 2.4 | 0.6 | 100 |
| 13a | 2.1 | 0.3 | 1500 |
| 19a | 1.8 | 0.2 | 100 |
| 31a | 2.6 | 0.8 | 100 |
| 46a | 4.1 | 1.3 | 100 |
| 48a | 2.8 | 0.2 | >100 |
| 48b | 16 | 1 | 100 |
| 50a | 2.4 | 0.6 | >100 |
| 64a | 2.7 | 2 | >>100 |
| 111 | 11 | 4 | >100 |
| 125 | 3.6 | 2 | 100 |
| 21a | 32 | >1000 | 1000 |
| Calcitriol | 1 | 1 | 1 |

In addition to an affinity for the calcitriol receptor, like calcitriol the listed compounds also show partially stronger agonistic activities in vitro (HL 60 operational test). However, the induction of a hypercalcemia in vivo takes place first at markedly higher doses than in calcitriol.

However, free carboxylic acid 21a, which could be a potential metabolite of the test compounds, binds markedly poorer to the receptor and is practically inactive in vitro and in vivo. By the reduced hypercalcemia risk, the substances according to the invention are suitable in a special way for the production of pharmaceutical agents for the treatment of diseases, which are characterized by a hyperproliferation, e.g. hyperproliferative diseases of the skin (psoriasis) and malignant tumors (leukemia, colon cancer, breast cancer) and acne (J. Invest. Dermatol., Vol. 92 No. 3, 1989). The compounds according to the invention can also be used for treatment and prophylaxis of disorders, which are characterized by a disequilibrium of the immune system, for example, auto-immune diseases, including diabetes mellitus and the rejection reactions in transplantations (WO-A-91/00855). In an especially preferred embodiment of the invention, calcitriol receptors are detected in the target organ before the treatment.

Further, it has been found, surprisingly, that by topical administration of the compounds according to the invention on the skin of mice, rats and guinea pigs, an increased reddening of the skin and increase of epidermal thickness can be induced. The increase of the reddening of the skin is determined based on the increase of the red value of the skin surface quantifiable with a colorimeter. The red value is typically increased 1.5-fold after the substance has been administered three times (dose 0.003%) at intervals of 24 hours. The increase of the epidermal thickness is quantified in the histological preparation. It is increased 2.5-fold. The number of proliferating epidermal cells (cells in the S-phase of the cell cycle) is determined flow-cytometrically and is typically increased.

These properties of the 25-carboxylic acid derivatives in the vitamin D series according to the invention make them appear suitable for therapeutic use in the case of atrophic skin, as it occurs with natural skin ageing, premature skin ageing because of increased exposure to light or medicinally induced skin atrophy by treatment with glucocorticoids.

Further, it is to be assumed that the healing of wounds can be accelerated with the new compounds by topical administration.

The compounds according to the invention of general formula I are also potent inhibitors of the proliferation and interleukin (IL 2) synthesis of human lymphocytes.

Because of the inhibition of the lymphocyte proliferation and IL-2 synthesis in low concentrations the compounds of general formula I according to the invention are suitable for treatment of diseases of the immune system, e.g., diseases of the atopic morphology (atopic dermatitis, asthma), auto-immune diseases including diabetes mellitus, rejection reactions in transplantations and AIDS. It was found that calcitriol, because of its receptor imparted mechanisms, not only inhibits the IL-2 secretion but also the production of other inflammation promoting cytokines. Since the compounds of general formula I, for example, also bind just as well to the receptor as calcitriol they are suitable for the treatment of inflammatory diseases such as arthritis, colitis ulcerosa and Crohn's disease.

In the treatment of auto-immune diseases, rejection reactions in transplantations and AIDS the new compounds of general formula I can be advantageously combined with other immunosuppressive effective substances such as cyclosporin A and FK 506.

It was also found that certain compounds of general formula I in HL 60 cells surprisingly antagonize the effect of calcitriol. In the 26,27-cyclo series ($R^4+R^{4a}$+C20=cyclopropyl) the carboxylic acid esters with an increasing chain length of $R^6$ in radical Y show markedly weaker vitamin D activity in vitro and in vivo with unchanged good receptor affinity. The transition from agonism to antagonism lies between the propyl and butyl ester 24a and 25a. Thus, 25a binds with the same affinity as calcitriol to its receptor, but has no differentiation stimulation effect in HL 60 cells. This characteristic, to antagonize calcitriol in HL 60 cells, continues with increased chain length in radical $R^6$.

With simultaneous incubation of calcitriol with increasing concentrations of the compound to be tested for antagonism in HL 60 cells an inhibition of the NBT reduction induced by calcitriol is found as a measure for the differentiation-stimulating effect of calcitriol that, for example, is complete at 100 times the excess of compound 25a. The same also applies to compound 26a and the higher carboxylic acid esters.

Some test results, that show the decreased agonistic effect with an increasing chain length of $R^6$, are listed below:

| Compound | Competition factor KF for receptor binding | Dose relation for HL 60 cells | Dose relation for hypercalcemia |
|---|---|---|---|
| Calcitriol | 1 | 1 | 1 |
| 22a | 4.0 | 2.2 | >100 |
| 23a | 2.8 | 2.9 | >>100 |
| 24a | 4.6 | 22 | >>100 |
| 25a | 1.0 | >1000 | >1000 |
| 26a | 2.5 | >1000 | 1000 |

Compounds, that antagonize the effect of calcitriol, can be used in the treatment of hypercalcemias, such as, e.g., in hypervitaminosis D or intoxication with calcitriol as well as substances acting like calcitriol or in increased extrarenal calcitriol synthesis occurring in granulomatous diseases (e.g., sarcoidosis). Paraneoplastic hypercalcemia (e.g. in osteolytic bone metastases) and hypercalcemia in hyperparathyroidism can be treated with a calcitriol antagonist.

Further calcitriol antagonists can be used for birth control. The vitamin D receptor is expressed in the reproduction tract of female and male animals. It is known that the female and male fertility of vitamin D deficient animals is reduced. The reproduction performance can be increased by brief substitution of calcitriol. Therefore calcitriol antagonists are able to influence female and male fertility.

Since calcitriol shows an immunosuppressive effect under certain conditions, calcitriol receptor antagonists are also used as immunostimulants, e.g., in lowered resistance to infection.

It is known that calcitriol can modulate hair growth. Therefore, therapeutic use can be found for calcitriol antagonists in unwanted hair growth, e.g., in hirsutism.

This invention thus relates also to the pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For a topical application, the compounds are advantageously formulated as creams or ointments or in a similar form of pharmaceutical agents suitable for topical application. Each such formulation can also contain other pharmaceutically compatible and non-toxic auxiliary agents, such as, e.g., stabilizers, antioxidants, binders, dyes, emulsifiers or flavoring substances. The compounds are advantageously administered by injection or intravenous infusion of suitable sterile solutions or as oral dosage by the alimentary tract or topically in the form of creams, ointments, lotions or suitable transdermal plasters, as described in EP-A 0 387 077.

The daily dose is preferably about 0.1 µg/patient/day–1000 µg (1 mg)/patient/day, especially 1.0 µg/patient/day–500 µg/patient/day.

The compounds according to the invention are generally administered analogously to the administration of %he known agent "calcipotriol" for treatment of psoriasis.

The invention further relates to the use of compounds according to formula I for the production of pharmaceutical agents.

The production of the 25-carboxylic acid derivatives of general formula I takes place according to the invention characterized in that a compound of general formula II

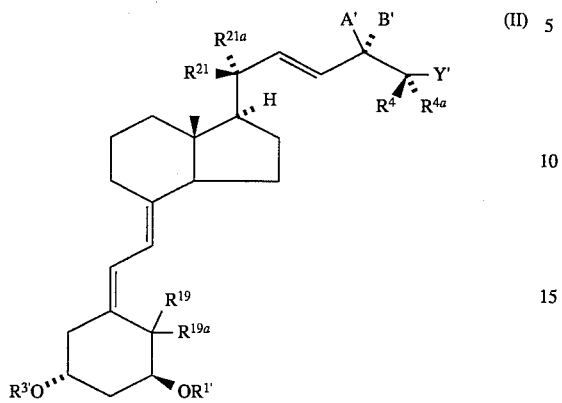

in which $R^{1'}$ and $R^{3'}$ mean alkyl (e.g., 1–10 C atoms), aryl (e.g., 6–10 C atoms) or mixed alkyl and aryl substituted silyl groups, preferably the tert.-butyldimethylsilyl, tert.-butyldiphenylsilyl or triisopropylsilyl group, A' and B' together mean a keto group or one of the two substituents represents an optionally protected hydroxy group and the other a hydrogen atom (silyl protective group of the above definition, tetrahydrofuranyl, tetrahydropyranyl, methoxymethyl, methoxyethoxymethyl or trimethylsilylethoxymethyl group), $R^{19}$, $R^{19a}$, $R^{21}$, $R^{21a}$, $R^4$ and $R^{4a}$ which have the meanings already described in general formula I, and Y' has the same radicals as Y in the compound of general formula I or, if Y in the compound of formula I is to be —C(O)OR$^6$ and R$^6$ is to be hydrogen, optionally means a 2-(trimethylsilyl)ethyl-carboxylic acid ester group, is converted into a compound of general formula I by simultaneous or successive cleavage of the hydroxy and optionally carboxylic acid protective groups and optionally by partial, successive or complete esterification of free hydroxy groups and/or if Y' then stands for a carboxyl radical —COOH, optionally by its esterification or conversion into an amide radical —C(O)NR$^5$R$^{5a}$.

In the case of silyl protective groups or trimethylsilylethoxymethyl group, tetrabutylammoniumfluoride, hydrofluoric acid or hydrofluoric acid/pyridine can be used for their cleavage; in the case of the remaining ether groups they can be separated under the catalytic action of acid, for example, p-toluene sulfonic acid, pyridinium-p-toluene sulfonate, acetic acid, hydrochloric acid or an acid ion exchanger.

If R$^6$ in general formula I should mean hydrogen, Y' in general formula II preferably stands for a 2-(trimethylsilyl)ethyl carboxylic acid ester group, whose cleavage takes place with one of the mentioned fluorine reagents. The resulting free carboxylic acid can optionally be further reacted according to standard processes by esterification or conversion to an amide radical —C(O)NR$^5$R$^{5'}$ or a thioester —C(O)SR$^6$.

The production of the initial compounds for general formula II starts from various starting compounds depending on the finally desired substitution pattern in 10 and 20 position.

To obtain the compounds of general formula II, in which $R^{19}$ and $R^{19a}$ together stand for an exo-position methylene group, a start is made from (20S)-formylsecopregnatrienes of general formula III

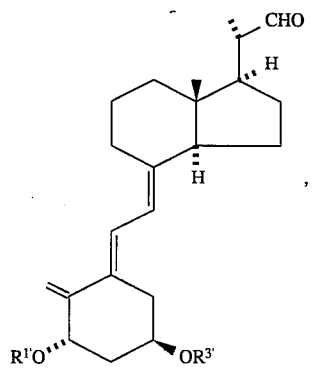

described in Tetrahedron 43, 4609 (1987) or in international patent application WO 87/00834 of M. Calverley et al., in which $R^{1'}$ and $R^{3'}$ have the already described meanings.

Protective groups in III other than those described in the indicated places, can be obtained by an analogous procedure using correspondingly modified silyl chlorides (e.g. tert-butyldiphenylsilyl chloride instead of tert.butyldimethylsilyl chloride).

If the compounds of general formula II in the 20 position, necessary for the production of the finally desired compounds of general formula I, should have a substitution pattern different from calcitriol, the compounds of general formula III are converted according to a new process into the C20 modified analogs of general formula IV

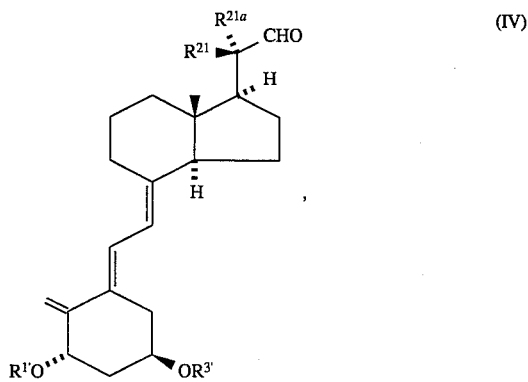

in which $R^1$, $R^3$, $R^{21}$ and $R^{21a}$ have the meanings already described.

For synthesis of the compounds of general formula V

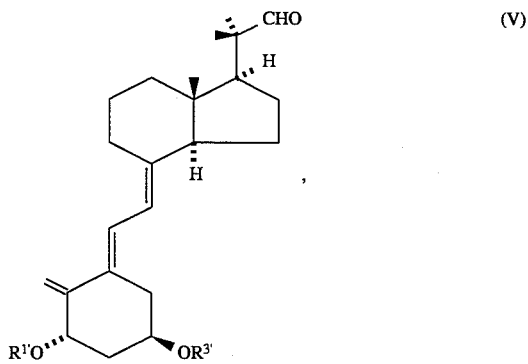

that is derived from general formula IV in that $R^{21}$ and $R^{21a}$ each represent a methyl group, the compound of general formula III is deprotonated with a base such as sodium hydride, potassium hydride, lithium diisopropylamide or potassium-tert.-butanolate and reacted with an electrophilic reagent providing the methyl group, such as, for example, $CH_3X$ (X=Cl, Br, I, tosylate, mesylate).

The homologous alkyl groups $R^{21}$ and $R^{21a}$ are introduced analogously by alkylation with a reagent providing the homologous alkyl group.

The introduction of a chlorine or fluorine atom in 20 position is possible by α-halogenation according to a standard process.

If finally $R^{21}$ is to stand for a hydrogen atom and $R^{21a}$ for a methyl group for synthesis of the side chain now either, a compound of general formula III or a compound of general formula IV (or V) is reacted in a Wittig reaction with N-methoxy-N-methyl-2-(triphenylphosphoranylidene)-acetamide (D. A. Evans et al. J. Am. Chem. Soc. 112, 7001 (1990)) or, another, analogously reacting phosphoranylidene at a higher temperature to a compound of general formula VI

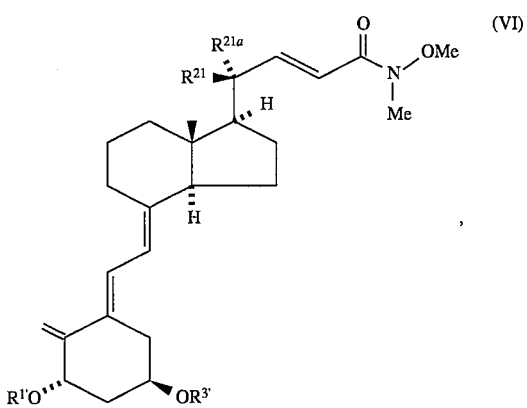

in which $R^{1'}$, $R^{3'}$, $R^{21}$ and $R^{21a}$ have the indicated meaning.

The reaction occurs preferably at a temperature of 90°–120° C. in a solvent such as, e.g., dimethylsulfoxide (DMSO) or toluene.

In the next reaction step the amino radical —$N(CH_3)(OCH_3)$ is expelled by treatment of the compound of general formula VI with a reducing agent such as diisobutyl aluminum hydride (DIBAH) or lithium aluminum hydride in a solvent such as tetrahydrofuran or another ether at a lower temperature (–60° to –100° C.) and the homologous aldehyde of general formula VII

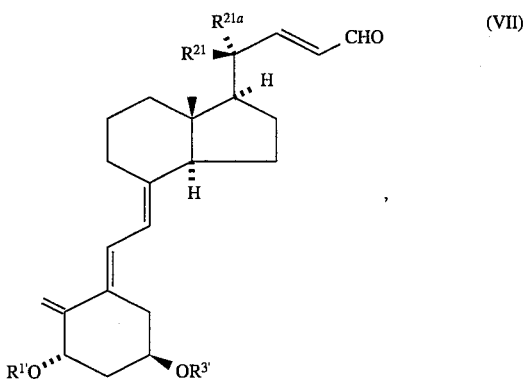

is obtained.

Thus, if $R^{21}$=H and $R^{21a}$=$CH_3$, compounds already known from WO-A-91/00855 are involved.

By addition of a suitable nucleophilic component to the carbonyl function of aldehyde VII, the side chain can now be formed, as it is to be present in the finally desired 25-carboxylic acid derivative of general formula I. But if $R^4$ and $R^{4a}$ together with carbon atom 25 should form a cyclopropyl ring, a synthesis route described infra is taken.

With the action of a strong base, such as, e.g., lithium diisopropyl amide, lithium diethyl amide, lithium-, sodium- or potassium-hexamethyldisilacide, first a compound of general formula VIII

in which $R^{4'}$ and $R^{4a'}$ have the meaning already described for $R^4$ and $R^{4a}$ in general formula II and Y' has the meaning already described in general formula II, with the exception that $R^{4'}$ and $R^{4a'}$ together with the central carbon atom cannot stand for a cyclopropyl ring, is deprotonated in a solvent with tetrahydrofuran or another ether at a temperature between –60° and –90° C. and then added to a compound of general formula VII and a compound of general formula IX

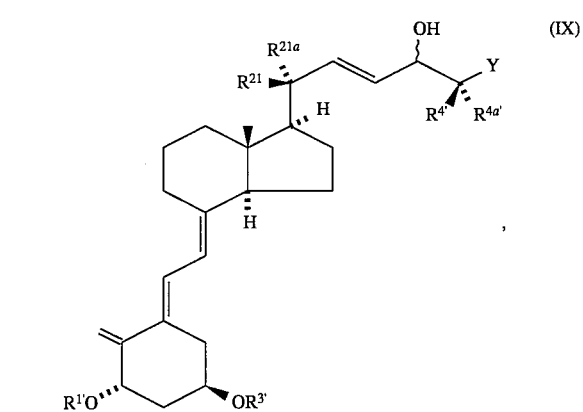

in which $R^{1'}$, $R^{3'}$, $R^{4'}$, $R^{4a'}$ and Y' have the meanings already indicated, is obtained.

Both the 24α and the 24β-hydroxy isomers that can be separated chromatographically in this or in a later stage are obtained in this way. In the following reactions therefore, the separated diastereomers or the mixture can be used as desired.

In the case where $R^{21}$=H and $R^{21a}$=$CH_3$, and $R^{19}$ and $R^{19a}$ together stand for a methylene group (so-called "standard series"), the 24β-hydroxy compounds of general formula I relative to the 24α-hydroxy compounds as a rule are distinguished by a greater affinity for the calcitriol receptor (lower receptor values KF).

If A and B in the finally desired compound of general formula I together are to mean a keto oxygen atom, the 24-hydroxy compound of general formula IX is oxidized in this or a later stage with manganese dioxide, pyridinium chlorochromate, pyridinium dichromate, barium manganate or oxalyl chloride/dimethylsulfoxide to a the 24-keto compound.

The conversion of a compound of general formula IX into the corresponding compound of general formula II takes place, e.g., by irradiation with ultraviolet light in the presence of a so-called "triplet sensitizer." Within the scope of this invention, anthracene is used for this purpose. By cleavage of the π-bond of the 5,6-double bond, rotation of the A-ring by 180° around the 5,6-single bond and reestablishing the 5,6-double bond, the stereoisomerism of the 5,6-double bond is reversed. Then, if present, the 24-hydroxy group is optionally provided with a protective group (tetrahydrofuranyl, tetrahydropyranyl, methoxymethyl, methoxyethoxymethyl or trimethylsilylethoxymethyl group) under the usual conditions familiar to one skilled in the art. This procedure makes possible a clean cleavage of silyl protective groups $R^{1'}$ and $R^{3'}$ especially if $R^{1'}$ and $R^{3'}$ each stand for a tert.-butyldiphenylsilyl protective group. Finally, if present, the 24-hydroxy protective group in the last stage is again removed by the catalytic action of an acid agent (pyridinium-p-toluene sulfonate [PPTS], p-toluene sulfonic acid, acetic acid, hydrochloric acid, acid ion-exchanger) and the free hydroxy groups are optionally reacted further as already described.

If a tert.-butyldimethylsilyl or triisopropylsilyl group each stand for $R^{1'}$ and $R^{3'}$, the cleavage of the protective groups can be performed directly, i.e., without temporary protection of the 24-hydroxy group, with acid ion exchangers (p-toluene sulfonic acid, acetic acid, hydrochloric acid or pyridinium p-toluene sulfonate) or by the effect of tetrabutylammoniumfluoride (trihydrate) or hydrogen fluoride or hydrogen fluoride/pyridine complex at temperatures below 30° C.

If in the final desired active compounds of general formula I, $R^4$ and $R^{4a}$ together with carbon atom 25 form a 3 or 4 membered cycloalkyl radical, another way for the production of the necessary compounds of general formula II must be taken (in the case of cyclopropyl) or can be taken (in the case of cyclobutyl).

As starting compound, a compound of general formula III is again used on whose carbonyl group a C-H acidic compound of general formula XXVIII (D. F. Taber et al., J. Org. Chem. (1992) 57, 436) is added to a side-chain lengthening under the action of a strong base such as, for example, lithium diisopropylamide

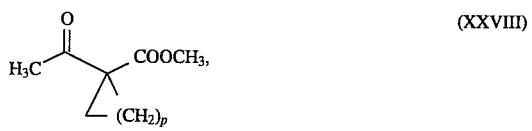

in which
p stands for the index 1 or 2.
In this way with cleavage of the ester the free 25-carboxylic acid of general formula XXIX

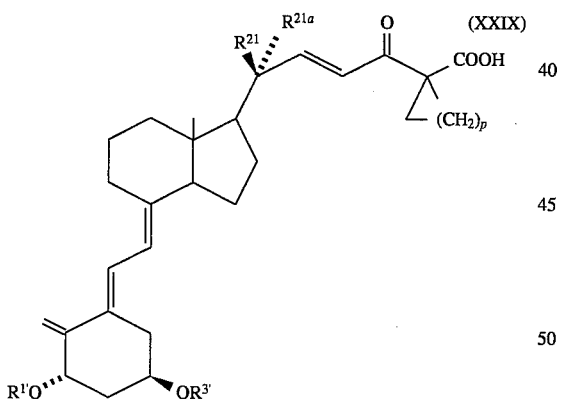

is formed
in which $R^{1'}$ and $R^{3'}$ and p have the above-mentioned meanings.

Finally if Y is not to be an unsubstituted carboxyl group, the next reaction step is its derivatization.

The carboxyl group can be activated under mild conditions at −20° to −30° C. (Synth. Commun. 12, 727–731 (1982)) by reaction of a compound of general formula IX with methanesulfonyl chloride and triethylamine and treatment of the intermediarily formed mixed anhydride with an alcohol of general formula XXX

in which $R^6$ has the same meaning as $R^6$ in formula I, into the corresponding ester of general formula XXXI

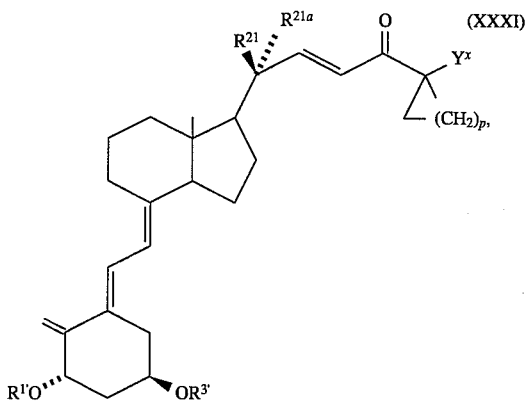

in which
$R^{1'}$ and $R^{3'}$ and p have the already indicated meaning and $Y^x$ stands for a carbon ester group —C(O)OR$^6$ with the already indicated meanings for $R^6$.

The carboxylic acid of general formula XXIX can also be converted according to known processes into a compound analogous to the compound of general formula XXXI in which $Y^x$ then stands for an amide group —C(O)NR$^5$R$^{5a}$ or a cyano radical.

Then the 24-keto group is reduced with sodium borohydride to the 24-hydroxy group. In this way, as in the nucleophilic addition of a compound of general formula VI to an aldehyde of general formula IV, both possible 24-hydroxy isomers of general formula XXXII

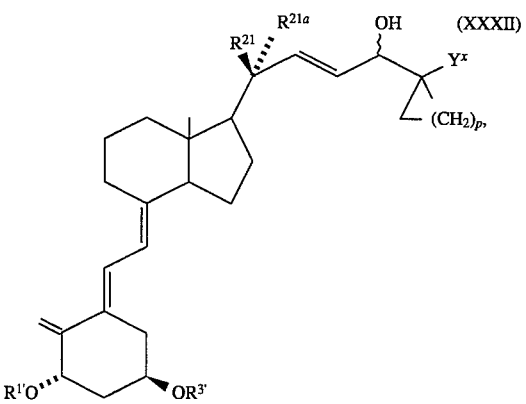

are also obtained
in which means a 24α or 24β-hydroxy group and the other substituents as well as p have the already indicated meanings.

With respect to the separation of the isomers and their further reaction, what has been said with respect to the compounds of general formula IX also applies here.

Quite analogously to the irridation of a compound of general formula IX for conversion into a compound of general formula II, a compound of general formula XXXII (or a mixture of the corresponding 24-hydroxy isomers) is now being converted into the corresponding compound of general formula II.

For production of the desired end compounds of general formula I existing hydroxy protective groups are then cleaved off, and optionally, the free hydroxy groups according to standard processes are partially, successively or completely esterified with the corresponding carboxylic acid halide (halide=chloride, bromide) or carboxylic acid anhydride.

If Y in the compound of general formula I represents a free carboxyl group, the latter can also be esterified in the end stage according to standard processes with a reagent providing the radical —$OR^6$.

The cleavage of the protective groups of the free hydroxy groups is generally possible by treatment of the corresponding compound of general formula II with tetrabutylammoniumfluoride (trihydrate) in a polar solvent such as, for example, tetrahydrofuran, optionally with addition of a small amount of glacial acetic acid. A possibly present 2-(trimethylsilyl)ethyl radical for the protection of the 25-carboxylic acid is co-cleaved off.

The hydroxy protective groups, even if $R^4$, $R^{4a}$ and carbon atom 25 together form a cyclopropyl ring, can also be cleaved by treatment of the corresponding compound of general formula II with an acid ion exchanger such as, for example, "Dowex 50WX8" in a solvent such as methanol/methylene chloride.

But a partial, successive or complete but varying substitution of the free hydroxy groups can be achieved by keeping in mind their varying reactivities and by using corresponding molar amounts of esterification reagent.

For establishing of another C-20 modification ($R^{21}+R^{21a}=$ methylene) a compound of general formula X

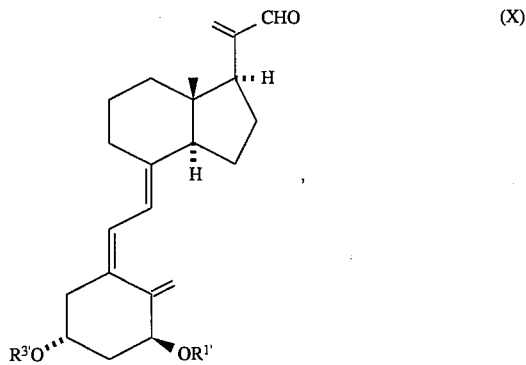

in which $R^{1'}$ and $R^{3'}$ have the already indicated meanings, is produced, that is derived from general formula IV in that $R^{21}$ and $R^{21a}$ together form a methylene group and the isomerization of the triene system has already taken place.

In this connection a compound of general formula III, analogously to the process described in WO-90/09991 (in this case $R^{1'}$ and $R^{3'}$ are preferably tert.butyldiphenylsilyl groups), is converted into a compound of general formula XI

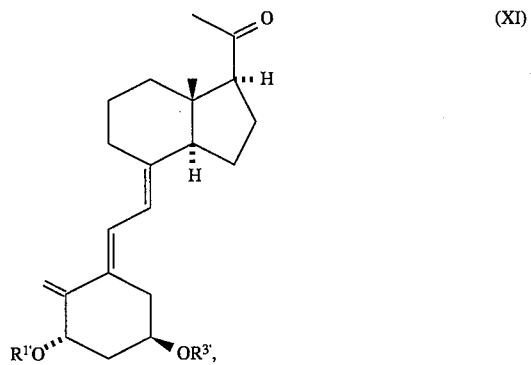

in which $R^{1'}$ and $R^{3'}$ have the already indicated meanings.

By reaction of such a 17β-acetyl compound of general formula XI with sulfur ylides, which are produced from reagents of the type $Me_3S^+I^-$ or $Me_3S^+(O)I^-$ by deprotonization with a base such as potassium tert.-butanolate, sodium hydride or potassium hydride, a compound of general formula XII

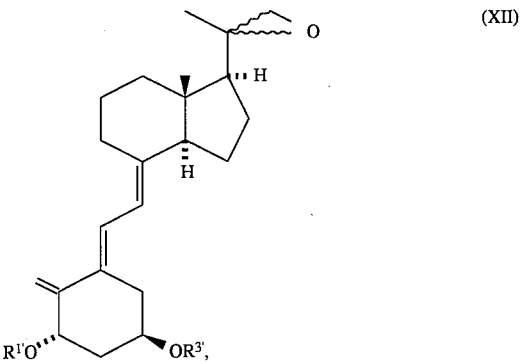

is obtained in which $R^{1'}$ and $R^{3'}$ have the known meaning and in which the stereochemistry on C-20 must not be uniform.

By rearranging the epoxides of general formula XII with bases, such as, e.g., lithium diisopropyl amide, lithium diethyl amide or aluminum isopropylate the allyl alcohols of general formula XIII are obtained

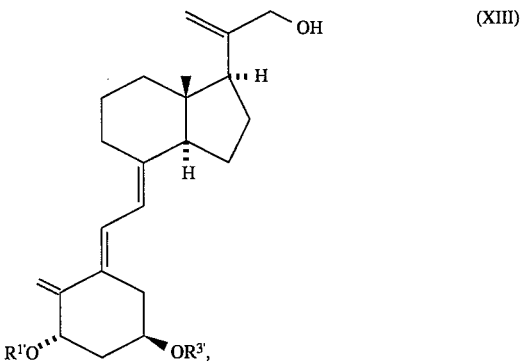

in which $R^{1'}$ and $R^{3'}$ have the known meaning, which analogously to what has already been described are converted by photochemical isomerization of the triene system into a compound of general formula XIV

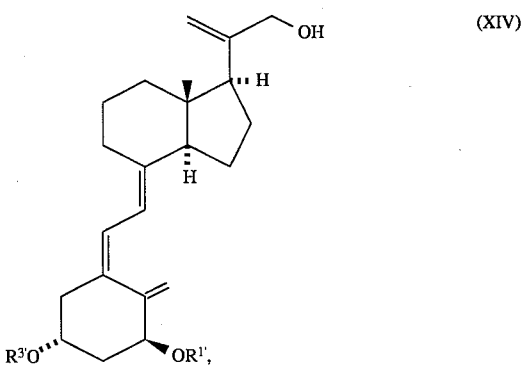

in which $R^{1'}$ and $R^{3'}$ have the known meaning.

Their conversion into a compound of general formula X takes place now by oxidation with an oxidizing agent, such as, e.g., manganese dioxide, pyridinium chlorochromate, pyridinium dichromate, barium manganate or oxalyl chloride/DMSO according to known methods.

Another C-20 modification ($R^{21}+R^{21a}+C20$=cyclopropyl) is introduced by reaction of a compound of general formula XIV with an organometallic reagent of type I—$CH_2$—Zn—I, that is formed from Zn/Cu, Zn/Ag or $Et_2Zn$ with $CH_2I_2$ (Simmons-Smith reaction) and a compound of general formula XV

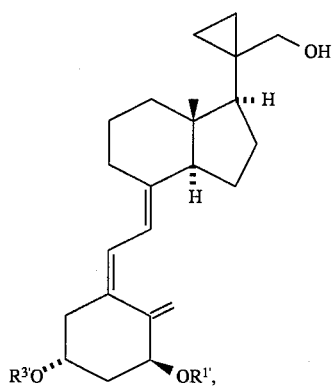
(XV)

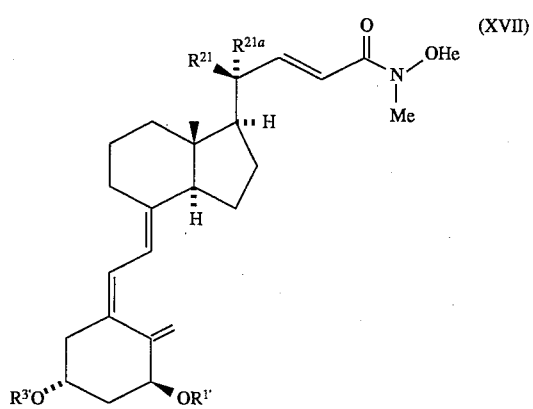
(XVII)

results, i n which $R^{1'}$ and $R^{3'}$ have the known meanings.

The primary alcohol function in a compound of general formula XV is now reacted with an oxidizing agent such as, e.g., pyridinium chlorochromate, pyridinium dichromate or oxalyl chloride/DMSO with forming a compound of general formula XVI

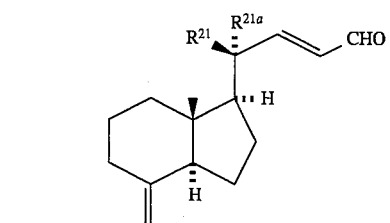
(XVIII)

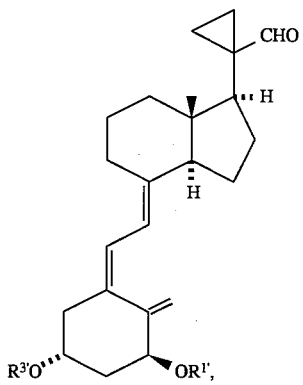
(XVI)

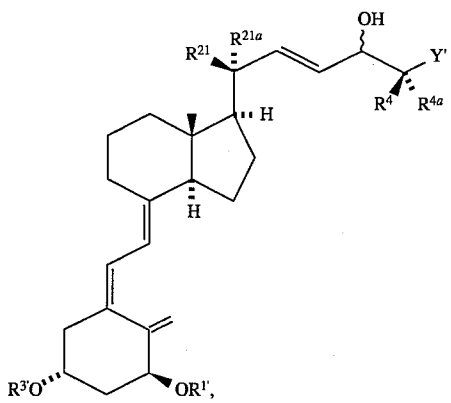
(XIX)

which $R^{1'}$ and $R^{3'}$ have the known meanings, that is derived from the compounds of general formula IV in that $R^{21}$ and $R^{21a}$ together with the quaternary carbon atom C-20 form a cyclopropyl ring and the triene system is already isomerized.

The introduction of the side chains takes place now on a compound of general formula X or XVI completely analogously to the description starting from a compound of general formula III, by the intermediate stages of general formulas XVII, XVIII and XIX, and finally a compound of general formula II is obtained, in which $R^{19}$ and $R^{21a}$ in both cases together form a methylene group and $R^{21}$ and $R^{21a}$ together also form a methylene group or together with C20 form a cyclopropyl ring. $R^1$, $R^{3'}$, $R^4$, $R^{4a}$ and Y' have the meaning already indicated.

The diastereomer separations or releasings and derivatizations of the hydroxy groups takes place as already described. Optionally, before the cleavage of the protective groups, the 24-hydroxy group is again oxidized as already described for the keto function.

For synthesis of the compounds of general formula II, in which $R^{19}$ and $R^{19a}$ each mean a hydrogen atom ("19-nor-series") aldehyde XX known in the literature is used

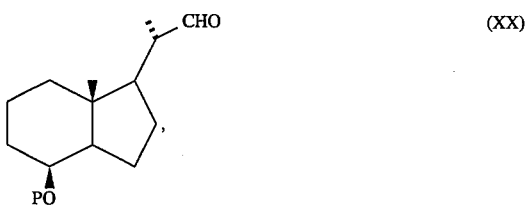
(XX)

(H. H. Inhoffen et al., Chem. Ber. 91, 780 (1958), Chem. Ber. 92, 1772 (1959); W. G. Dauben et al., Tetrahedron Lett. 30, 677 (1989), in which P means an acyl, alkyl or aryl substituted silyl or tetrahydropyranyl, tetrahydrofuranyl or methoxymethyl or another alcohol protective group.

The structural modifications on carbon atom 20 can take place analogously to the process already described above for the vitamin D derivative, and compounds of general formula XXI

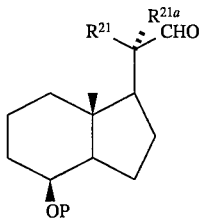

result, in which P has the already indicated meaning and $R^{21}$ and $R^{21a}$ each mean a methyl group, together a methylene group or together with carbon atom 20 a cyclopropyl ring. Further $R^{21}$ can mean a fluorine atom and $R^{21a}$ can mean a methyl group or $R^{21}$ can mean a methyl group and $R^{21a}$ can mean a fluorine atom. These substitution patterns can be made as follows:

A compound of general formula XXI is reacted with a base such as diisopropylethyl amine, triethylamine or 2,5-di-tert.-butylpyridine and a silylation reagent such as trimethylsilyl chloride or trimethylsilyltrifluorosulfonate to the E,Z mixture of silylenolether of general formula XXII

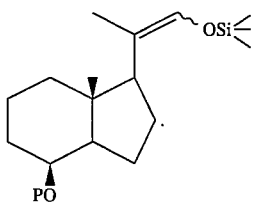

Reaction with an electrophilic fluorination reagent (e.g., N-fluorodiphenylsulfonimide, or the like) (E. Differding, H. Ofner, Synlett 187 (1991)) yields the α-fluoroaldehyde of general formula XXI of the above definition. Possibly occurring diastereomers can be chromatographically separated and further reacted separately.

The compounds modified as described in position 20 but also compounds of general formula XXI, for which $R^{21}$=hydrogen and $R^{21a}$=methyl (standard configuration) or $R^{21}$=methyl and $R^{21a}$=hydrogen ("20-epi-series") are converted as already described above for the vitamin D derivatives (analogously to III→VI) into compounds of general formula XXIII

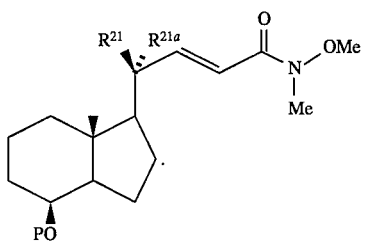

Protective group P in the compound of general formula XXIV is now cleaved under standard conditions: F or silylether protective groups, tetrabutylammoniumfluoride (TBAF), hydrogen fluoride or hydrogen fluoride-pyridine complex is used;

for tetrahydropyranyl, methoxymethyl or methoxyethoxymethyl ether acid reaction conditions (pyridinium-p-toluene sulfonate, p-toluene sulfonic acid, acetic acid, hydrochloric acid, acid ion exchanger) are used and a compound of general formula XXIV

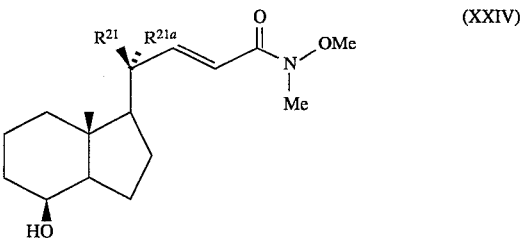

is produced.

The free hydroxyl group is oxidized with an oxidizing agent (pyridinium chlorochromate, pyridinium dichromate, barium manganate, oxalyl chloride or dimethylsulfoxide) to the ketone (compound of general formula XXV)

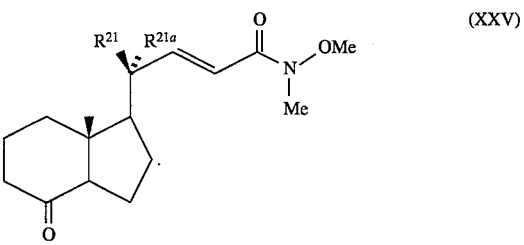

The compounds of general formula XXV are now converted (Horner-Wittig reaction) by reaction with the anion of phosphinoxide of general formula XXVI known in the literature (H. F. DeLuca et al. Tetrahedron Lett. 7663 (1991)) produced by a base such as n-butyllithium or lithium diisopropylamine

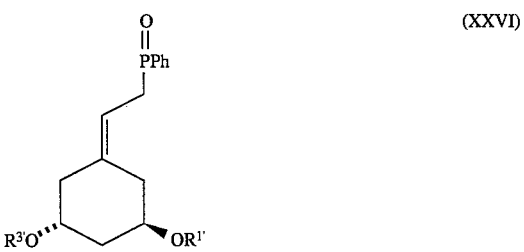

in which $R^{1'}$ and $R^{3'}$ mean alkyl, or aryl or alkyl-substituted silyl groups already indicated above in formula II into the corresponding compounds of general formula XXVII

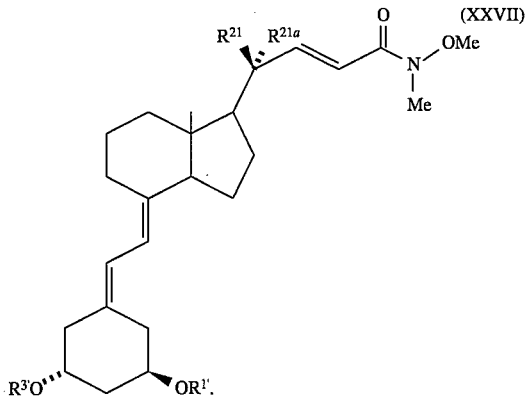

Analogously to the "standard series" by an intermediate stage of general formula XXIII

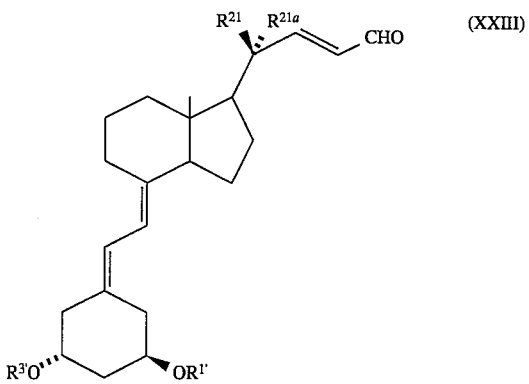

the corresponding compound of general formula II is produced in which $R^{19}$ and $R^{19a}$ each stand for a hydrogen atom and the latter then are converted as described above into a compound of general formula I.

The following examples are used to explain the invention in more detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German applications P 42 34 382.8 and P 43 17 415.9, are hereby incorporated by reference.

EXAMPLES

Production of the initial compounds in the standard series

1.) (5E,7E,22E)-(1S,3R)-1,3-Bis[[dimethyl(1,1-dimethylethyl)silyl]oxy]-N-methoxy-N-methyl-9,10-secochola-5,7,10(19),22-tetraene-24-amide 2

17.65 g of aldehyde 1 (Calverley, Tetrahedron 43 4609 (1987)) and 26.97 g of N-methoxy-N-methyl-2-(triphenylphosphoranylidene)acetamide (D. A. Evans et al., J. Am. Chem. Soc. 112 7001 (1990)) are stirred for 6 hours at 105° C. in 101 ml of DMSO. The cooled reaction mixture is stirred in NaCl solution, extracted with ethyl acetate, dried on sodium sulfate and concentrated by evaporation. The residue is purified on silica gel with ethyl acetate. 14.9 g of 2 is obtained as colorless crystallized oil.

$^1$H-NMR(300 MHz, CDCl$_3$): δ=0.05 ppm (s, 12H); 0.57 (s, 3H); 0.84 (s, 9H); 0.87 (s, 9H); 1.10(d, 7Hz, 3H); 3.24 (s, 3H); 3.72 (s, 3H); 4.23 (m, 1H); 4.53 (m, 1H); 4.94 (br. s, 1H); 4.99 (br. s, 1H); 5.83 (d, J=11 Hz, 1H); 6.33 (d, J=15 Hz, 1H); 6.45 (d, J=11 Hz, 1H); 6.85 (dd, J=15 Hz, J=9 Hz, 1H) .

2.) (5E,7E,22E)-(1S,3R)-1,3-Bis[[dimethyl(1,1-dimethylethyl)silyl]oxy]-9,10-secochola-5,7,10(19),22-tetraen-24-al 3

10.7 g of 2 in 54 ml of tetrahydrofuran is mixed drop by drop at −78° C. under nitrogen with 68.2 ml of diisobutylaluminum hydride (1.2 molar in toluene) and stirred for 70 minutes at −78° C. After drop by drop addition of 3.66 ml of methanol at −78° C., the reaction mixture is stirred in 1 l of ice/potassium-sodium tartrate solution. 700 ml of ether is added, stirred for 1.5 hour, extracted with ether, dried on sodium sulfate and concentrated by evaporation. 8.86 g of 3 is obtained as light yellow material by purification of the oily residue on silica gel with ethyl acetate/hexane.

3.) (5E,7E,22E) - (1S,3R,24R) -1,3 -Bis[[dimethyl(1,1-dimethylethyl)silyl]oxy]-24-hydroxy-9,10-secocholesta-5,7,10(19),22-tetraene-25-carboxylic acid ethyl ester 4a 4.6 ml of butyllithium (1.6 molar in hexane) is instilled with ice cooling under nitrogen in 1.13 ml of diisopropylamine in 51.6 ml of tetrahydrofuran and again stirred for 15 minutes. Then 0.99 ml of isobutyric acid ethyl ester is instilled at −78° C. and again stirred for 75 minutes. Then 2.0 g of 3 in 6.0 ml of tetrahydrofuran is instilled at the same temperature and stirred another 75 minutes at −78° C. The reaction mixture is mixed with saturated NH$_4$Cl solution at −78° C., diluted with ice-cooled NaCl solution at −10° C., extracted with ether, dried on sodium sulfate and concentrated by evaporation. 730 mg of (5E,7E,22E)-(1S,3R,24S)-1,3-bis[[dimethyl(1,1dimethylethyl)silyl]oxy]-24-hydroxy-9,10-secocholesta-5,7,10(19),22-tetraene-25-carboxylic acid ethyl ester (4b) as crystallized oil and 520 mg of title compound 4a as colorless oil are obtained in the elution sequence by chromatography of the oily residue on silica gel with ethyl acetate/hexane.

4.) (5Z,7E,22E) - (1S,3R,24R) -1,3-Bis[[dimethyl(1,1dimethylethyl)silyl]oxy]-24-hydroxy-9,10-secocholesta-5,7,10(19),22-tetraene-25-carboxylic acid ethyl ester 5a 520 mg of 4a is dissolved in 68 ml of toluene and after addition of 80 mg of anthracene and 1 drop of triethylamine it is irradiated for 13 minutes under nitrogen with a mercury high-pressure lamp (Heraeus TQ 150) through pyrex glass. The reaction mixture is concentrated by evaporation and the residue (600 mg) —a mixture of 5a and anthracene—is directly subjected to subsequent silyl ether cleavage.

5.) (5Z,7E,22E)-(1S,3R,24S)-1,3-Bis[[dimethyl(1,1dimethylethyl)silyl]oxy]-24-hydroxy-9,10-secocholesta-5,7,10(19),22-tetraene-25-carboxylic acid ethyl ester 5b 730 mg of 4b (relative to instruction 3) is dissolved in 95 ml of toluene and after addition of 80 mg of anthracene and 2 drops of triethylamine it is irradiated for 15 minutes under nitrogen with a mercury high-pressure lamp (Heraeus TQ 150) through pyrex glass. The reaction mixture is concentrated by evaporation and the residue (845 mg)—a mixture of 5b and anthracene—is directly subjected to subsequent silyl ether cleavage.

6.) (5E,7E,22E)-(1S,3R)-1,3-Bis[[dimethyl(1,1dimethylethyl)silyl]oxy]-24-oxo-26,27-cyclo-9,10-secocholesta-5,7,10(19),22-tetraene-25-carboxylic acid 6

38.8 ml of butyllithium (1.6 molar in hexane) is instilled with ice cooling under nitrogen in 9.5 ml of diisopropylamine in 607 ml of tetrahydrofuran and stirred for 15 minutes. Then 8.83 g of 1-acetylcyclopropane carboxylic acid methyl ester (D. F. Taber et al., J. Org. Chem. (1992) 57, 436) is instilled at −78° C. and stirred for 1 hour. Then 5.96 g of aldehyde 1 (Calverly, Tetrahedron 43 4609 (1987)) in 18.4 ml of tetrahydrofuran is instilled at −78° C. and stirred for 1.5 hours. Then the reaction mixture is allowed to reach 0° C. within 1.5 hours and it is stirred for 15 minutes more at this temperature. After addition of saturated ammonium chloride solution at −20° C. it is diluted with saturated sodium chloride solution at room temperature, extracted with ethyl acetate by addition of 5% oxalic acid, dried on sodium sulfate and concentrated by evaporation. The thus obtained crude product (11.90 g of yellow oil) is subjected to the subsequent esterification without further purification.

An NMR-sample is obtained after thin layer chromatographic (silica gel, ethyl acetate/hexane) purification.

$^1$H-NMR(300 MHZ, CDCl$_3$): δ=0.05 ppm (s, 12H); 0.57 (s, 3H); 0.84 (s, 9H); 0.87 (s, 9H); 1.10(d, J=7 Hz, 3H); 1.73 (m, 2H); 2.03 (m, 2H); 4.23 (m, 1H); 4.53 (m, 1H); 4.94 (br. s, 1H); 4.97 (br. s, 1H); 5.82 (d, J=11 Hz, 1H); 5.85 (d, J=15 Hz, 1H); 6.43 (d, J=11 Hz, 1H); 7.13 (dd, J=15 Hz, J=9 Hz, 1H).

7.) (5E,7E,22E)-(1S,3R)-1,3-Bis[[dimethyl(1,1dimethylethyl)silyl]oxy]-24-oxo-26,27-cyclo-9,10-secocholesta-5,7,10(19),22-tetraene-25-carboxylic acid methyl ester 7

11.90 g of 6 in 119 ml of methylene chloride is mixed drop by drop in succession with 7.28 ml of triethylamine and 2.06 ml of mesylchloride at −30° C. and stirred for 1 hour. Then 3.53 ml of methanol and 0.43 g of dimethylaminopyridine are added in succession at −30° C. After 1.25 hours at −10° C. the reaction mixture is poured on ice/sodium bicarbonate solution. Then it is diluted with sodium chloride solution, extracted with ethyl acetate, dried on sodium sulfate and concentrated by evaporation. Chromatography of the oily residue on silica gel with ethyl acetate/hexane yields 4.10 g of 7 as colorless material.

$^1$H-NMR(300 MHz, CDCl$_3$): δ=0.05 ppm (s, 12H); 0.57 (s, 3H); 0.85 (s, 9H); 0.89 (s, 9H); 1.10(d, J=7 Hz, 3H); 1.45 (m, 4H); 3.73 (s, 3H); 4.21 (m, 1H); 4.53 (m, 1H); 4.93 (br. s, 1H); 4.95 (br. s, 1H); 5.82 (d, J=11 Hz, 1H); 5.82 (d, J=11 Hz, 1H); 6.40 (d, J=15 Hz, 1H); 6.44 (d, J=11 Hz, 1H); 6.75 (dd, J=15 Hz, J=9 Hz, 1H).

8.) (5E,7E,22E)-(1S,3R,24R)-1,3-Bis[[dimethyl(1,1-dimethylethyl)silyl]oxy]-24-hydroxy-26,27-cyclo-9,10-secocholesta-5,7,10(19),22-tetraene-25-carboxylic acid methyl ester 8a 2.0 g of 7 in 4.8 ml of tetrahydrofuran and 5.8 ml of methanol is mixed with 11.2 ml of a 0.4 molar methanolic cerium(III)chloride-heptahydrate solution. 310 mg of sodium borohydride is added in portion with ice cooling under nitrogen. The reaction mixture is stirred for 45 minutes with ice cooling and then mixed with ice/water. Then it is extracted with ethyl acetate, dried on sodium sulfate and concentrated by evaporation. 610 mg of (5E,7E,22E)-(1S, 3R,24S)-1,3-bis[[dimethyl(1,1-dimethylethyl)silyl]oxy]-24-hydroxy-26,27-cyclo-9,10-secocholesta-5,7,10(19),22-tetraene-25-carboxylic acid methyl ester 8b and 370 of title compound 8a are obtained in the elution sequence as crystallized oil by chromatography of the residue on silica gel with ethyl acetate/hexane.

In the subsequent reactions only the further reaction of 8a is described.

9.) (5Z,7E,22E) - (1S,3R,24R) -1,3-Bis[[dimethyl(1,1-dimethylethyl)silyl]oxy]-24-hydroxy-26,27-cyclo-9,10-secocholesta-5,7,10(19),22 -tetraene-25-carboxylic acid methyl ester 9a 370 mg of 8a is dissolved in 53 ml of toluene and after addition of 61 mg of anthracene and 1 drop of triethylamine it is irradiated for 5 minutes under nitrogen with a mercury high-pressure lamp (Heraeus TQ 150) through pyrex glass. The reaction mixture is concentrated by evaporation and the residue (435 mg) —a mixture of 9a and anthracene—is directly subjected to subsequent silyl ether cleavage.

EXAMPLE 1

10) (5Z,7E,22E)-(1S,3R,24R)-1,3,24-Trihydroxy-9,10-secocholesta-5,7,10(19),22-tetraene-25-carboxylic acid ethyl ester 10a 600 mg of the residue from 5a is stirred with 9.23 g of Dowex 50WX8 in 22.5 ml of methanol/methylene chloride (9:1) for 25 hours at room temperature. The suspension is filtered, the filtrate concentrated by evaporation and the residue chromatographed on silica gel with ethyl acetate/hexane. 201 mg of 10a is obtained as foam.

$^1$H-NMR(300 MHz, CDCl$_3$): δ=0.58 ppm (s, 3H); 1.05 (d, J=7 Hz, 3H); 1.17 (s, 6H); 1.28 (t, J=7 Hz, 3H); 2.60 (m, 2H); 4.08 (br. t, 1H); 4.15 (q, J=7 Hz, 2H); 5.00 (br. s, 1H); 5.32 (br. s, 1H); 5.36 (dd, J=15 Hz, J=7.5 Hz, 1H); 5.55 (dd, J=15 Hz, J=9 Hz, 1H); 6.02 (d, J=11 Hz, 1H); 6.48 (d, J=11 Hz, 1H).

EXAMPLE 2

11) (5Z,7E,22E)-(1S,3R,24S)-1,3,24-Trihydroxy-9,10-secocholesta-5,7,10(19),22-tetraene-25-carboxylic acid ethyl ester 10b 845 mg of the residue from 5b is stirred with 12.95 g of Dowex 50WX8 in 31.6 ml of methanol/methylene chloride (9:1) for 25 hours at room temperature. The suspension is filtered, the filtrate is concentrated by evaporation and the residue is chromatographed on silica gel with ethyl acetate/hexane. 251 mg of the title compound of a melting point of 133°–134° C. is isolated.

EXAMPLE 3

12) (5Z,7E,22E) - (1S,3R,24R) -26,27-Dimethyl-1,3,24-trihydroxy-9,10-secocholesta-5,7,10(19),22-tetraene-25carboxylic acid methyl ester 11a Starting from aldehyde 3 and 2-ethylbutyric acid methyl ester title compound 11a is obtained as foam analogously to the sequence of the synthesis of 10a from 4a.

$^1$H-NMR(300 MHz, CDCl$_3$) : δ=0.57 ppm (s, 3H); 0.82 (t, J=7.5 Hz, 3H); 0.88 (t, J=7.5 Hz, 3H); 1,05 (d, J=7 Hz, 3H); 1.72 (q, J=7.5 Hz); 2.95 (d, J=6.5 Hz, 1H); 3.72 (s, 3H); 4.15 (br. t, 1H); 4.23 (m, 1H); 4.42 (m, 1H); 5.00 (br. s, 1H); 5.32 (br. s, 1H); 5.37 (dd, J=15 Hz, J=7.5 Hz, 1H); 5.55 (dd, J=15 Hz, J=9 Hz, 1H); 6.02 (d, J=11 Hz, 1H); 6.39 (d, J=11 Hz, 1H).

EXAMPLE 4

13) (5Z,7E,22E)-(1S,3R,24R)-1,3,24-Trihydroxy-9,10-secocholesta-5, 7,10(19),22-tetraene-25-carboxylic acid-1-methyl ethyl ester 13a 580 mg of (5Z,7E,22E) - (1S,3R,24R) -1,3-bis[[dimethyl(1,1-dimethylethyl)silyl]oxy]-24-hydroxy-9,10-secocholesta-5,7,10(19),22-tetraene-25-carboxylic acid-1-methyl ethyl 12a—contaminated with anthracene—is obtained starting from 1.82 g of aldehyde 3 and isobutyric acid isopropyl ester analogously to 4a and 5a.

20 ml of tetrahydrofuran and 1.06 g of tetrabutylammonium fluoride trihydrate are added for silyl ether cleavage. The reaction mixture is stirred for 50 minutes at 60° C. and after cooling it is poured on ice/sodium bicarbonate solution. Then it is extracted with ethyl acetate, dried on sodium sulfate and concentrated by evaporation. Chromatography on silica gel with ethyl acetate/hexane yields 68 mg of 13a as foam.

$^1$H-NMR(300 MHz, CDCl$_3$): δ=0.57 ppm (s, 3H); 1.05 (d, J=7 Hz, 3H); 1.16 (s, 3H); 1.17 (s, 3H); 1.27 (d, J=7 6H); 2.70 (br. d, 1H); 4.05 (m, 1H); 4.24 (m, 1H); 4.44 1H); 5.05 (m, 2H); 5.31 (br.s, 1H); 5.36 (dd, J=15 Hz, J=7.5 Hz, 1H); 5.51 (dd, J=15 Hz, J=9 Hz, 1H); 6.02 (d, J=11 Hz, 1H); 6.38 (d, J=11 Hz, 1H).

EXAMPLE 5

14) (5Z,7E,22E) - (1S,3R,24R) -1,3,24-Trihydroxy-9,10-secocholesta-5,7,10(19),22 -tetraene-25-carboxylic acid methyl ester 15a 540 mg of (5Z,7E,22E) - (1S,3R,24R) -1,3-bis [[dimethyl(1,1-dimethylethyl)silyl]oxy]-24-hydroxy-9,10-secocholesta-5,7,10(19),22-tetraene-25-carboxylic acid methyl ester 14a—contaminated with anthracene—is obtained starting from 1.82 g of aldehyde 3 and 0.77 ml of isobutyric acid methyl ester analogously to 4a and 5a.

For silyl ether cleavage it is dissolved in 5 ml of tetrahydrofuran and 0.098 ml of glacial acetic acid. 110 mg of the title compound of a melting point of 145° C. is isolated after a three-time addition of 865 mg of tetrabutylammonium fluoride-trihydrate and treatment in each case (2 hours 40° C.; 1.5 hours 40° C. and 12 hours room temperature; 5 hours 60° C.) with usual working up (relative to 13a).

EXAMPLE 6

15) (5Z,7E,22E) - (1S,3R,24S) -1,3,24-Trihydroxy-9,10-secochola-5,7,10(19),22-tetraene-24-acetic acid methyl ester 16a Title compound 16a is obtained as foam starting from aldehyde 3 and acetic acid methyl ester analogously to the reaction sequence of 15a.

$^1$H-NMR(300 MHz, CDCl$_3$): $\delta$=0.57 ppm (s, 3H); 1.05 (d, J=7 Hz, 3H); 2.54 (d, J=5 Hz, 2H); 2.70 (br. d, 1H); 3.71 (s, 3H); 4.23 (m, 1H); 4.47 (m, 2H); 5.00 (br. s, 1H); 5.32 (br. s, 1H); 5.40 (dd, J=15 Hz, J=7.5 Hz, 1H); 5.56 (dd, J=15 Hz, J=9 Hz, 1H); 6.01 (d, J=11 Hz, 1H); 6.38 (d, J=11 Hz, 1H).

EXAMPLE 7

16) (5Z,7E,22E)-(1S,3R,24R)-1,3,24-Trihydroxy-9,10-secocholesta-5,7,10(19),22-tetraene-25-carboxylic acid nitrile 17a Title compound 17a is obtained as crystallized oil of a melting point of 138° C. starting from aldehyde 3 and isobutyric acid nitrile analogously to the sequence of the synthesis of 6a from 4a.

EXAMPLE 8

17) (5Z,7E,22E)-(1S,3R,24R)-1,3,24-Trihydroxy-9,10-secocholesta-5,7,10(19),22-tetraene-25-carboxylic acid propyl ester 17a Title compound 19a is obtained as solid of a melting point of 123° C. starting from aldehyde 3 and isobutyric acid propyl ester analogously to the sequence of the synthesis of 6a from 4a by the intermediate product (5E, 7E,22E)-(1S, 3R,24R)-1,3-bis[[dimethyl(1,1-dimethylethyl)silyl]oxy]-24-hydroxy-9,10-secocholesta-5,7,10(19),22-tetraene-25-carboxylic acid propyl ester 18a.

EXAMPLE 9

18) (5Z,7E,22E)-(1S,3R,24R)-1,3,24-Trihydroxy-9,10-secocholesta-5,7,10(19),22-tetraene-25-carboxylic acid 21a 1.04 g of (5E, 7E,22E) - (1S,3R,24R) -1,3-bis[[dimethyl(1,1 -dimethylethyl)silyl]oxy]-24-hydroxy-9,10-secocholesta-5,7,10(19),22-tetraene-25-carboxylic acid-2-(trimethylsilyl)ethyl ester 20a—contaminated with anthracene —is obtained starting from 3.10 g of aldehyde 3 and 2.92 g of isobutyric acid-2-(trimethylsilyl)ethyl ester—produced from isobutyric acid and 2-(trimethyl-silyl)-ethanol in the presence of N,N'-dicyclohexylcarbodiimide and 4-dimethylaminopyridine (of Tetrahedron Lett. (1978) 4475—analogously to the synthesis of 4a and 5a. For silyl ether and ester cleavage 100 mg of 20a in 3.7 ml of tetrahydrofuran is left standing with 196 mg of tetrabutylammonium fluoride trihydrate for 5 days at room temperature. The reaction mixture is poured on ice/ammonium chloride solution and extracted with ethyl acetate. After drying on sodium sulfate it is concentrated by evaporation and the colorless, solid residue is stirred in ethyl acetate. 23 mg of title compound 21a of a melting point of 208° C. (decomposition) is obtained by filtration of the suspension.

EXAMPLE 10

19) (5Z,7E,22E)-(1S,3R,24R)-1,3,24-Trihydroxy-26,27-cyclo-9,10-secocholesta-5,7,10(19),22-tetraene-25carboxylic acid methyl ester 22a 435 mg of the residue from 9a in 15.4 ml of tetrahydrofuran is allowed to stand overnight at room temperature with 815 mg of tetrabutylammonium fluoride trihydrate. The reaction mixture is poured on ice/sodium bicarbonate solution and sodium chloride solution is added. Then it is extracted with ethyl acetate, dried on sodium sulfate and concentrated by evaporation. Chromatography of the residue on silica gel with ethyl acetate/hexane yields 130 mg of a light brown material. 45 mg of 22a of a melting point of 100°–101° C. is obtained after recrystallization in ethyl acetate/cyclohexane.

EXAMPLE 11

20) (5Z,7E,22E)-(1S,3R,24R)-1,3,24-Trihydroxy-26,27-cyclo-9,10-secocholesta-5,7,10(19),22-tetraene-25-carboxylic acid ethyl ester 23a Title compound 23a is obtained as foam starting from carboxylic acid 6 and ethanol analogously to the sequence of the synthesis of 22a from 7.

$^1$H-NMR(300 MHz, CDCl$_3$): $\delta$=0.57 ppm (s, 3H); 0.86 (m, 1H); 0.95 (m, 1H); 1.05 (d, J=7 Hz, 3H); 1.25 ((t, J=7 Hz, 5H); 3.17 (d, J=6.5 Hz, 1H); 3.97 (br. t, 1H); 4.15 (q, J=7 Hz, 2H); 4.22 (m, 1H); 4.43 (m, 1H); 4.99 (br. s, t, 1H); 5.33 (br. s, 1H); 5.41 (dd, J=15 Hz, J=7.5 Hz, 1H); 5.52 (dd, J=15 Hz, J=9 Hz, 1H); 6.01 (d, J=11 Hz, 1H); 6.38 (d, J=11 Hz, 1H).

EXAMPLE 12

21) (5Z,7E,22E) - (1S,3R,24R) -1,3,24-Trihydroxy-26, 27-cyclo-9,10-secocholesta-5,7,10(19),22-tetraene-25carboxylic acid propyl ester 24a Title compound 24a is obtained as foam starting from carboxylic acid 6 and propanol analogously to the sequence of the synthesis of 22a from 7.

$^1$H-NMR(300 MHz, CDCl$_3$): $\delta$=0.57 ppm (s, 3H); 0.86 (m, 1H); 0.95 (t, J=7 Hz, 4H); 1.05 (d, j=7 Hz, 3H); 1.23 (m, 2H); 3.19 (d, J=6.5 Hz, 1H); 3.96 (br. t, 1H); 4.04 (t, J=7 Hz, 2H); 4.22 (m, 1H); 4.42 (m, 1H); 4.99 (br. s, H); 5.32 (br. s, 1H); 5.41 (dd, J=15 Hz, J=7.5 Hz, 1H); 5.52 (dd, J=15 Hz, J=9Hz, 1H); 6.01 (d, J=11 Hz, 1H); 6.38 (d, J=11 Hz, 1H).

EXAMPLE 13

22) (5Z,7E,22E) - (1S,3R,24R) -1,3,24-Trihydroxy-26, 27-cyclo-9,10-secocholesta-5,7,10(19),22-tetraene-25-carboxylic acid butyl ester 25a Title compound 25a is obtained as foam starting from carboxylic acid 6 and butanol analogously to the sequence of the synthesis of .22a from 7.

$^1$H-NMR(300 MHz, CDCl$_3$) : δ=0.57 ppm (s, 3H); 0.86 (m, 1H); 0.93 (t, J=7 Hz, 4H); 1.05 (d, j=7 Hz, 3H); 1.25 (m, 2H); 3.19 (d, J=6.5 Hz, 1H); 3.97 (br. t, 1H); 4.10 (t, J=7 Hz, 2H); 4.24 (m, 1H); 4.43 (m, 1H); 5.00 (br. s, 1H); 5.32 (br. s, 1H); 5.41 (dd, J=15 Hz, J=7.5 Hz, 1H); 5.52 (dd, J=15 Hz, J=9 Hz, 1H); 6.01 (d, J=11 Hz, 1H); 6.38 (d, J=11 Hz, 1H).

EXAMPLE 14

23) (5Z,7E,22E)-(1S,3R,24R)-1,3,24-Trihydroxy-26,27-cyclo-9,10-secocholesta-5,7,10(19),22-tetraene-25-carboxylic acid-2-methyl propyl ester 26a Title compound 26a is obtained as foam starting from carboxylic acid 6 and 2-methyl-1-propanol analogously to the sequence of the synthesis of 22a from 7.

$^1$H-NMR(300 MHz, CDCl$_3$): δ=0.57 ppm (s, 3H); 0.86 (m, 1H); 0.92 (t, J=7 Hz, 4H); 1.05 (d, J=7 Hz, 3H); 1.25 (m, 2H); 3.20 (d, J=6.5 Hz, 1H); 3.87 (d, J=7 Hz, 2H); 3.98 (br. t, 1H); 4.25 (m, 1H); 4.45 (m, 1H); 4.99 (br. s, 1H); 5.32 (br. s, 1H); 5.41 (dd, J=15 Hz, J=7.5 Hz, 1H); 5.52 (dd, J=15 Hz, J=9 Hz, 1H); 6.01 (d, J=11 Hz, 1H); 6.38 (d, J=11 Hz, 1H).

EXAMPLE 15

24) (5Z,7E,22E) - (1S,3R,24R) -1,3,24-Trihydroxy-26,27-cyclo-9,10-secocholesta-5,7,10(19),22 -tetraene-25-carboxylic acid pentyl ester 27a Title compound 27a is obtained as foam starting from carboxylic acid 6 and pentanol analogously to the sequence of the synthesis of 22a from 7.

$^1$H-NMR (300 MHz, CDCl$_3$); δ=0.57 ppm (s, 3H); 0.90 (m, 5H); 1.05 (d, J=7 Hz, 3H); 3.20 (br, s, 1H); 3.98 (br, d, 1H); 4,08 (t, J=7 Hz, 2H); 4.23 (m, 1H); 4.42 (m, 1H); 5.00 (br, s, 1H); 5.32 (br, s, 1H); 5.41 (dd, J=15 Hz, J=7.5 Hz, 1H); 5.52 (dd, J=15 Hz, J=9 Hz, 1H); 6.00 (d, J=11 Hz, 1H); 6.38 (d, J=11 Hz, 1H).

EXAMPLE 16

25) (5Z,7E,22E) - (1S,3R,24R) -1,3,24-Trihydroxy-26,27-cyclo-9,10-secocholesta-5,7,10(19),22-tetraene-25-carboxylic acid hexyl ester 28a Title compound 28a is obtained as foam starting from carboxylic acid 6 and hexanol analogously to the sequence of the synthesis of 22a from 7.

$^1$H-NMR (300 MHz, CDCl$_3$); δ=0.57 ppm (s, 3H); 0.90 (m, 5H); 1.05 (d, J=7 Hz, 3H); 3.2 (br, s, 1H); 3.98 (br, d, 1H); 4.08 (t, J=7 Hz, 2H); 4.23 (m, 1H); 4.42 (m, 1H); 5.00 (br, s, 1H); 5.32 (br, s, 1H); 5.41 (dd, J=15 Hz, J=7.5 Hz, 1H); 5.52 (dd, J=15 Hz, J=9 Hz, 1H); 6.00 (d, J=11 Hz, 1H); 6.38 (d, J=11 Hz, 1H).

Initial compounds for the 25-carboxylic acid amides (standard series) and examples 26) (5E,7E,22E)-(1S,3R,24R)-1,3-Bis[[dimethyl(1,1-dimethylethyl)silyl]oxy]-24-hydroxy-9,10-secocholesta-5,7,10(19),22-tetraene-25-carboxylic acid dimethyl amide 29a 3.0 g of aldehyde 3 and 1.32 g of activated zinc [E. A. Hallinau et al. Tetrahedron Lett. 25 2301 (1984)] are refluxed in 40 ml of tetrahydrofuran for 5 minutes in a nitrogen atmosphere. Then 3.92 g of α-bromo-isobutyric acid dimethyl amide [Lauceill et al, C. R. 248 3311 (1959)] is added and the reaction mixture is refluxed for 1 hour more. The cooled reaction mixture is stirred in an ice/KHSO$_4$ solution, extracted with ethyl acetate, dried on sodium sulfate and concentrated by evaporation. 1.01 g of (5E,7E,22E) - (1S,3R,24R) -1,3-bis[[dimethyl(1,1-dimethylethyl)silyl]oxy]-24-hydroxy-9,10-secocholesta-5,7,10(19),22-tetraene-25-carboxylic acid dimethyl amide 29b and 0.49 g of title compound 29a is obtained in the elution sequence as crystallized material by chromatography of the oily residue on silica gel with ethyl acetate/hexane.

The further reaction of 8a is now described in the subsequent reactions.

27) (5Z,7E,22E)-(1S,3R,24R)-1,3-Bis[[dimethyl(1,1-dimethylethyl)silyl]oxy]-24-hydroxy-9,10-secocholesta-5,7,10(19),22-tetraene-25-carboxylic acid amide 30a 0.48 g of 29a is dissolved in 68 ml of toluene and after addition of 74 mg of anthracene and 1 drop of triethylamine it is irradiated through pyrex glass for 30 minutes under nitrogen with a mercury high-pressure lamp (Heraeus TQ 150). The reaction mixture is concentrated by evaporation and the residue (0.56 g)—a mixture of 30a and anthracene— is directly subjected to the subsequent silyl ether cleavage.

EXAMPLE 17

28) (5Z,7E,22E)-(1S,3R,24R)-1,3,24-Trihydroxy-9,10-secocholesta-5,7,10(19),22-tetraene-25-carboxylic acid dimethyl amide 31a 0.56 g of the residue from 30a is stirred with 8.5 g of Dowex 50WX8 in 20.8 ml of methanol/methylene chloride (9:1) for 30 hours at room temperature. The suspension is filtered, the filtrate concentrated by evaporation and the residue chromatographed on silica gel with ethyl acetate/ hexane. 242 mg of 31a is obtained as crystallized oil.

$^1$H-NMR(300 MHz, CDCl$_3$): δ=0.57 ppm (S,3H); 1.06 (d, J=7 Hz, 3H); 1.28 (S,6H); 3.05 (S,6H); 4.05 (br. t, 1H); 4.23 (m, 1H); 4.43 (br. d, 2H); 4.99 (br. t, 1H); 5.30 (br. S,1H); 5.50 (br. t, 1H); 6.00 (d, J=11 Hz, 1H); 6.38 (d, J=11 Hz, 1H).

EXAMPLE 18

29) (5Z,7E,22E) - (1S,3R,24R)-1,3,24-Trihydroxy-9,10-secocholesta-5,7,10(19 ),22 -tetraene-25-carboxylic acid diethyl amide 32a Title compound 32a is obtained as foam starting from aldehyde 3 and α-bromoisobutyric acid diethylamide [Neemau, J.Chem. Soc. 2525 (1955)] analogously to the sequence of examples 29a–31a.

$^1$H-NMR(300 MHz, CDCl$_3$) : δ=0.57 ppm (S,3H); 1.05 (d, J=7 Hz, 3H); 1.15 (br. t, 6H); 1.22 (S,3H); 1.23 (S, 3H); 3.38 (m, 1H); 4.00 (br. t, 1H); 4.20 (m, 1H); 4.40 (m, 1H); 4.58 (br. d, 1H); 4.98 (br. S,1H); 5.30 (br, S, 1H); 5.48 (m, 2H); 6.00 (d, J=11 Hz, 1H); 6.38 (d, J=11 Hz, 1H).

30) (5E,7E,22E)-(1S,3R)-1,3-Bis[[dimethyl(1,1dimethylethyl)silyl]oxy]-24-oxo-26,27-cyclo-9,10-secocholesta-5,7,10(19),22-tetraene-25-carboxylic acid diethyl amide 33

8.31 g of crude product of carboxylic acid 6 and 2.51 g of N,N'-dicyclohexylcarbodiimide in 25.1 ml of methylene chloride are mixed with ice cooling with 1.40 g of N-hydroxysuccinimide and, after 30 minutes, 976 mg of diethylamine is added. The reaction mixture is stirred for 40 minutes with ice cooling and allowed to stand overnight at room temperature. Then it is extracted with saturated sodium chloride solution/ethyl acetate, the organic phase is dried with sodium sulfate and concentrated by evaporation. Chromatography of the residue on silica gel with ethyl acetate/ hexane yields 2.94 g of 33 as oil.

31) (5E,7E,22E)-(1S,3R,24R)-1,3-Bis[[dimethyl(1,1dimethylethyl)silyl]oxy]-24-hydroxy-26,27-cyclo-9,10-secocholesta-5,7,10(19),22-tetraene-25-carboxylic acid diethyl amide 34a 3.60 g of 33 in 8.2 ml of tetrahydrofuran and 18.9 ml of methanol are mixed with 18.9 ml of a 0.4 molar methanolic cerium(III)chloride-heptahydrate solution. 520 mg of sodium borohydride is added in portions with ice cooling under nitrogen. The reaction mixture is stirred for 90 minutes with ice cooling and then mixed with ice/water. Then it is extracted with ethyl acetate, the organic phase dried on sodium sulfate and concentrated by evaporation. 760 mg of (5E,7E,22E) - (1S,3R,24S) -1,3-bis [[dimethyl(1,1-dimethylethyl) silyl]oxy]-24-hydroxy-26,27-cyclo-9,10-secocholesta-5,7,10(19),22-tetraene-25-carboxylic acid diethyl amide 34b and 300 mg of title compound 34a are obtained as crystallized oil by chromatography of the residue on silica gel with ethyl acetate/hexane in the elution sequence.

Only the further reaction of 34a is described in the subsequent reactions.

32) (5Z,7E,22E)-(1S,3R,24R)-1,3-Bis[[dimethyl(1,1dimethylethyl)silyl]oxy]-24-hydroxy-26,27-cyclo-9,10-secocholesta-5,7,10(19),22-tetraene-25-carboxylic acid diethyl amide 35a 290 mg of 34a and 42 mg of anthracene in 50 ml of toluene are irridated with a mercury high-pressure lamp in the presence of 1 drop of triethylamine for 5 minutes under nitrogen. The reaction mixture is concentrated by evaporation and the residue (330 mg)—a mixture of 35a and anthracene—is subjected to subsequent silyl ether cleavage.

EXAMPLE 19

33) (5Z,7E,22E) - (1S,3R,24R) -1,3,24-Trihydroxy-26,27-cyclo-9,10-secocholesta-5,7,10(19),22-tetraene-25-carboxylic acid diethyl amide 36a 330 mg of the residue from 35a in 11.4 ml of tetrahydrofuran is allowed to stand overnight with 605 mg of tetrabutylammonium fluoride trihydrate. The reaction mixture is poured on ice/sodium bicarbonate solution and sodium chloride solution is added. Then it is extracted with ethyl acetate, dried on sodium sulfate and concentrated by evaporation. Chromatography of the residue on silica gel with ethyl acetate/hexane yields 100 mg of title compound 36a as foam.

$^1$H-NMR(300 MHz, CDCl$_3$): δ=0.55 ppm (S,3H); 0.85 (m, 4H); 1.02 (d, J=7 Hz, 3H); 1.14 (br. t, 6H); 2.76 (br. d, 1H); 3.4 (m, 4H); 3.95 (br. t, 1H); 4.23 (m, 1H); 4.43 (m, 1H); 5.00 (br. s, 1H); 5.30 (dd, J=15 Hz, J=7.5 Hz, 1H); 5.32 (br. s, 1H); 5.56 (dd, J=15 Hz, J=9 Hz, 1H); 6.02 (d, J=11 Hz, 1H); 6.48 (d, J=11 Hz, 1H).

34) (5Z,7E) - (1S,3R,20S) -1,3-Bis [[dimethyl(1,1dimethylethyl)silyl]oxy]-formyl-9,10-secopregna-5,7,10(19)-triene 37

1.0 g of aldehyde 1 and 192 mg of anthracene are irridated in a mercury high-pressure lamp in the presence of 3 drops of triethylamine for 15 minutes under nitrogen. This process is repeated two times more. The combined reaction mixtures are concentrated by evaporation and the residue of 3.6 g is directly subjected to the subsequent reaction.

35) (5Z,7E,22E)-(1S,3R)-1,3-Bis[[dimethyl(1,1-dimethylethyl)silyl]oxy]-24-oxo-26,27-cyclo-9,10-secocholesta-5,7,10(19),22-tetraene-25-carboxylic acid 38

19.4 ml of butyllithium (1.6 molar in hexane) is instilled with ice cooling under nitrogen in 4.79 ml of diisopropylamine in 304 ml of tetrahydrofuran and stirred for 15 minutes. Then 4.42 g of 1-acetylcyclopropanecarboxylic acid methyl ester [D. F. Taber et al., J.Org. Chem. 57 436 (1992)]is instilled at −78° C. and stirred for 1 hour. Then aldehyde 37 in 9.2 ml of tetrahydrofuran is instilled at −78° C. and stirred for 1.5 hours at −78° C. The reaction mixture is allowed to come to −10° C. in 100 minutes and then saturated ammonium chloride is added. The reaction mixture is diluted with sodium chloride solution and extracted with ethyl acetate in the presence of 5% oxalic acid. The organic phase is washed with sodium chloride solution, dried on sodium sulfate and concentrated by evaporation. 7.7 g of crude product of the title compound is obtained as oil.

36) (5Z,7E,22E)-(1S,3R)-1,3-Bis[[dimethyl(1,1-dimethylethyl)silyl]oxy]-24-oxo-26,27-cyclo-9,10-secocholesta-5,7,10(19),22-tetraene-25-carboxylic acid-n-butylamide 39

7.70 g of 38 and 1.30 g of N-hydroxysuccinimide are dissolved in 15 ml of methylene chloride and 2.33 g of N,N'-dicyclohexylcarbodiimide is added at 0° C. After 40 minutes 1.12 ml of n-butylamine is added and stirred for 5 hours at room temperature. After standing overnight the reaction mixture is diluted with ice/sodium chloride solution. Then it is extracted with ethyl acetate, the organic phase is dried on sodium sulfate and concentrated by evaporation. 1.84 g of crude product of title compound is obtained 39 as oil

EXAMPLE 20

37) (5Z,7E,22E) - (1S,3R) -1,3-Dihydroxy-24-oxo-26,27-cyclo-9,10-secocholesta-5,7,10(19),22-tetraene-25carboxylic acid-n-butylamide 40

970 mg of 39 is dissolved in 38 ml of methylene chloride/methanol (1: 9) and stirred with 16.28 g of D©WEX 50WX8 for 26 hours at room temperature. After filtration and concentration by evaporation of the filtrate, the residue is chromatographed on silica gel with ethyl acetate/hexane. 340 mg of 40 is obtained as foam.

$^1$H-NMR(300 MHz, CDCl$_3$): δ=0.58 ppm (s, 3H); 0.93 (t, J=7.5 Hz, 3H); 1.08 (d, J=7 Hz, 3H); 1.50 (m, 4H); 3.30 (J=5 Hz, 2H); 4.24 (m, 1H); 4.45 (m, 1H); 4.98 (br. s, 1H); 5.22 (br. s, 1H); 5.85 (d, J=15 Hz, 1H); 6.00 (d, J=11 Hz, 1H); 6.38 (d, J=11 Hz, 1H); 6.91 (dd, J=15 Hz, J=9 Hz, 1H); 8.95 (br. t, 1H).

Initial material in the 20-methyl series (tert.butyldiphenylsilyl protective groups).

38) (5E,7E)-(1S,3R)-1,3-Bis[[1,1-dimethylethyl (diphenyl)silyl]oxy]-20-formyl-20-methyl-9,10-secopregna-5,7,10(19) -triene 42

140 mg (4.5 mmol) of sodium hydride (80%) is introduced into 20 ml of tetrahydrofuran and the oxygen is removed by repeated degassing in a vacuum and flushing with argon. Now 2.5 g (3.0 mmol) of (5F,7E) - (1S,3R, 20S)1,3-bis[[1,1-dimethylethyl(diphenyl)silyl]oxy]-20-formyl-9,10-secopregna-5,7,10(19)-triene 41 (M. Calverley Tetrahedron 43, 4609 (1987), WO 87/00834, tert.-butyldimethylsilyl protective groups) in 20 ml of tetrahydrofuran and then 1.87 g (13.5 mmol) of methyliodide are instilled at 0° C. It is stirred overnight at room temperature, then the reaction mixture is poured on sodium chloride solution, extracted with ethyl acetate, the organic phase is washed with sodium chloride solution, dried on sodium sulfate, the solvent is removed and the crude product is purified by chromatography on silica gel with hexane/ethyl acetate as mobile solvent, and 2.0 g of the title compound is obtained as colorless foam.

$^1$H-NMR(CDCl$_3$): δ=0.52 ppm (s, 3H, H-18); 0.96 and 0.98 (2x s; 9H, Si-t-butyl each); 1.13 and 1.15 (2x s; 3H, H-21 and C-20-Me each); 4.29 (m, 1H, H-3); 4.64 (m, 1H, H-1); 4.73 and 4.90 (2x s; 1H, H-19 each); 5.62 and 6.38 (2x d, J=11 Hz; 1H, H-6 and H-7 each); 7.22–7.68 (m, 20H, Si-phenyl); 9.68 (s, 1H, H-22). (The steroid numbering is used throughout for classification.)

39) (5E,7E,22E) - (1S,3R) -Bis [[1,1-dimethylethyl-(diphenyl)silyl]oxy]-20,N-dimethyl-N-methoxy-9,10-seco-chola-5,7,10(19),22-tetraene-24-amide 43

2.0 g (2.44 mmol) of 42 and 5.2 g (14.6 mmol) of N-methoxy-N-methyl - 2 (triphenylphosphoranylidene)acetamide [D. A. Evans et al. J.Am. Chem. Soc. 112, 7001 (1990)] in 100 ml of toluene is stirred under argon for 48 hours at 80° C. After cooling the solution is concentrated by evaporation and the residue is chromatographed on silica gel with hexane/ethyl acetate, and, in addition to 905 mg of initial material, 880 mg of the title compound remain as colorless foam.

$^1$H-NMR(CDCl$_3$) : δ=0.53 ppm (s, 3H, H-18); 0.99 (s, 18H, Si-t-butyl); 1.16 and 1.18 (2x s; 3H, H-21 and C-20-Me each); 3.27 (s, 3H, N-Me); 3.70 (s, 3H, N-OMe); 4.29 (m, 1H, H-3); 4.60 (m, 1H, H-1); 4.68 and 4.88 (2x s; 1H, H-19 each); 5.60 and 6.38 (d, J=11 Hz; 1H, H-6 and H-7 each); 6.30 (d, J=16 Hz, 1H, H-23); 7.19 (d, J=16 Hz, 1H, H-22); 7.23–7.70 (m, 20H, Si-phenyl).

40) (5E,7E,22E) - (1S,3R) -1,3-Bis[[1,1-dimethylethyl-(diphenyl) silyl]oxy]-20-methyl-9,10-secochola-5,7,10(19), 22-tetraen-24-ol 44

880 mg (0.96 mmol) 43 is dissolved under argon in 15 ml of tetrahydrofuran, cooled to −78° C. and 4.2 ml (5 mmol) of DIBAH solution (1.2M in toluene) is instilled. After 2 hours 0.3 ml of methanol is added at −78° C. and stirred for 1 hour more at room temperature. Then the precipitate is filtered off, the filtrate is concentrated by evaporation and the residue is purified chromatographically and 690 mg of the title compound is obtained as colorless foam.

$^1$H-NMR(CDCl$_3$): δ=0.51 ppm (s, 3H, H-18); 0.98 (s, 18H, Si-t-butyl); 1.16 and 1.20 (2x s; 3H, H-21 and C-20-Me each); 4.30 (m, 1H, H-3); 4.61 (m, 1H, H-1); 4.70 and 4.88 (2x x; 1H, H-19 each); 5.61 and 6.37 (2x d, J=11 Hz; 1H, H-6 and H-7 each); 6.07 (dd, J=16.8 Hz, 1H, H-23); 7.04 (d, J=16 Hz, 1H, H-22); 7.22-7.68 (m, 20H, Si-phenyl); 9.57 (d, J-8 Hz, 1H, H-24).

EXAMPLE 21

41) (5E, 7E,22E) - (1S,3R) -1,3 -Bis [[1,1-dimethylethyl(diphenyl)silyl]oxy]-24-hydroxy-20-methyl-9,10-secocholesta-5,7,10(19),22-tetraene-25-carboxylic acid ethyl ester 45

LDA is prepared from 180 mg (1.8 mmol) of diisopropylamine and 1.1 ml (1.7 mmol) of n-butyllithium (1.6M in hexane) in 30 ml of tetrahydrofuran under argon and cooled to −78° C. Now 200 mg (1.7 mmol) of isobutyric acid ethyl ester is added and stirred for 30 minutes at −78° C. and then 590 mg (0.68 mmol) of 44 in 3 ml of tetrahydrofuran is added. It is stirred for 2 hours more at −78° C. and then poured on sodium chloride solution. After extraction with ethyl acetate, washing of the organic phase with sodium chloride solution, drying on sodium sulfate and removal of the solvent, the residue is purified chromatographically and 180 mg of the title compound accumulates as colorless foam (1:1 diastereomers relative to C-24).

$^1$H-NMR(CDCl$_3$): δ=0.53 ppm (s, 3H, H-18); 0.95 (s, 18H, Si-t-butyl); 1.05/1.07, 1.10/1.12, 1.17, 1.18 (4x s; 3H, H-21, C-20-Me, H-26 and H-27 each); 1.28 (t, J=7Hz, 3H, COOEt); 2.57 (d, J=5 Hz, 1H, OH); 4.15 (q, J=7 Hz, 2H, COOEt); 4.18 (m, 1H, H-24); 4.28 (m, 1H, H-3); 4.63 (m, 1H, H-1); 4.72 and 4.90 (2x s; 1H, H-19 each); 5.32 (dd, J=15.5, 7.5 Hz, H-23); 5.89/5.90 (d, J=15.5 Hz, 1H, H-22); 5.60 and 6.38 (2x d, J=11 Hz; 1H, H-6 and H-7 each); 7.20–7.68 (m, 20H, Si-phenyl).

42) (5Z,7E,22E)-(1S,3R,24R)-20-Methyl-1,3,24-trihydroxy-9,10-secocholesta-5,7,10(19),22-tetraene-25carboxylic acid ethyl ester 46a and (5Z,7E,22E)(1S,3R,24S)-20-methyl-1,3,24-trihydroxy-9,10- secocholesta-5,7,10(19),22-tetraene-25-carboxylic acid ethyl ester 46b 480 mg (0.5 mmol) of 45 is stirred with 65 mg (0.77 mmol) of dihydropyran and a spatula tip full of pyridinium-p-toluene sulfonate in 5 ml of methylene chloride under argon for 24 hours at room temperature. The organic phase is washed with sodium chloride solution, dried on sodium sulfate, the solvent is removed and the residue is purified chromatographically on silica gel with hexane/ethyl acetate, and 480 mg of the diastereomer mixture remains as colorless foam. This product is dissolved in 80 ml of toluene and irridated in the presence of 100 mg (0.55 mmol) of anthracene and 0.1 ml of triethylamine in a pyrex immersion reactor with a mercury high-pressure lamp (Philips HPK 125) under nitrogen for 15 minutes. The solvent is removed and the crude product is stirred with 708 mg (2.25 mmol) of tetrabutylammonium fluoride in 10 ml of tetrahydrofuran under argon at 60° C. for 1 hour. Then it is poured in sodium chloride solution, extracted with ethyl acetate, washed with sodium chloride solution, dried on sodium sulfate and the solvent is removed. The residue is dissolved in 5 ml of methanol/methylene chloride (9:1) and stirred under argon with 500 mg of amberlite (activated) for 24 hours. It is now filtered, the filtrate is washed with sodium bicarbonate solution and sodium chloride solution, dried on sodium sulfate, the solvent is removed and the residue is purified chromatographically. The separation of the diastereomers now takes place via HPLC (reversed phase conditions, acetonitrile/water as mobile solvent, and 5 mg of 46b and 6 mg of 46a are obtained in succession as colorless foams.

$^1$H-NMR(CD$_2$Cl$_2$): 46a δ=0.58 ppm (s, 3H, H-18); 1.03, 1.07, 1.18 (3x, s, 3H, 3H, 6H, H-21, C-20-Me, H-26 and H-27); 1.27 (t, J=7Hz, 3H, COOEt); 4.10(m, 1H, H-24); 4.12 (q, J=7Hz, 2H, COOEt); 4.18 (m, 1H, H-3); 4.38 (m, 1H, H-I); 4.97 and 5.30 (2x s; 1H, H-19 each); 5.31 (dd, J=15.5, 7Hz, 1H, H-23); 5.86 (d, J=15.5 Hz, 1H, H-22); 5.99 and 6.35 (2x d, J=11 Hz; 1H, H-6 and H-7 each)

46b 6=0.58 ppm (s, 3H, H-18); 1.01, 1.09, 1.12 (3x, s, 3H, 3H, 6H, H-21, C-20-Me, H-26 and H-27); 1.27 (t, J=7Hz, 3H, COOEt); 4.10(m, 1H, H-24); 4.12 (q, J=7Hz, 2H, COOEt); 4.18 (m, 1H, H-3); 4.38 (m, 1H, H-I); 4.96 and 5.30 (2x s; 1H, H-19 each); 5.30 (dd, J=15.5, 7 Hz, 1H, H-23); 5.88 (d, J=15.5 Hz, 1H, H-22); 5.99 and 6.35 (2x d, J=11 Hz; 1H, H-6 and H-7 each).

EXAMPLE 22

43) (5E,7E,22E)-(1S,3R)-1,3-Bis[[1,1-dimethylethyl-(diphenyl)silyl]oxy]-24-hydroxy-20-methyl-9,10-secoc-holesta-5,7,10(19 ),22-tetraene-25-carboxylic acid propyl ester 47

Analogously to 41) 690 mg (0.8 mmol) of 44 is reacted with 2 mmol of LDA and 256 mg (2 mmol) of isobutyric acid propyl ester and 550 mg of the title compound accumulates as colorless foam (1:1 diastereomers relative to C-24).

¹H-NMR(CDCl₃): a =0.53 ppm (s, 3H, H-18); 0.95 (t, J=7 Hz, 3H, COOPr); 0.97 and 0.98 (2x s; 9H, Si-t-butyl each); 1.07/1.08, 1.10/1.12, 1.18 and 1.19 (4x s; 3H, H-21, C-20-Me, H-26 and H-27 each); 1.68 (hex, J=7Hz, 2H, COOPr); 2.53 (d, J=7 Hz, 1H, OH); 4.08 (q, J-7 Hz, 2H, COOPr); 4.15 (m, 1H, H-24); 4.28 (m, 1H, H-3); 4.62 (m, 1H, H-1); 4.72 and 4.89 (2x s; 1H, H-19 each); 5.33 (dd, J=15,5, 7Hz, H-23); 5.90/5.91 (d, J=15.5 Hz, 1H, H-22); 5.60 and 6.39 (2x d, J=11Hz; 1H, H-6 and H-7 each); 7.22–7.65 (m, 20H, Si-phenyl).

44) (5Z,7E,22E) - (1S,3R,24R) -20-Methyl-1,3,24-trihydroxy-9,10- secocholesta-5,7,10(19),22- tetraene-25-carboxylic acid propyl ester 48a and (5Z,7E,22E) (1S, 3R,24S)- 20-methyl-1,3,24-trihydroxy-9,10-secocholesta-5,7,10(19), 22-tetraene-25-carboxylic acid propyl ester 48b 540 mg (0.55 mmol) of 47 is reacted analogously to the conditions described in 42) and 34 mg of 48b and 24 mg of 48a are obtained as colorless foam.

¹H-NMR(CD₂Cl₂): 48a δ=0.58 ppm (s, 3H, H-18); 0.95 (t, J=7 Hz, 3H, COOPr); 1.04, 1.08, 1.22 (3x s, 3H, 6H, H-21, C-20-Me, H-26 and H-27); 1.67 (hex, J=7 Hz, 3H, COOPr); 4.02 (t, J=7 Hz, 2H, COOPr); 4.10(m, 1H, H-24); 4.18 (m, 1H, H-3); 4.38 (m, 1H, H-1); 4.96 and 5.29 (2x s; 1H, H-19 each); 5.31 (dd, J=15.5, 7 Hz, 1H, H-23); 5.86 (d, J=15.5 Hz, 1H, H-22); 6.00 and 6.36 (2x d, J=11 Hz; 1H, H-6 and H-7 each)

¹H-NMR(CD₂Cl₂): 48b δ=0.58 ppm (s, 3H, H-18); 0.95 (t, J=7 Hz, 3H, COOPr); 1.00, 1.09, 1.22 (3x s, 3H, 3H, 6H, H-21, C-20-Me, M-26 and M-27); 1.68 (hex, J=7 Hz, 3H, COOPr); 4.02 (t, J=7 Hz, 2H, COOPr); 4.10(m, 1H, H-24); 4.18 (m, 1H, H-3); 4.38 (m, 1H, H-1); 4.96 and 5.29 (2x s; 1H, H-19 each); 5.32 (dd, J=15.5, 7 Hz, 1H, H-23); 5.89 (d, J=15.5 Hz, 1H, H-22); 6.00 and 6.36 (2x d, J=11 Hz; 1H, H-6 and H-7 each)

EXAMPLE 23

45) (5E,7E,22E)-(1S,3R)-1,3-Bis[[1,1-dimethylethyl(diphenyl)silyl]oxy]-24-hydroxy-20-methyl-9,10-secocholesta-5,7,10(19),22-tetraene-25-carboxylic acid-1-methyl ester 49

Analogously to 41) 440 mg (0.51 mmol) of 44 is reacted with 1.7 mmol of LDA and 221 mg (1.7 mmol) of isobutyric acid propyl ester and 390 mg of the title compound is obtained as colorless foam (1:1 diastereomers relative to C-24).

¹H-NMR(CDCl₃): δ=0.53 ppm (s,3H,H-18); 0.95 and 0.97 (2x s; 9H, Si-t-butyl each); 1.05/1.07, 1.09/1.11, 1.17 and 1.18 (4x s; 3H, H-21, C-20-Me, H-26 and H-27 each); 1.28 (d, J=7 Hz, 6H, COOiPr); 4.12 (m, 1H, H-24); 4.28 (m, 1H, H-3); 4.64 (m, 1H, H-i); 4.72 and 4.90 (2x s; 1H, H-19 each); 5.24 (hept, J=7Hz, 1H, COOiPr); 5.33 (dd,J=15,5, 7Hz, H-23); 5.90/5.91 (d,J=15.5 Hz, 1H, H-22); 5.61 and 6.38 (2x d; J=11 Hz; 1H, H-6 and H-7 each); 7.22-7.65 (m, 20H, Si-phenyl).

46) (5Z,7E,22E)-(1S,3R,24R)-20-Methyl-1,3,24-trihydroxy-9,10-secocholesta-5,7,10(19),22-tetraene-25-carboxylic acid-1-methyl ethyl ester 50a and (5Z,7E,22E)-(1S,3R,24S ) -20-methyl-1,3,24-trihydroxy-9,10-secocholesta-5,7,10(19),22-tetraene-25-carboxylic acid-1-methyl ethyl ester 50b 385 mg (0.39 mmol) of 49 is reacted analogously to the conditions described in 42) and 12 mg of 50b and 11 mg of 50a are obtained as colorless foams.

¹H-NMR(CD₂Cl₂): 50a δ=0.58 ppm (s, 3H, H-18); 1.03, 1.06, 1.18 (3x s, 3H, 3H, 6H, H-21, C-20-Me, H-26 and H-27); 1.28 (d, J=7 Hz, 6H, COOiPr); 4.09 (m, 1H, H-24); 4.18 (m, 1H, H-3); 4.38 (m, 1H, H-1); 4.90 and 5.30 (2x s; 1H, H-19 each); 4.98 (hept, J=7 Hz, 1H, COOiPr); 5.31 (dd, J=15.5, 7 Hz, H-23); 5.85 (d, J=15.5 Hz, 1H, H-22); 5.99 and 6.36 (2x d, J=11 Hz; 1H, H-6 and H-7 each).

¹H-NMR(CD₂Cl₂) : δ=0.59 ppm (s, 3H, H-18); 1.02, 1.11, 1.18 (3x s, 3H, 3H, 6H, H-21, C-20-Me, H-26 and H-27); 1.27 (d, J=7 Hz, 6H, COOiPr); 4.09 (m, 1H, H-24); 4.18 (m, 1H, H-3); 4.38 (m, 1H, H-1); 4.96 and 5.30 (2x s; 1H, H-10 each); 4.99 (hept, J=7Hz, 1H, COOiPr); 5.31 (dd, J=15.5, 7 Hz, H-23); 5.88 (d, J=15.5 Hz, 1H, H-22); 6.00 and 6.36 (2x d, J=11Hz; 1H, H-6 and H-7 each). Initial materials in the 20-methyl series (tert.butyldimethylsilyl protective groups).

47) (5E, 7E) - (1S, 3R) -1,3-Bis[[dimethyl(1,1dimethylethyl)silyl]oxy]-20-formyl-20-methyl-9,10-secopregna-5, 7,10 (19)-triene 51

4.0 g of (7 mmol) of (5E, 7Z) - (1S, 3R, 20S) -1,3-bis [[dimethyl(1,1-dimethylethyl)silyl]oxy]-20-formyl-9,10-secopregna-5,7,10(19)-triene 1 (M. Calverley Tetrahedron 43, 4609 (1987), WO 87/00834) is reacted with 314 mg (10.5 mmol) of sodium hydride and 3.87 g (28 mmol) of methyliodide analogously to 38) and 3.1 g of the title compound is obtained as colorless foam.

¹H-NMR(CDCl₃): δ=0.00 ppm (s, 12H, SiMe); 0.50 (s, 3H, H-18); 0.80 and 0.85 (2x s; 9H, Si-t-butyl each); 1.06 and 1.08 (2x s; 3H, H-21 and C-20-Me each); 4.18 (m, 1H, H-3); 4.48 (m, 1H, H-1); 4.89 and 4.92 (2x s; 1H, H-19 each); 5.76 and 6.38 (2x d, J-11 Hz; 1H, H-6 and H-7); 9.59 (s, 1H, H-22).

48) (5E,7E,22E)-(1S,3R)-Bis[[dimethyl(1,1-dimethylethyl) silyl]oxy]-20,N-dimethyl-N-methoxy-9,10-secochola-5,7,10(19), 22 -tetraene-24-amide 52

3.1 g (5.3 mmol) of 51 is reacted with 15.4 g (42.4 mmol) of N-methoxy-N-methyl-2-(triphenylphosphoroanylidene) acetamide analogously to 39) and 1.3 g of the title compound is obtained as colorless foam in addition to 1.1 g of the initial material.

¹H-NMR(CDCl₃): δ=0.01 ppm (s, 12H, SiMe); 0.50 (s, 3H, H-18); 0.81 and 0.84 (2x s; 9H, Si-t-butyl each); 1.07 and 1.10 (2x s; 3H, H-21 and C-20-Me each); 3.19 (s, 3H, N-Me); 3.64 (s, 3H, N-OMe); 4.17 (m, 1H, H-3); 4.48 (m, 1H, H-1); 4.88 and 4.92 (2x s; 1H, H-19 each); 5.73 and 6.39 (2x d, J=11 Hz; 1H, H-6 and H-7 each); 6.23 (d,J=16 Hz, 1H, H-23); 7.11 (d,J=16 Hz, 1H, H-22).

49) (5E, 7E, 22E) - (1S, 3R) -1,3 -Bis[[dimethyl (1,1-dimethylethyl)silyl]oxy]-20-methyl-9,10-secochola-5,7, 10(19),22-tetraen-24-al 53

1.3 g (1.9 mmol) of 52 is reacted with 9.5 mmol of DIBAH solution in toluene analogously to 40) and 840 mg of the title compound is obtained as colorless foam.

¹H-NMR(CDCl₃): δ=0.02 ppm (s, 12H, SiMe); 0.50 (s, 3H, H-18); 0.83 and 0.87 (2x s; 9H, Si-t-butyl each); 1.09 and 1.14 (2x s; 3H, H-21 and C-20-Me each); 4.18 (m, 1H, H-3); 4.48 (m, 1H, H-1); 4.88 and 4.92 (2x s; 1H, H-19 each); 5.74 and 6.38 (2x d, J=11 Hz; 1H, H-6 and H-7 each); 3.99 (dd,J=15.8 Hz, 1 Hz, H-23); 6.98 (d, J=15 Hz, 1H, H-22); 9.48 (d, J=8 Hz, H-24).

EXAMPLE 24

50) (5E,7E,22E) - (1S,3R)-1,3-Bis[[dimethyl(1,1-dimethylethyl)silyl]oxy]-24-hydroxy-20-methyl-9,10-secocholesta-5,7,10(19),22-tetraene-25-carboxylic acid ethyl ester 54

Analogously to 41) 210 mg (0.34 mmol) of 53 is reacted with 1.4 mmol of LDA and 165 mg (1.4 mmol) of isobutyric acid ethyl ester and 180 mg of the title compound is obtained as colorless foam (1:1 diastereomers relative to C-24).

$^1$H-NMR(CDCl$_3$): δ=0.02 ppm (s, 12H, SiMe); 0.51 (s, 3H, H-18); 0.80 and 0.83 (2x s; 9H, Si-t-butyl each); 0.98/1.00, 1.02/1.06, 1.09, 1.10 (4x s; 3H, H-21, C-20-Me, H-26 and H-27 each); 1.23 (t, J=7 Hz, 3H, COOEr); 4.07 (m, 1H, H-24); 4.10 (q, J=7 Hz, 2H, COOEt); 4.15 (m, 1H, H-3); 4.48 (m, 1H, H-1); 4.88 and 4.92 (2x s; 1H, H-19 each); 5.27 (dd, J=15, 7 Hz, 1H, H-23); 5.82/5.83 (2x d, J=15 Hz, 1H, H-22); 5.73 and 6.39 (2x d, J=11 Hz; 1H, H-6 and H-7 each).

51) (5Z,7E,22E)-(1S,3R)-1,3-Dihydroxy-20-methyl-24-oxo-9,10-secocholesta-5,7,10(19),22-tetraene-25-carboxylic acid ethyl ester 55

210 mg (0.29 mmol) of 54 is dissolved in 80 ml of toluene, 80 mg (0.44 mmol) of anthracene and 3 drops of triethylamine are added and irridated in a pyrex-immersion reactor with a mercury high-pressure lamp (Philips HPK 125) under nitrogen for 15 minutes. The solvent is removed and the residue is purified chromatographically on silica gel with hexane/ethyl acetate, and 200 mg of isomerized product is obtained as colorless foam. This material is dissolved in 1 ml of methylene chloride and instilled at –50° C. in a mixture of 0.1 ml (1 mmol) of oxalyl chloride and 0.15 ml (2 mmol) of DMSO in 10 ml of methylene chloride. It is stirred for 13 minutes and then 0.65 ml (5 mmol) of triethylamine is added. After heating to room temperature, sodium chloride solution is added, it is extracted with ethyl acetate, washed with sodium chloride solution, dried on sodium sulfate and the solvent is removed. The crude product is now chromatographed on silica gel and 103 mg of oxidation product remains, which is stirred in 5 ml methylene chloride/methanol (1:9) with 500 mg of DOWEX (activated) for 3 days at room temperature. Then the ion exchanger is filtered off, the filtrate is concentrated by evaporation and purified chromatographically, and 38 mg of the title compound is obtained as colorless foam.

$^1$H-NMR(CD$_2$Cl$_2$): =δ 0.50 ppm (s, 3H, H-18); 1.04 and 1.10 (2x s; 3H, H-21 and C-20-Me each); 1.20 (t, J=7 Hz, 3H, COOEt); 1.33 (s, 6H, H-26 and H-27); 4.12 (q, J=7 Hz, 2H, COOEt); 4.15 (m, 1H, H-3); 4.38 (m, 1H, H-1); 4.93 and 5.29 (2x s; 1H, H-19 each); 5.98 and 6.32 (2x d, J=11 Hz; 1H, H-6 and H-7 each); 6.10 (d, J=15 Hz, 1H, H-23 ); 7.13 (d, J=15 Hz, 1H, H-22). Initial material in the 20-methylene series 52) (5E,7E)-(1S,3R,20R)-1,3-Bis[[1,1dimethylethyl (diphenyl)silyl]oxy]- 20,21-epoxy-20-methyl-9,10-secopregna-5,7,10(19)-triene 57

3.1 g (3.84 mmol) of (5E, 7E)-(1S, 3R)-1,3-bis[[1,1-dimethylethyl (diphenyl)silyl]oxy]- 9,10-secopregna-5,7,10(19)-trien-20-one 56 (bis-TBDMS ether see WO 90/09991, Leo Pharmaceutical Products) is dissolved in 70 ml of dimethylformamide under argon and mixed with 1.06 g (5.2 mmol) of trimethylsulfoniumiodide. It is cooled to 0° C. and 0.51 g (5.2 mmol) of potassium-tert.-butanolate is added in portions. After 15 minutes at 0° C. saturated sodium chloride solution is added, it is extracted with ethyl acetate and the organic phase is washed several times with sodium chloride solution. After drying on sodium sulfate the solvent is removed and the residue is purified on silica gel with hexane/ethyl acetate and 2.2 g of the title compound is obtained as colorless foam.

$^1$H-NMR(CDCl$_3$): δ=0.58 ppm (s, 3H, H-18); 0.89 and 0.94 (2x s; 9H, Si-t-butyl each); 1.32 (s, 3H, H-21); 2.31 and 2.50 (2x d, J=5 Hz; 1H, H-22 each); 4.19 (m, 1H, H-3); 4.59 (t, J=5.5 Hz, 1H, H-1); 4.70 and 4.82 (2x s; 1H, H-19 each); 5.57 and 6.31 (2x d, J=11 Hz; 1H, H-6 and H-7 each); 7.12–7.68 (m, 20H, Si-phenyl) .

53) (5E,7E)-(1S,3R)-1,3-Bis[[1,1-dimethylethyl (diphenyl)silyl]oxy]-20-methylene-9,10-secopregna-5,7,10(19)-trien-21-ol 58

0.28 g (3.8 mmol) of diethylamine is dissolved under argon in 35 ml of diethyl ether and 2.4 ml (3.8 mmol) of n-butyllithium solution (1.6M in hexane) is added at 0° C. After 30 minutes of stirring at this temperature 0.72 g (0.88 mmol) of 57 in 5 ml of diethylether is instilled and stirred for 1 hour at 0° C. and 1 hour at room temperature. Then it is mixed with sodium chloride solution, extracted with ethyl acetate and the organic phase is washed with sodium chloride solution. After drying on sodium sulfate it is concentrated by evaporation and the residue is chromatographed on silica gel with hexane/ethyl acetate and 360 mg of the title compound is obtained as colorless foam in addition to 280 mg of the initial product.

$^1$H-NMR(CDCl$_3$) : δ=0.45 ppm (s, 3H, H-18); 0.99 and 1.00 (2x s; 9H, Si-t-butyl each); 4.08 and 4.17 (2x d; J=14.5 Hz, 1H, H-22 each); 4.29 (m, 1H, H-3); 4.65 (m, 1H, H-1); 4.75 and 4.90 (2x s; 1H, H-19 each); 5.03 and 5.23 (2x s; 1H, H-21 each); 5.67 and 6.39 (2x d, J=11 Hz; 1H, H-6 and H-7 each); 7.20–7.62 (m, 20H, Si-phenyl).

54) (5Z,7E)-(1S,3R)-1,3-Bis[[1,1-dimethylethyl (diphenyl)silyl]oxy]-20-methylene-9,10-secopregna-5,7,10(19)-trien-21-ol 59

500 mg (0.61 mmol) of 58 is dissolved in 80 ml of toluene, mixed with 80 mg (0.44 mmol) of anthracene and 15 μl of triethylamine and irridated for 18 minutes in the apparatus described in 42). After working up and purification, 450 mg of the title compound is obtained as colorless foam.

$^1$H-NMR(CDCl$_3$): δ=0.43 ppm (s, 3H, H-18); 0.95 and 1.00 (2x s; 9H, Si-t-butyl each); 4.05 and 4.15 (2x d, J=14.5 Hz; 1H, H-22 each); 4.25 (m, 1H, H-3 ); 4.55 (m, 1H, H-1); 4.83 and 5.08 (2x s; 1H, H-19 each); 5.00 and 5.21 (2x s; 1H, H-21 each); 6.02 and 6.10 (2x d, J=11 Hz; 1H, H-6 and H-7 each); 7.15–7.68 (m, 20H, Si-phenyl) .

55) (5Z,7E)-(1S,3R)-1,3-Bis[[1,1dimethylethyl(diphenyl)silyl]oxy]-20-formyl-9,10-secopregna-5,7,10(19),20-tetraene 60

2.8 g (3.36 mmol) of 59 is dissolved in 100 ml of methylene chloride and 11.6 g (133 mmol) of manganese dioxide is added. It is stirred for 1 hour more at room temperature and then suctioned off on Celite. After removal of the solvent, 2.5 g of the title compound is obtained as colorless foam.

$^1$H-NMR(CDCl$_3$): δ=0.35 ppm (s, 3H, H-18); 0.92 and 0.99 (2x s; 9H, Si-t-butyl each); 4.23 (m, 1H, H-3); 4.55 (m, 1H, H-1; 4.83 and 5.10 (2x s; 1H, H-19 each); 6.02 and 6.09 (2x d, J=11 Hz; 1H, H-6 and H-7 each); 6.11 and 6.32 (2x, s; 1H, H-21 each); 7.23–7.69 (m, 20H, Si-phenyl); 9.58 (s, 1H, H-22).

56) (5Z,7E,22E)-(1S,3R)-1,3-Bis[[1,1-dimethylethyl (diphenyl)silyl]oxy]-N-methoxy-N-methyl-9,10-secochola-5,7,10(19),20,22-pentaene-24-amide 61

1.2 g (1.4 mmol) of 60 is reacted with 3.75 g (9 mmol) of N-methoxy-N-methyl-2(triphenylphosphoranylidene) acetamide analogously to 39 ) and 1.07 g of the title compound is obtained as colorless foam.

$^1$H-NMR(CDCl$_3$): δ=0.39 ppm (s, 3H, H-18); 0.93 and 0.99 (2x s; 9H, Si-t-butyl each); 3.28 (s, 3H, N-Me); 3.75 (s, 3H, N-OMe); 4.25 (m, 1H, H-3); 4.55 (m, 1H, H-1); 4.48 and 5.10 (2x s; 1H, H-19 each); 5.32 and 5.57 (2x s; 1H, H-21 each); 6.04 and 6.10 (d, J=11 Hz; 1H, H-6 and H-7 each); 6.65 (d, J=15.5 Hz, 1H, H-23); 7.23–7.70 (m, 21H, Si-phenyl and H-22).

57) (5Z,7E,22E)-(1S,3R)-1,3-Bis[[1,1-dimethylethyl (diphenyl)silyl]oxy]-9,10-secochola-5,7,10(19),20,22-pentaen-24-al 62

750 mg (0.8 mmol) of 61 is reacted with 4 mmol of DIBAH solution analogously to 40) and 500 mg of the title compound is obtained as colorless foam.

δ=0.40 (s, 3H, H-18), 0.92 and 1.00 (2x s, 9H, Si-t-butyl each); 4.22 (m, 1H, H-3); 4.56 (m, 1H, H-1); 4.82 and 5.10 (2x s; 1H, H-19 each); 5.51 and 5.68 (2x s; 1H, H-21 each); 6.02 and 6.10 (2x d, J=11 Hz; 1H, H-6 and H-7 each); 6.36 (dd, J=16 8 Hz, 1H, H-23); 7.18 (d, J=16 Hz, 1H, H-22); 7.22–7.68 (m, 20H, Si-phenyl); 9.60 (d, J=8 Hz, 1H, H-24).

EXAMPLE 25

58) (5Z,7E,22E)-(1S,3R,24R)-1,3-Bis[[1,1-dimethylethyl (diphenyl)silyl]oxy]-24-hydroxy-9,10-secocholesta-5,7,10 (19),20,22-pentaene-25-carboxylic acid-1-methyl ethyl ester 63a and (5Z,7E,22E)(1S,3R,24S)-1,3-bis[[1,1-dimethylethyl(diphenyl)silyl]oxy]-24-hydroxy-9,10-secocholesta-5,7,10(19),20,22-pentaene-25-carboxylic acid-1-methyl ethyl ester 63b LDA is prepared from 385 mg (3.8 mmol) of diisopropylamine and 2.2 ml (3.4 mmol) of n-butyllithium (1.6M in hexane) in 30 ml of tetrahydrofuran under argon and cooled to −78° C. 442 mg (3.4 mmol) of isobutyric isopropyl ester is now added, stirred for 30 minutes at −78° C. and then 650 mg (0.76 mmol) of 62 in 5 ml of tetrahydrofuran is added. It is stirred for 3 hours more at −78° C. and then poured on sodium chloride solution. After extraction with ethyl acetate, washing the organic phase with sodium chloride solution, drying on sodium sulfate and removing the solvent the residue is chromatographically separated and 207 mg of 63b and 160 mg of 63a are obtained in succession as colorless foams.

$^1$H-NMR(CD$_2$Cl$_2$): 63a: =δ0.37 ppm (s, 3H, H-18); 0.94 and 0.96 (2x s; 9H, Si-t-butyl each); 1.13 and 1.14 (2x s; 3H, H-26 and H-27 each); 1.22 (d, J=7 Hz, 6H, COOiPr); 4.14 (m, 1H, H-24); 4.24 (m, 1H, H-3); 4.54 (m, 1H, H-1); 4.81 and 5.17 (2x s; 1H, H-19 each); 4.98 (hept, J=7 Hz, 1H, COOiPr); 4.99 and 5.07 (2x s; 1H, H-21 each); 5.78 (dd, J=15.5 6 Hz, H-23); 6.02 and 6.12 (2x d, J=11Hz; 1H, H-6 and H-7 each); 6.24 (d, J=15.5 Hz, 1H, H-22); 7.22–7.65 (m, 20H, Si-phenyl);

$^1$H-NMR(CD$_2$Cl$_2$): 63b: =δ0.37 ppm (s, 3H, H-18); 0.94 and 0.96 (2x s; 9H, Si-t-butyl each); 1.15 and 1.18 (2x s; 3H, H-26 and H-27 each); 1.23 (d, J=7 Hz, 6H, COOiPr); 4.14 (m, 1H, H-24); 4.24 (m, 1H, H-3); 4.54 (m, 1H, H-1); 4.82 and 5.19 (2x s; 1H, H-19 each); 4.99 (hept, J=7 Hz, 1H, COOiPr); 5.00 and 5.08 (2x s; 1H, H-21 each); 5.80 (dd, J=15.5 6 Hz, H-23 ); 6.02 and 6.12 (2x d; J=11 Hz, 1H, H-6 and H-7 each); 6.28 (d, J=15.5 Hz, 1H, H-22); 7.22-7.65 (m, 20H, Si-phenyl).

59) (5Z,7E,22E)-(1S,3R,24R)-1,3,24-Trihydroxy-9,10-secocholesta-5,7,10(19),20,22-pentaene-25-carboxylic acid-1-methylethyl ester 64a 160 mg (0.16 mmol) of 63a is stirred with 162 mg (1.6 mmol) of dihydropyran and a spatula tip full of pyridinium-p-toluene sulfonate in 5 ml of methylene chloride under argon for 24 hours at room temperature. Then it is washed with sodium chloride solution, dried on sodium sulfate, the solvent is removed and the residue is chromatographically purified. The thus obtained diastereomeric mixture is dissolved in 20 ml of tetrahydrofuran and stirred with 408 mg (1.3 mmol) of tetrabutylammonium fluoride at 60° C. under argon. It is poured on sodium chloride solution, extracted with ethyl acetate, washed with sodium chloride solution and concentrated by evaporation. The residue is now stirred with 420 mg of Amberlite (activated) in 5 ml of methanol/methylene chloride (9:1) at room temperature. Then it is filtered, the filtrate is washed with sodium bicarbonate solution and sodium chloride solution, dried on sodium sulfate and the solvent is removed. The crude product is purified chromatographically on silica gel with hexane/ethyl acetate and 23 mg of the title compound is obtained as colorless foam.

$^1$H-NMR(CD$_2$Cl$_2$): =δ0.42 ppm (s, 3H, H-18); 1.11 and 1.12 (2x s; 3H, H-26 and H-27 each); 1.22 (d, J=7 Hz, 6H, COOiPr); 4.15 (m, 2H, H-3 and H-24); 4.37 (m, 1H, H-1); 4.95 and 5.30 (2x s; 1H, H-19 each); 4.97 (hept, J=7 Hz, 1H, COOiPr); 5.00 and 5.17 (2x s; 1H, H-21 each); 5.78 (dd, J=15.5, 6 Hz, H-23); 6.03 and 6.34 (2x d, J=11 Hz; 1H, H-6 and H-7 each); 6.22 (d, J=15.5 Hz, 1H, H-22).

60) (5Z,7E,22E) - (1S,3R,24S) -1,3,24-Trihydroxy-9,10-secocholesta-5,7,10 (19),20,22-pentaene-25-carboxylic acid-1-methylethyl ester 64b 207 mg (0.21 mmol) of 63b is reacted analogously to 59) and 28 mg of the title compound is obtained as colorless foam.

$^1$H-NMR(CD$_2$Cl$_2$): =δ0.42 ppm (s, 3H, H-18); 1.12 and 1.15 (2x s; 3H, H-26 and H-27 each); 1.22 (d, J=7 Hz, 6H, COOiPr); 4.14 (m, 2H, H-3 and H-24); 4.36 (m, 1H, H-1); 4.95 and 5.30 (2x s; 1H, H-19 each); 4.96 (hept, J=7 Hz, 1H, COOiPr); 4.98 and 5.16 (2x s; 1H, H-21 each); 5.80 (dd, J=15.5, 6 Hz, H-23); 6.03 and 6.34 (2x d, J=11 Hz; 1H, H-6 and H-7 each); 6.25 (d, J=15.5 Hz, 1H, H-22).

EXAMPLE 26

61) (5Z, 7E, 22E) - (1S, 3R, 24R)-1,3-Bis[[1,1-dimethylethyl (diphenyl)silyl]oxy]-24-hydroxy-9,10 -secocholesta-5,7,10(19),20,22-pentaene-25-carboxylic acid methyl ethyl ester 65a and (5Z,7E,22E)-(1S,3R,24S)-1,3-bis[[1,1-dimethylethyl(diphenyl)silyl]oxy]-24-hydroxy-9, 10-secocholesta-5,7,10(19),20,22-pentaene-25-carboxylic acid methyl ethyl ester 65b 400 mg (0.47 mmol) of 62 is reacted analogously to 58) with 1.2 mmol of LDA and 0.18 ml (1.18 mmol) of isobutyric acid methyl ester and after separation of the diastereomers on HPLC ( standard phase, methylene chloride/methanol) 134 mg of 65a and 128 mg of 65b are obtained as colorless foams.

$^1$H-NMR(CDCl$_3$): 65a: =δ0.36 ppm (s, 3H, H-18); 0.92 and 0.95 (2x s; 9H, Si-t-butyl each); 1.14 (s 6, H-26 and H-27); 2.48 (d, J=5 Hz, 1H, OH); 3.66 (s, 3H, COOMe); 4.16 (dd, J=6.5 Hz, 1H, H-24); 4.24 (m, 1H, H-3); 4.53 (m, 1H, H-1); 4.81 and 5.18 (2x s; 1H, H-19 each); 4.99 and 5.06 (2x s; 1H, H-21 each); 5.77 (dd, J=15.5 6 Hz, H-23); 6.02 and 6.12 (2x d, J=11 Hz; 1H, H-6 and H-7 each); 6.24 (d, J=15.5 Hz, 1H, H-22); 7.21–7.66 (m, 20H, Si-phenyl);

$^1$H-NMR(CDCl$_3$): 65b: =δ 0.36 ppm (s, 3H, H-18); 0.93 and 0.96 (2x s; 9H, Si-t-butyl each); 1.15 (s 6, H-26 and H-27); 2.48 (d, J=5Hz, 1H, OH); 3.65 (s, 3H, COOMe); 4.17 (dd, J=6.5 Hz, 1H, H-24); 4.24 (m, 1H, H-3); 4.53 (m, 1H, H-i); 4.82 and 5.18 (2x s; 1H, H-19 each); 4.99 and 5.06 (2x s; 1H, H-21 each); 5.79 (dd, J=15.5 6 Hz, H-23 ); 6.02 and 6.12 (2x d, J=11 Hz; 1H, H-6 and H-7 each); 6.27 (d, J=15.5 Hz, 1H, H-22); 7.23-7.70 (m, 20H, Si-phenyl).

62) (5Z,7E,22E) - (1S,3R,24R) -1,3,24-Trihydroxy-9,10-secocholesta-5,7,10(19),20,22-pentaene-25-carboxylic acid methylethyl ester 66a 134 mg (0.14 mmol) of 65a is reacted analogously to 59) and 14 mg of the title compound is obtained as colorless foam.

$^1$H-NMR(CD$_2$Cl$_2$): =δ 0.43 ppm (s, 3H, H-18); 1.17 (s, 6H, H-26 and H-27); 2.52 (d, J=6 Hz, 1H, OH); 3.68 (s, 3H, COOMe); 4.17 (dd, J=7, 6 Hz, 1H, H-24); 4.17 (m, 1H, H-3); 4.38 (m, 1H, H-1); 4.97 and 5.30 (2x s; 1H, H-19 each); 5.01 and 5.20 (2x s, 1H, H-21 each); 5.77 (dd, J=15.5, 6 Hz, 1H, H-23); 6.03 and 6.36 (2x d, J=11 Hz; 1H, H-6 and H-7 each); 6.25 (d, J=15.5 Hz, 1H, H-22).

63) (5Z,7E,22E) - (1S,3R,24S) -1,3,24-Trihydroxy-9,10-secocholesta-5,7,10(19),20,22-pentaene-25-carboxylic acid methylethyl ester 66b 128 mg (0.13 mmol) of 65b is reacted analogously to 59) and 19 mg of the title compound is obtained as colorless foam.

$^1$H-NMR(CD$_2$Cl$_2$) : =δ0.44 ppm (s, 3H, H-18); 1.15 and 1.16 (2x s; 3H, H-26 and H-27 each); 2.48 (d, J=6 Hz, 1H, OH); 3.66 (s, 3H, COOMe); 4.18 (dd, J=7, 6 Hz, 1H, H-24); 4.17 (m, 1H, H-3); 4.37 (m, 1H, H-1); 4.90 and 5.31 (2x s; 1H, H-19 each); 5.00 and 5.18 (2x s; 1H, H-21 each); 5.79 (dd, J=15.5 Hz, 6 Hz, 1H, H-23); 6.04 and 6.36 (2x d, J=11 Hz; 1H, H-6 and H-7 each); 6.28 (d, J=15.5 Hz, 1H, H-22)

EXAMPLE 27

64) (5Z,7E,22E)-(1S,3R,24R)-1,3-Bis[[1,1-dimethylethyl (diphenyl)silyl]oxy]-24-hydroxy-9,10-secocholesta-5,7, 10(19),20,22-pentaene-25-carboxylic acid ethyl ethyl ester 67a and (5Z,7E,22E)-(1S,3R,24S)-1,3-bis [[1,1-dimethyl-ethyl(diphenyl)silyl]oxy]-24-hydroxy-9,10-secocholesta-5, 7,10(19),20,22-pentaene-25-carboxylic acid ethyl ethyl ester 67b 400 mg (0.47 mmol) of 62 is reacted analogously to 58) with 1.2 mmol of LDA and 0.16 ml (1.18 mmol) of isobutyric ethyl ester and after separation of the diastereomers on HPLC ( standard phase, methylene chloride/methanol) 105 mg of 67a and 90 mg of 67b are obtained as colorless foam.

$^1$H-NMR(CDCl$_3$) : 67a: =δ 0.38 ppm (s, 3H, H-18); 0.95 and 1.00 (2x s; 9H, Si-t-butyl each); 1.20 (s 6, H-26 and H-27); 1.29 (t, J=7 Hz, 3H, COOEt); 4.18 (q, J=7 Hz, 2H, COOEt); 4.20 (m, 2H, H-3 and H-24); 4.54 (m, 1H, H-1); 4.83 and 5.20 (2x s; 1H, H-19 each); 5.01 and 5.09 (2x s, 1H, H-21 each); 5.80 (dd, J=15.5 Hz, 6 Hz,1H, H-23); 6.02 and 6.09 (2x d, J=11 Hz; 1H, H-6 and H-7 each); 6.29 (d, J=15.5 Hz, 1H, H-22); 7.20-7.65 (m, 20H, Si-phenyl)

$^1$H-NMR(CDCl$_3$): 67b: =67 0.39 ppm (s, 3H, H-18); 0.94 and 1.00 (2x s; 9H, Si-t-butyl each); 1.18 and 1.22 (2x s 3H, H-26 and H-27); 1.28 (t, J=7 Hz, 3H, COOEt); 4.18 (q, J=7 Hz, 2H, COOEt); 4.21 (m, 2H, H-3 and H-24); 4.54 (m, 1H, H-1); 4.83 and 5.20 (2x s; 1H, H-19 each); 5.00 and 5.08 (2x s; 1H, H-21 each); 5.82 (dd, J=15.5 Hz, 6 Hz,1H, H-23); 6.02 and 6.10 (2x d, J=11 Hz; 1H, H-6 and H-7 each); 6.30 (d, J=15.5 Hz, 1H, H-22); 7.20–7.65 (m, 20H, Si-phenyl).

65) (5Z,7E,22E) - (1S,3R,24R) -1,3,24-Trihydroxy-9,10-secocholesta-5,7,10(19),20,22-pentaene-25-carboxylic acid ethyl ester 68a 100 mg (0.11 mmol) of 67a is reacted analogously to 59) and 15 mg of the title compound is obtained as colorless foam.

$^1$H-NMR(CD$_2$Cl$_2$): =δ 0.43 ppm (s, 3H, H-18); 1.15 (s, 6H, H-26 and H-27); 1.22 (t, J=7 Hz, 3H, COOEr); 4.10 (q, J=7 Hz, 2H, COOEt); 4.18 (m, 2H, H-3 and H-24); 4.39 (m, 1H, H-1); 4.98 and 5.30 (2x s; 1H, H-19 each); 5.01 and 5.20 (2x s; 1H, H-21 each); 5.78 (dd, J=15.5, 6 Hz, 1H, H-23); 6.03 and 6.37 (2x d, J=11 Hz; 1H, H-6 and H-7 each); 6.25 (d, J=15.5 Hz, 1H, H-22) .

66) (5Z,7E,22E) - (1S,3R,24S) -1,3,24-Trihydroxy-9,10-secocholesta-5,7,10(19),20,22-pentaene-25-carboxylic acid ethyl ester 68b 89 mg (0.11 mmol) of 67b is reacted analogously to 59) and 13 mg of the title compound is obtained as colorless foam.

$^1$H-NMR(CD$_2$Cl$_2$): =δ 0.43 ppm (s, 3H, H-18); 1.17 and 1.18 (2x s, 3H, H-26 and H-27 each); 1.23 (t, J=7 Hz, 3H, COOEr); 4.11 (q, J-7 Hz, 2H, COOEr); 4.18 (m, 2H, H-3 and H-24); 4.38 (m, 1H, H-1); 4.97 and 5.30 (2x s; 1H, H-19 each); 4.99 and 5.20 (2x s; 1H, H-31 each); 5.80 (dd, J-15.5, 6 Hz, 1H, H-23); 6.04 and 6.35 (2x d, J=11 Hz; 1H, H-6 and H-7 each); 6.28 (d, J=15.5 Hz, 1H, H-22).

Initial materials in the 19-Nor series with standard configuration in 20 position 67) [1R-[1a[R*-(E)],3aβ,4α,7aα]]-N-methoxy-4-[4-(methoxymethoxy)-7a-methyl-octahydro-1H -inden-1-yl]-N-methyl-2-pentene amide 70

10.0 g (39.3 mmol) of [1R-[1α(S*),3aβ,4α,7aα]]-α-7a-dimethyl-4-(methoxymethoxy)octahydro-1H-inden-1-acetaldehyde 69 [H. H. Inhoffen et al. Chem. Ber. 91, 780 (1958), Chem. Ber. 92, 1772 (1959), W. G. Dauben et al. Tetrahedron Lett. 30, 677 (1989)] is reacted with 41.9 g (117.8 mmol) of N-methoxy-N-methyl-(2-triphenylphosphoranylidene)acetamide analogously to 39) and 10.6 g of the title compound is obtained as colorless oil.

1H-NMR(CDCl$_3$): =δ 0.89 ppm (s, 3H, H-18); 1.03 (d, J-7 Hz, 3H, H-21); 3.19 (s, 3H, N-Me); 3.30 (s, 3H, OMe); 3.65 (s, 3H, N-OMe): 3.80 (m, 1H, H-8); 4.48 and 4.60 (2x d, J=6 Hz; 1H, OCH$_2$O each); 6.28 (d, J-15 Hz, 1H, H-23); 6.78 (d, J=15.9 Hz, 1H, H-22).

68) [1R-[1α[R*-(E)],3aβ,4α,7aα]]-4-(4-hydroxy-7a-methyloctahydro-1H-inden-1-yl)-N-methoxy-N-methyl-2-pentene amide 71

5.3 g ( 15.6 mmol ) of 70 in mixed in 250 ml of THF with 4.45 g (23.5 mmol) of p-toluenesulfonic acid and stirred overnight at 70° C. After cooling sodium chloride solution is added and it is extracted with ethyl acetate. The organic phase is washed with sodium bicarbonate solution and sodium chloride solution, dried on sodium sulfate and the solvent is removed. The residue is purified by chromatography on silica gel with hexane/ethyl acetate and 3.08 g of the title compound is obtained as colorless oil.

$^1$H-NMR(CDCl$_3$): =δ 0.99 ppm (s, 3H, H-18); 1.08 (d, J-7 Hz, 3H, H-21); 3.22 (s, 3H, N-Me); 3.70 (s, 3H, N-OMe); 4.08 (m, 1H, H-8); 6.30 (d, J=15 Hz, 1H, H-23); 6.81 (dd, J=15.9 Hz, 1H, H-22) .

69) [1R-[1α[R*-(E)],3aβ,7aα]]-N-methoxy-N-methyl-4-(7a-methyl-4-oxooctohydro-4H-inden-1-yl)-2-pentene amide 72

3.08 g (10.5 mmol) of 71 is stirred in 150 ml of methylene chloride with 3.16 g (14.7 mmol) of pyridiniumchlorochromate for 2 hours. Then it is diluted with diethyl ether, filtered on Celite, the solvent is removed and the residue is chromatographed on silica gel with hexane/ethyl acetate and 2.07 g of the title compound remains as colorless oil.

1H-NMR(CDCl$_3$): =δ 0.69 ppm (s, 3H, H-18); 1.13 (s, 3H, H-21); 2.48 (dd, J=10.5, 7.5 Hz, 1H, H-14); 3.23 (s, 3H, N-Me); 3.70 (s, 3H, N-OMe); 6.33 (d, J=15 Hz, 1H, H-23); 6.81 (dd, J=15.9 Hz, 1H, H-22).

70) (7E,22E)-(1R,3R)-1,3-Bis[[dimethyl(1,1dimethylethyl) silyl]oxy]-N-methoxy-N-methyl-19-nor-9,10-secochola-5,7,22-triene-24-amide 73

1.5 g (2.63 mmol) of (3R-trans) - [2-[3,5-bis[[dimethyl (1,1-dimethylethyl)silyl]oxy]- cyclohexylidene]-ethyl] diphenylphosphine oxide [H. F. DeLuca et al. Tetrahedron Lett. 32, 7663 (1991)] is dissolved in 15 ml of THF and cooled under argon to −70° C. 1.94 ml (3.16 mmol) of n-butyllithium solution (1.6 M in hexane) is now instilled. After 5 minutes 696 mg (2.39 mmol) of 72 in 15 ml of THF is now instilled and stirred for 30 minutes at this temperature. Then it is hydrolyzed with potassium sodium tartrate/ potassium bicarbonate solution, extracted with ethyl acetate, the organic phase is washed with sodium chloride solution, dried on sodium sulfate and the solvent is removed. The residue is chromatographed on silica gel with hexane/ethyl acetate and 390 mg of the title compound is obtained as colorless foam.

$^1$H-NMR (CDCl$_3$): δ=0.03 and 0.06 ppm (2x s; 6H, SiMe each); 0.58 (s, 3H, H-18); 0.86 and 0.87 (2x s; 3H, Si-t-butyl each); 1.13 (d, J=7 Hz, 3H, H-21); 3.23 (s, 3H, N-Me); 3.70 (s, 3H, N-OMe); 4.08 (m, 2H, H-1 and H-3); 5.81 and 6.17 (2x d, J=11 Hz; 1H, H-6 and H-7 each); 6.32 (d, J=15 Hz, 1H, H-23); 6.85 (dd, J=15.9 Hz, 1H, H-22).

71) (7E, 22E) - (1R, 3R) -1,3-Bis[[dimethyl (1,1-dimethylethyl)silyl]oxy]-19-nor-9,10-secochola-5,7,22-trien-24-al 74

380 mg (0.59 mmol) of 73 is reacted with 1.48 mmol of DIBAH solution analogously to 40) and 305 mg of the title compound is obtained as colorless foam.

$^1$H-NMR (CDCl$_3$): δ =0.05 and 0.06 ppm (2x s; 6H, SiMe each); 0.60 (s, 3H, H-18); 0.87 and 0.88 (2x s; 3H, Si-t-butyl each); 1.17 (d, J=7 Hz, 3H, H-12); 4.08 (m, 2H, H-1 and H-3); 5.82 and 6.17 (2x d, J=11 Hz; 1H, H-6 and H-7 each); 6.07 (dd, J=15, 7 Hz, 1H, H-23 ); 6.72 (dd, J=15, 9 Hz, 1H, H-22); 9.49 (d, J=7 Hz, 1H, H-24).

EXAMPLE 28

72) (7E, 22E) - (1R,3R,24R)-1,3-Bis[[dimethyl (1,1-dimethylethyl)silyl]oxy]-24-hydroxy-19-nor-9,10-secocholesta-5,7,22-triene-25-carboxylic acid-1-methylethyl ester 75a and (7E,22E) - (1R,3R,24S) -1,3-bis [[dimethyl(1,1-dimethylethyl)silyl]oxy]-24-hydroxy-19-nor-9,10 -secocholesta-5, 7,22-triene-25-carboxylic acid-1-methylethyl ester 75b Analogously to 41) 305 m9 (0.52 mmol) of 74 is reacted with 2.1 mmol of LDA and 0.28 ml (2.07 mmol) of isobutyric acid isopropyl ester and after purification on HPLC (standard phase, mobile solvent: methylene chloride/ methanol) 62 mg of 75a and 115 mg of 75b are obtained as colorless foams.

$^1$H-NMR(CD$_2$Cl$_2$): 75a: =δ =0.02 ppm (s, 12H, SiMe); 0.51 (s, 3H, H-18); 0.82 and 0.83 (2x s; 9H, Si-t-butyl each); 1.01 (d, J=7 Hz, 3H, H-21); 1.08 and 1.09 (2x s; 3H, H-26 and H-27 each); 1.20 (d, J=7 Hz, 6H, COOiPr); 2.45 (d, J=6 Hz, 1H, OH); 4.02 (m, 3H, H-1, H-3 and H-24); 4.96 (hept. J=7 Hz, 1H, COOiPr); 5.31 (dd, J=15, 7 Hz, 1H, H-23); 5.48 (dd, J=15, 9 Hz, 1H, H-22); 5.78 and 6.12 (2x d, J=11 Hz; 1H, H-6 and H-7 each).

$^1$H-NMR(CD$_2$Cl$_2$): 75b: =δ =0.02 ppm (s, 12H, SiMe); 0.50 (s, 3H, H-18); 0.82 and 0.83 (2x s; 9H, Si-t-butyl each); 1.00 (d, J=7 Hz, 3H, H-21); 1.07 and 1.08 (2x s; 3H, H-26 and H-27 each); 1.19 (d, J=7 Hz, 6H, COOiPr); 4.02 (m, 3H, H-I, H-3 and H-24); 4.93 (hept. J=7 Hz, 1H, COOiPr); 5.33 (dd, J=15, 7 Hz, 1H, H-23 ); 5.52 (dd, J=15, 9 Hz, 1H, H-22); 5.78 and 6.13 (2x d, J=11 Hz; 1H, H-6 and H-7 each).

73) (7E,22E) - (1R,3R,24R) -1,3,24-Trihydroxy-19-nor-9,10-secocholesta-5,7,22-triene-25 -carboxylic acid-1-methylethyl ester 76a 59 mg (0.082 mmol) of 75a is stirred with 600 mg of Dowex in 6 ml of methanol/methylene chloride 9:1 for 3 days. After filtration the solvent is removed and the residue is chromatographed on silica gel with hexane/ethyl acetate and 22 mg of the title compound is obtained as colorless foam.

$^1$H-NMR(CD$_2$Cl$_2$): δ=0.58 ppm (s, 3H, H-18); 1.03 (d, J=7 Hz, 3H, H-21); 1.11 and 1.12 (2x s; 3H, H-26 and H-27 each); 1.22 (d, J=7 Hz, 6H, COOiPr); 2.51 (d, J=6 Hz, 1H, OH); 4.02 (m, 3H, H-1, H-3 and H-24); 4.98 (hept. J=7 Hz, 1H, COOiPr); 5.35 (dd, J=15, 7 Hz, 1H, H-23); 5.51 (dd, J=15, 9 Hz, 1H, H-22); 5.84 and 6.28 (2x d, J=11 Hz; 1H, H- 6 and H- 7 each) .

74) (7E,22E) - (1R,3R,24S)-1,3,24-Trihydroxy-19-nor-9, 10-secocholesta-5,7,22-triene-25-carboxylic acid-1-methylethyl ester 76b 112 mg (0.156 mmol) of 75a is reacted analogously to 73) and 81 mg of the title compound is obtained as colorless foam.

$^1$H-NMR(CD$_2$Cl$_2$): δ=0.57 ppm (s, 3H, H-18); 1.03 (d, o J=7 Hz, 3H, H-21); 1.12 and 1.13 (2x s; 3H, H-26 and H-27 each); 1.22 (d, J=7 Hz, 6H, COOiPr); 2.50 (d, J=6 Hz, 1H, OH); 4.02 (m, 3H, H-1, H-3 and H-24); 4.98 (hept. J=7 Hz, 1H, COOiPr); 5.38 (dd, J=15, 7 Hz, 1H, H-23); 5.57 (dd, J=15, 9 Hz, 1H, H-22); 5.84 and 6.28 (2x d, J=11 Hz; 1H, H-6 and H-7 each) .

EXAMPLE 29

75) (7E,22E)-(1R,3R,24R)-1,3-Bis[[dimethyl(1,1-dimethylethyl)silyl]oxy]-24-hydroxy-19-nor-9,10-secocholesta-5,7,22-triene-25-carboxylic acid ethyl ester 77a and (7E, 22E) - (1R,3R,24S)-1,3-bis[[dimethyl(1,1-dimethylethyl)silyl]oxy]-24-hydroxy-19-nor-9,10-secocholesta-5,7,22-triene-25-carboxylic acid ethyl ester 77b Analogously to 41) 280 mg (0.48 mmol) of 74 is reacted with 2 mmol of LDA and 0.26 mg (1.9 mmol) of isobutyric acid ethyl ester and purified analogously to 72) and 58 mg of 77a and 86 mg of 77b are obtained as colorless foams.

$^1$H-NMR(CD$_2$Cl$_2$): 77a: δ=0.02 ppm (s, 12H, SiMe); 5 0.51 (s, 3H, H-18); 0.82 and 0.84 (2x s; 9H, Si-t-butyl each); 1.02 (d, J=7 Hz, 3H, H-21); 1.08 and 1.09 (2x s; 3H, H-26 and H-27 each); 1.27 (t, J=7 Hz, 3H, COOEt); 2.46 (d, J=6 Hz, 1H, OH); 4.02 (m, 3H, H-1, H-3 and H-24); 4.05 (q, J=7 Hz, 2H, COOEr); 5.32 (dd, J=15, 7 Hz, 1H, H-23); 5.49 (dd, J=15, 9 Hz, 1H, H-22); 5.78 and 6.12 (2x d, J=11 Hz; 1H, H-6 and H-7 each).

$^1$H-NMR(CD$_2$Cl$_2$): 77b: =δ=0.02 ppm (s, 12H, SiMe); 0.51 (s, 3H, H-18); 0.82 and 0.83 (2x s; 9H, Si-t-butyl each); 1.01 (d, J=7 Hz, 3H, H-21); 1.07 and 1.08 (2x s; 3H, H-26 and H-27 each); 1.28 (t, J=7 Hz, 3H, COOEt); 4.02 (m, 3H, H-1, H-3 and H-24); 4.05 (q, J=7 Hz, 2H, COOEt); 5.34 (dd, J=15, 7 Hz, 1H, H-23); 5.54 (dd, J=15, 9 Hz, 1H, H-22); 5.78 and 6.13 (2x d, J=11 Hz; 1H, H-6 and H-7 each).

76) (7E,22E)-(1R,3R,24R)-1,3,24-Trihydroxy-19-nor-9, 10-secocholesta-5,7,22-triene-25-carboxylic acid ethyl ester 78a 58 mg (0.082 mmol) of 77a is reacted analogously to 73) and 20 mg of the title compound is obtained as colorless foam.

$^1$H-NMR(CD2C12): δ=0.57 ppm (s, 3H, H-18); 1.04 (d, J=7 Hz, 3H, H-21); 1.11 and 1.12 (2x s; 3H, H-26 and H-27 each); 1.29 (t, J=7 Hz, 6H, COOEr); 2.53 (d, J=6 Hz, 1H, OH); 4.03 (m, 3H, H-1, H-3 and H-24); 4.07 (q, J=7 Hz, 2H, COOEt); 5.36 (dd, J=15, 7 Hz, 1H, H-23); 5.52 (dd, J=15, 1H, H-22); 5.85 and 6.28 (2x d; J=11 Hz, 1H, H-6 and H-7 each) .

77) (7E,22E) - (1R,3R,24S)-1,3,24-Trihydroxy-19-nor-9,10-secocholesta-5,7,22-triene-25-carboxylic acid ethyl ester 78b 72 mg (0.102 mmol) of 77b is reacted analogously to 73) and 51 mg of the title compound is obtained as colorless foam.

$^1$H-NMR(CD$_2$Cl$_2$): δ=0.58 ppm (s, 3H, H-18); 1.04 (d, J=7 Hz, 3H, H-21); 1.12 and 1.13 (2x s; 3H, H-26 and H-27 each); 1.28 (t, J=7 Hz, 6H, COOEr); 2.52 (d, J=6 Hz, 1H, OH); 4.03 (m, 3H, H-1, H-3 and H-24); 4.06 (q, J=7 Hz, 2H, COOEr); 5.39 (dd, J=15, 7 Hz, 1H, H-23); 5.58 (dd, J=15, 1H, H-22); 5.85 and 6.28 (2x d, J=11 Hz; 1H, H-6 and H-7 each).

EXAMPLE 30

78) (7E,22E)-(1R,3R)-1,3-Bis[[dimethyl(1,1dimethylethyl)silyl]oxy]-24-oxo-19-nor-9,10-secocholesta-5,7,22-triene-25-carboxylic acid ethyl ester 79

0.04 ml (0.4 mmol) of oxalyl chloride in 5 ml of methylene chloride is introduced at −50° C., 0.06 ml (0.8 mmol) of DMSO in 1 ml of methylene chloride is instilled and stirred for 2 minutes. Then 80 mg (0.11 mmol) of a 75a/75b mixture in 1 ml of methylene chloride is instilled. After 15 minutes 0.26 ml of triethylamine is then added at −50° C. and the reaction mixture is allowed come to room temperature. It is hydrolyzed with sodium chloride solution, extracted with ethyl acetate, washed with sodium chloride solution, dried on sodium sulfate and the solvent is removed. The residue is chromatographed on silica gel with hexane/ethyl acetate and 51 mg of the title compound remains as colorless foam.

$^1$H-NMR(CD$_2$Cl$_2$): δ=0.01 and 0.05 ppm (2x s; 6H, SiMe each); 0.51 (s, 3H, H-18); 0.83 (s; 18H, Si-t-butyl each); 1.05 (d, J=7 Hz, 3H, H-21); 1.18 (d, J=7 Hz, 6H, COOiPr); 1.29 (s; 6H, H-26 and H-27 each); 4.05 (m, 2H, H-I, H-3); 4.98 (hept. J=7 Hz, 1H, COOiPr); 5.78 and 6.11 (2x d, J=11 Hz; 1H, H-6 and H-7 each); 6.10 (J=15 Hz, 1H, H-23); 6.77 (dd, J=15, 9.5 Hz, 1H, H-22).

79) (7E,22E) - (1R,3R)-1,3-Dihydroxy-24-oxo-19-nor-9,10-secocholesta-5,7,22-triene-25-carboxylic acid-1-methylethyl ester 80

48 mg (0.067 mmol) of 79 is reacted analogously to 73) and 19 mg of the title compound is obtained as colorless foam.

$^1$H-NMR(CD$_2$Cl$_2$): δ=0.51 ppm (s, 3H, H-18); 1.08 (d, J=7 Hz, 3H, H-21); 1.20 (d, J=7 Hz, 6H, COOiPr); 1.31 (s, 6H, H-26 and H-27 each); 3.98 and 4.08 (2x m; 1H, H-1 and H-3 each); 5.00 (hept. J=7 Hz, 1H, COOiPr); 5.83 and 6.28 (2x d, J=11 Hz; 1H, H-6 and H-7 each); 6.15 (J=15 Hz, 1H, H-23); 6.80 (dd, J=15, 9.5 Hz, 1H, H-22).

Initial materials in the 19-Nor-series with 20 modifications

80) [1S- (1α,3aβ,4α,7aα)]-1-[4-(Methoxymethoxy)-7a-methyloctahydro-1H-inden-1-yl]-1-ethanone 81

12.2 g (47.9 mmol) of [1R-[1α(S$^*$),3aβ,4α,7aα]]-α,7a-dimethyl-4-(methoxymethoxy)octahydro-1H-inden-1-acetaldehyde 69 [H. H. Inhoffen et al. Chem. Ber. 91, 780 (1958), Chem. Ber. 92, 1772 (1959), W. G. Dauben et al. Tetrahedron Lett. 30, 677 (1989)] in 600 ml of DMF is stirred with 4.78 g (41.9 mmol) of DABCO, 720 mg (3.6 mmol) of copper(II) acetate and 574 mg (3.6 mmol) of bipyridyl with air introduction at 70° C. for 24 hours. After cooling of the mixture it is mixed with sodium chloride solution, extracted with ethyl acetate and the organic phase is washed thoroughly with sodium chloride solution. It is dried on sodium sulfate, the solvent is removed and the residue is purified chromatographically on silica gel with hexane/ethyl acetate and 7.1 g of the title compound remains as colorless oil.

$^1$H-NMR(CDCl$_3$): δ=0.82 ppm (s, 3H, H-18); 2.10 (s, 3H, H-21); 2.49 (t, J=9 Hz, 1H, H-17); 3.34 (s, 3H, OMe); 4.52 and 4.63 (2x d; J=6 Hz, 1H, OCH$_2$O each).

81) [1S-[1α(R)$^*$, 3aβ,4α,7aα)]-1-[4-(Methoxymethoxy)-7a-methyloctahydro-1H-inden-1-yl]-1-methyloxirane 82

6.1 g (25.38 mmol) of 8.1 is reacted analogously to 52) and 6.4 g of the title compound is obtained as colorless oil.

$^1$H-NMR (CDCl$_3$): δ=1.03 ppm (s, 3H, H-18); 1.38 (s, 3H, H-21); 2.31 and 2.50 (2x d; J=5 Hz, 1H, H-22 each); 3.35 (s, 3H, OMe); 3.85 (m, 1H, H-8); 4.54 and 4.64 (2x d, J=6 Hz; 1H, OCH$_2$O each).

82) [1S-(1α,3aβ,4α,7aα)]-4-(Methoxymethoxy)-7a-methyl-β-methyleneoctahydro-1H-inden-1-ethanol 83

12.1 g (47 mmol) of 82 and 19.03 g (94 mmol) of aluminum isopropylate is dissolved in 400 ml of toluene and heated for 3 hours to boiling. After cooling it is stirred with isopropanol/water and then separated by filtration of the precipitated aluminum salts. The solvent is removed and the residue purified by chromatography on silica gel with hexane/ethyl acetate and 11.5 g of the title compound is obtained as colorless oil.

$^1$H-NMR(CDCl$_3$): δ=0.80 ppm (s, 3H, H-18); 3.37 (s, 3H, OMe); 3.89 (m, 1H, H-8); 4.00 and 4.10 (dbr, J=14 Hz; 1H, H-22 each); 4.56 and 4.65 (2x d, J=6 Hz; 1H, OCH$_2$O each); 4.94 and 5.21 (2x s; 1H, H-21 each).

83) [1S-(1α,3aα,4α,7aα)]-2-[4-(Methoxymethoxy)-7a-methyloctahydro-1H- inden-1-yl]-2-propenal 84

12.0 (47 mmol) of 83 is reacted analogously to 55) and 7.87 g of the title compound is obtained as colorless oil.

$^1$H-NMR(CDCl$_3$) : δ=0.76 ppm (s, 3H, H-18); 2.78 (t, J=9.5 Hz, H-17); 3.37 (s, 3H, OMe); 3.90 (m, 1H, H-8); 4.55 and 4.66 (2x d, J=6 Hz; 1H, OCH$_2$O each); 6.12 and 6.28 (2x s; 1H, H-21 each); 9.54 (s, 1H, H-22).

84) [1R-[1α(E),3aβ,4α,7aα]]-N-Methoxy-4-[4-(methoxymethoxy)-7a-methyloctahydro-1H -inden-1-yl]-N-methyl-2,4-pentadiene amide 85

6.6 (31.06 mmol) of 84 is reacted with 22.5 g (71.6 mmol) of N-methoxy-N-methyl-(2-triphenylphosphoroanylidine)acetamide analogously to 39) and 6.8 g of the title compound is obtained as colorless oil.

$^1$H-NMR(CDCl$_3$) : δ=0.70 ppm (s, 3H, H-18); 2.41 (t, J=10 Hz, H-17); 3.20 (s, 3H, N-Me); 3.30 (s, 3H, OMe); 3.64 (s, 3H, N-OMe); 3.84 (m, 1H, H-8); 4.49 and 4.60 (2x d, J=6 Hz; 1H, OCH20 each); 5.22 and 5.51 (2x s; 1H, H-21 each); 6.53 (d, J=15 Hz, 1H, H-23); 7.30 (d, J=15 Hz, 1H, H-22).

85) [1R-[1α(E), 3aβ,4α,7aα]]-4-(4-Hydroxy-7a-methyloctahydro-1H-inden-1-yl)-N-methoxy-N-methyl-2,4-pentadiene amide 86

17.5 (5.19 mmol) of 85 is reacted analogously to 68) and 806 mg of the title compound is obtained as colorless oil.

¹H-NMR(CDCl₃): δ=0.75 ppm (s, 3H, H-18); 2.42 (t, J=10 Hz, H-17); 3.20 (s, 3H, N-Me); 3.65 (s, 3H, N-OMe); 4.05 (m, 1H, H-8); 5.20 and 5.52 (s; 1H, H-21 each); 6.53 (d, J=15 Hz, 1H, H-23); 7.30 (d, J=15 Hz, 1H, H-22).

86) [1R- [1α(E),3β,7aα]]-N-Methoxy-N-methyl-4-(7a-methyl-4-oxooctahydro-4H-inden-1-yl)-2,4-pentadiene amide 87

800 mg of 86 is reacted analogously to 69) and 640 mg of the title compound is obtained as colorless oil.

¹H-NMR(CDCl₃): δ=0.52 ppm (s, 3H, H-18); 2.67 (dd, J=10.5, 7.5 Hz, 1H, H-14); 2.80 (t, J=10.5Hz, 1H, H-17); 3.29 (s, 3H, N-Me); 3.74 (s, 3H, N-OMe); 5.32 and 5.60 (2x s; 1H, H-21 each); 6.65 (d, J=15Hz, 1H, H-23); 7.38 (d, J=15Hz, 1H, H-22).

87) (7E,22E) - (1R,3R) -1,3-Bis[[dimethyl(1,1-dimethylethyl)silyl]oxy]-N-methyl-N-methoxy-19-nor-9,10-secochola-5,7,20,22-tetraene-25-amide 88

640 mg (2.2 mmol) of 87 is reacted analogously to 70) and 275 mg of the title compound is obtained as colorless foam.

¹H-NMR(CDCl₃): δ=0.05 ppm (s, 12H, SiMe); 0.43 (s, 3H, H-18); 0.88 and 0.89 (2x s; 9H, Si-t-butyl each); 3.28 (s, 3H, N-Me); 3.73 (s, 3H, N-OMe); 4.08 (m, 2H, H-1 and H-3); 5.33 and 5.55 (2x s; 1H, H-21 each); 5.85 and 6.18 (2x d, J=11 Hz; 1H, H-6 and H-7 each); 6.63 (d, J=15 Hz, 1H, H-23); 7.39 (d, J=15 Hz, 1H, H-22).

88) (7E, 22E) - (1R, 3R) -1,3 -Bis [[dimethyl(1,1-dimethylethyl) silyl]oxy]-19-nor-9,10-secochola-5,7,20,22 -tetraen-24-al 89

265 mg (0.41 mmol) of 88 is reacted with 1.03 mmol of DIBAH solution analogously to 40) and 220 mg of the title compound is obtained as colorless foam.

¹H-NMR(CDCl₃): δ=0.04 ppm (s, 12H, SiMe); 0.43 (s, 3H, H-18); 0.87 (s, 18H, Si-t-butyl); 4.09 (m, 2H, H-1 and H-3); 5.51 and 5.68 (2x s; 1H, H-21 each); 5.85 and 6.15 (2x d; J=11 Hz; 1H, H-6 and H-7 each); 6.34 (dd, J=15, 7.5 Hz, 1H, H-23); 7.18 (d, J=15 Hz, 1H, H-22); 9.58 (d, J=7.5 Hz, 1H, H-24).

EXAMPLE 31

89) (7E,22E) - (1R,3R,24R)-1,3-Bis [[dimethyl (1,1-dimethylethyl) silyl]oxy]-24-hydroxy-19-nor-9,10-secocholesta-5,7,20,22-tetraene-25-carboxylic acid-1-methyl-ethyl ester 90a and (7E,22E) - (1R,3R,24S)-1,3-bis [[dimethyl(1,1-dimethylethyl)silyl]oxy]-24-hydroxy-19-nor-9,10-secocholesta-5,7,20,22 -tetraene-25-carboxylic acid-1-methylethyl ester 90b Analogously to 41) 305 mg (0.52 mmol) of 89 is reacted with 2.1 mmol of LDA and 0.28 ml (2.07 mmol) of isobutyric acid isopropyl ester and after purification on HPLC (standard phase, mobile solvent: methylene chloride/methanol) 64 mg of 90a and 67 mg of 90b are obtained as colorless foams.

¹H-NMR(CD₂Cl₂) : 90a: =δ=0.05 ppm (s, 12H, SiMe); 0.41 (s, 3H, H-18); 0.85 and 0.86 (2x s; 9H, Si-t-butyl each); 1.14 and 1.15 (2x s; 6H, H-26 and H-27 each); 1.22 (d, J=7 Hz, 6H, COOiPr); 2.61 (d, J=6 Hz, 1H, OH); 4.07 (m, 2H, H-1 and H-3); 4.13 (dd, J=7, 6 Hz, 1H, H-24); 4.98 (hept. J=7 Hz, 1H, COOiPr); 5.01 and 5.20 (2x s; 1H, H-21 each); 5.84 and 6.16 (2x d, J=11 Hz; 1H H-6 and H-7 each); 5.76 (dd, J=15, 7 Hz, 1H, H-23); 6.12 (d, J=15 Hz, 1H, H-22).

¹H-NMR(CD₂Cl₂): 90b: =δ=0.05 ppm (s, 12H, SiMe); 0.41 (s, 3H, H-18); 0.86 (s; 18H, Si-t-butyl each); 1.14 and 1.16 (2x s; 3H, H-26 and H-27 each); 1.20 (d, J=7 Hz, 6H, C00iPr); 2.62 (d, J=7 Hz, 1H, OH); 4.08 (m, 2H, H-1 and H-3); 4.18 (t, J=7 Hz, 1H, H-24); 4.98 (hept. J=7 Hz, 1H, COOiPr); 4.99 and 5.19 (2x s; 1H, H-21 each); 5.84 and 6.17 (2x d, J=11 Hz; 1H H-6 and H-7 each); 5.80 (dd, J=15, 7 Hz, 1H, H-23); 6.26 (d, J=15 Hz, 1H, H-22).

90) (7E,22E) - (1R,3R,24R) -1,3,24-Trihydroxy-19-nor-9,10-secocholesta-5,7,20,22-tetraene-25-carboxylic acid-1-methyl ethyl ester 91a 64 mg (0.09 mmol) of 90a is reacted analogously to 73) and 22 mg of the title compound is obtained as colorless foam.

¹H-NMR(CD₂Cl₂) : δ=0.42 ppm (s, 3H, H-18); 1.14 and 1.15 (2x s; 3H, H-26 and H-27 each); 1.22 (d, J=7 Hz, 6H, COOiPr); 3.98 and 4.08 (2x m; 1H, H-1 and H-3 each); 4.15 (d, J=7 Hz, 1H, H-24); 4.98 (hept. J=7 Hz, 1H, COOiPr); 5.00 and 5.20 (2x s; 1H, H-21 each); 5.88 and 6.28 (2x d, J=11 Hz; 1H H-6 and H-7 each); 5.79 (dd, J=15, 7 Hz, 1H, H-23); 6.26 (d, J=15 Hz, 1H, H-22).

91) (7E,22E) - (1R,3R,24S) -1,3,24-Trihydroxy-19-nor-9,10-secocholesta-5,7,20,22-tetraene-25-carboxylic acid-1-methyl ethyl ester 91b 67 mg (0.09 mmol) of 90b is reacted analogously to 73) and 27 mg of the title compound is obtained as colorless foam.

¹H-NMR(CD₂Cl₂): δ=0.42 ppm (s, 3H, H-18); 1.14 and 1.17 (2x s; 3H, H-26 and H-27 each); 1.22 (d, J=7 Hz, 6H, COOiPr); 3.98 and 4.07 (2x m; 1H, H-1 and H-3 each); 4.18 (d, J=7 Hz, 1H, H-24); 4.99 (hept. J=7 Hz, 1H, COOiPr); 5.00 and 5.20 (2x s; 1H, H-21 each); 5.88 and 6.28 (2x d, J=11 Hz; 1H H-6 and H-7 each); 5.80 (dd, J=15, 7 Hz, 1H, H-23); 6.28 (d, J=15 Hz, 1H, H-22).

EXAMPLE 32

92) (7E,22E) - (1R,3R,24R)-1,3-Bis[[dimethyl(1,1dimethylethyl)silyl]oxy]-24-hydroxy-19-nor-9,10 -secocholesta-5,7,20,22-tetraene-25-carboxylic acid ethyl ester 92a and (7E,22E) - (1R,3R,24S) -1,3-bis [[dimethyl (1,1-dimethylethyl)silyl]oxy]-24-hydroxy-19-nor-9,10-secocholesta-5,7,20,22-tetraene-25-carboxylic acid ethyl ester 92b Analogously to 41) 300 mg (0.51 mmol) of 89 is reacted with 2 mmol of LDA and 0.26 ml (1.9 mmol) of isobutyric acid isopropyl ester and after purification on HPLC (standard phase, mobile solvent: methylene chloride/methanol) 68 mg of 92a and 85 mg of 92b are obtained as colorless foam.

¹H-NMR(CD₂Cl₂): 92a: =δ=0.04 ppm (s, 12H, SiMe); 0.40 (s, 3H, H-18); 0.84 and 0.86 (2x s; 9H, Si-t-butyl each); 1.13 and 1.14 (2x s; 6H, H-26 and H-27 each); 1.27 (t, J=7 Hz, 3H, COOEt); 2.59 (d, J=6 Hz, 1H, OH); 4.05 (m, 2H, H-1 and H-3); 4.11 (dd, J=7, 6 Hz, 1H, H-24); 4.12 (q, J=7 Hz, 1H, COOEr); 5.01 and 5.19 ( 2x s; 1H, H - 21 each); 5.84 and 6.16 (2x d, J=11 Hz; 1H, H-6 and H-7 each); 5.75 (dd, J=15, 7 Hz, 1H, H-23); 6.20 (d, J=15 Hz, 1H, H-22).

¹H-NMR(CD₂Cl₂): 92b: =δ=0.04 ppm (s, 12H, SiMe); 0.40 (s, 3H, H-18); 0.85 (s; 18H, Si-t-butyl each); 1.13 and 1.15 (2x s; 6H, H-26 and H-27 each); 1.28 (t, J=7 Hz, 3H, COOEt); 2.60 (d, J=7 Hz, 1H, OH); 4.06 (m, 2H, H-1 and H-3); 4.12 (dd, J=7 Hz, 2H, COOEr); 4.14 (q, J=7 Hz, 2H, COOEt); 4.99 and 5.18 (2x s, 1H, H-21 each); 5.84 and 6.16 (2x d, J=11 Hz; 1H, H-6 and H-7 each); 5.80 (dd, J=15, 7 Hz, 1H, H-23); 6.25 (d, J=15 Hz, 1H, H-22).

93) (7E,22E)-(1R,3R,24R)-1,3,24-Trihydroxy-19-nor9, 10-secocholesta-5,7,20,22-tetraene-25-carboxylic acid ethyl ester 93a 65 mg (0.093 mmol) of 93a is reacted analogously to 73) and 23 mg of the title compound is obtained as colorless foam.

$^1$H-NMR(CD$_2$Cl2): δ=0.41 ppm (s, 3H, H-18); 1.13 and 1.15 (2x s; 3H, H-26 and H-27 each); 1.26 (t, J=7 Hz, 6H, COOEt); 3.98 and 4.07 (2x m; 1H, H-1 and H-3 each); 4.14 (q, J=7 Hz, 2H, COOEt); 4.15 (d, J=7 Hz, 1H, H-24); 5.00 and 5.20 (2x s; 1H, H-21 each); 5.87 and 6.28 (2x d, J=11 Hz; 1H H-6 and H-7 each); 5.78 (dd, J=15, 7 Hz, 1H, H-23); 6.25 (d, J=15 Hz, 1H, H-22).

94) (7E, 22E) - (1R, 3R, 24S) -1,3,24-Trihydroxy-19-nor-9,10 -secocholesta-5,7,20,22-tetraene-25-carboxylic acid ethyl ester 93b 80 mg (0.14 mmol) of 92b is reacted analogously to 73) and 31 mg of the title compound is obtained as colorless foam.

$^1$H-NMR(CD$_2$Cl$_2$): δ=0.41 ppm (s, 3H, H-18); 1.14 and 1.16 (2x s; 3H, H-26 and H-27 each); 1.28 (t, J=7 Hz, 6H, COOEr); 3.98 and 4.06 (2x m; 1H, H-1 and H-3 each); 4.15 (q, J=7 Hz, 2H, COOEt); 4.17 (d, J=7 Hz, 1H, H-24); 5.00 and 5.19 (2x s; 1H, H-21 each); 5.87 and 6.28 (2x d, J=11 Hz; 1H H-6 and H-7 each); 5.80 (dd, J=15, 7 Hz, 1H, H-23); 6.28 (d, J=15 Hz, 1H, H-22).

Initial materials in the 20-fluoro-19-nor series

95) [1S- (1α,3aβ,4α,7aα)]-4-[[Dimethyl(1,1-dimethylethyl)silyl]oxy]-7a-methyl-1-[1-methyl-2-[(trimethylsilyl)oxy]-1-ethenyl]octahydro-1H-indene 95

To 37.7 g (170 mmol) of trimethylsilyltrifluoromethanesulfonate in 270 ml of methylene chloride, 21.9 g (170 mmol) of diisopropylethylamine at room temperature, and, at 5° C., 9 g (27 mmol) of [1R-[1α(S*), 3aβ,4α,7aα]] -α,7a-dimethyl-4-[[dimethyl(1,1-dimethylethyl)silyl]oxy]-octahydro-1H-inden-1-acetaldehyde 94 [H. H. Inhoffen et al. Chem. Ber. 91, 780 (1958), Chem. Ber. 92, 1772 (1959), W. G. Dauben et al. Tetrahedron Lett. 30, 677 (1989)] are instilled in 600 ml of methylene chloride. It is stirred for one hour at room temperature and the solvent is then removed in a vacuum. The residue is taken up in hexane, filtered on sodium sulfate and freed again from the solvent and 13 g of the title compound is obtained as colorless oil (E/Z mixture approximately 3:1).

$^1$H-NMR(CD$_2$Cl$_2$): δ=0.00 ppm (s, 6H, SiMe); 0.13 ppm (s, 9H, SiMe); 0.78 (s, 3H, H-18); 0.88 (s, 9H, Si-t-butyl); 1.50/1.57 (sbr, 3H, H-21); 4.02 (m, 1H, H-8); 6.02/6.18 (m, 1H, H-22).

96) l1S-[1α(S*), 3aβ,4α,7aα]]-α,7a-Dimethyl-4-[[dimethyl(1,1-dimethylethyl)silyl]oxy]-α-fluoroctahydro-1H-inden-1-acetaldehyde 96 and [1S-[1α(R*),3aβ,4α,7aα]]-α, 7a-dimethyl-4-[[dimethyl(1,1-dimethylethyl)silyl]oxy]-α-fluoroctahydro-1H-inden-1-acetaldehyde 97

15 g (37.81 mmol) of 95 is dissolved in 300 ml of methylene chloride and 26 g (82 mmol) of N-fluorodiphenylsulfonimide is instilled in 250 ml of methylene chloride at 5° C. It is stirred overnight at room temperature. Then the reaction mixture is poured in water, the organic phase is separated, dried on sodium sulfate, concentrated by evaporation and the residue is chromatographed on silica gel with hexane/ethyl acetate and 3.85 g of 9.6 and 2.08 g of 97 are obtained as colorless oil.

$^1$H-NMR (CDCl$_3$): 96: δ=0.00 and 0.01 ppm (2x s; 3H, SiMe each); 0.88 (s, 9H, Si-t-butyl); 1.02 (d, J=2 Hz, 3H, H-18); 1.42 (d, J=21 Hz, 3H, H-21); 4.01 (m, 1H, H-8); 9.75 (d, J=7 Hz, 1H, H-22).

97:6 δ=0.00 ppm (s; 6H, SiMe each); 0.88 (s, 9H, Si-t-butyl); 1.08 (d, J=4.5 Hz, 3H, H-18); 1.46 (d, J=21 Hz, 3H, H-21); 4.01 (m, 1H, H-8); 9.87 (d, J=6 Hz, 1H, H-22).

Initial materials in the 20-β-fluorine series

97) [1S-[1α[R*-(E)],3aβ,4α,7aα]]-4-[4-[Dimethyl (1,1dimethylethyl)silyl]oxy]-7a-methyl-octahydro-1H-inden-1-yl]-4-fluoro-N-methoxy-N-methyl-2-pentene amide 98

342 mg (1 mmol) of 96 is reacted analogously to 39) and 380 mg of the title compound is obtained as colorless oil.

$^1$H-NMR(CDCl$_3$) : δ=0.00 and 0.01 ppm (2x s; 3H, SiMe each); 0.88 (s, 9H, Si-t-butyl); 1.05 (d, J=2 Hz, 3H, H-18); 1.50 (d, J=21 Hz, 3H, H-21); 3.27 (s, 3H, N-Me); 3.70 (s, 3H, N-OMe); 4.01 (m, 1H, H-8); 6.55 (d, J=15.5 Hz, 1H, H-23); 6.93 (d, J=15.5 Hz, 1H, H-22).

98) [1S-[1α[R*-(E)],3aβ,4α,7aα]]-4-Fluoro-4-(4-hydroxy-7a -methyloctahydro-1H-inden-1-yl)-N-methoxy-N-methyl -2-pentene amide 99

100 mg (0.23 mmol) of 98 in 1.9 ml of acetonitrile and 1.5 ml of THF is stirred with 1.4 ml of hydrofluoric acid (40%) for 90 minutes. Then it is poured on sodium chloride solution, extracted with ethyl acetate, the organic phase is washed with sodium bicarbonate solution and sodium chloride solution, dried on sodium sulfate and concentrated by evaporation. The residue is purified chromatographically on silica gel with hexane/ethyl acetate and 53 mg of the title compound is obtained as colorless oil.

$^1$H-NMR(CDCl$_3$): δ=1.08 ppm (d, J=2 Hz, 3H, H-18); 1.50 (d, J=21 Hz, 3H, H-21); 3.25 (s, 3H, N-Me); 3.68 (s, 3H, N-OMe); 4.07 (m, 1H, H-8); 6.54 (d, J=15.5 Hz, 1H, H-23); 6.89 (dd, J=21, 15.5 Hz, 1H, H-22).

99) [1S-[1α[R*-(E)],3aβ,7aα]]-4-Fluoro-N-methoxy-N-methyl-4-(7a-methyl-4-oxo-octahydro-4H-inden-1-yl)-2-pentene amide 100

427 mg (1.36 mmol) of 99 is dissolved in 12 ml of methylene chloride, 63 mg (0.76 mmol) of sodium acetate is added and it is cooled to 0° C. Then it is mixed with 414 mg (1.92 mmol) of pyridinium chlorochromate and stirred for 3 hours at room temperature. After dilution with diethylether, it is filtered on Celite, concentrated by evaporation and chromatographed on silica gel with hexane/ethyl acetate and 357 mg of the title compound is obtained.

$^1$H-NMR(CDCl$_3$): δ=0.77 ppm (d, J=2 Hz, 3H, H-18); 1.53 (d, J=21 Hz, 3H, H-21); 2.46 (dd, J=10.5, 7.5 Hz, 1H, H-14); 3.26 (s, 3H, N-Me); 3.72 (s, 3H, N-OMe); 6.56 (d, J=15.5 Hz, 1H, H-23); 6.93 (dd, J=21, 15.5 Hz, 1H, H-22).

100) (7E,22E) - (1R,3R,20S)-1,3-Bis[[dimethyl (1,1-dimethylethyl)silyl]oxy]-20-fluoro-N-methoxy-N-methyl-19-nor-9,10-secochola-5,7,22-triene-24-amide 101

350 mg (1.15 mmol) of 100 is reacted analogously to 70) and 460 mg of the title compound is obtained as colorless foam.

$^1$H-NMR(CDCl$_3$): δ=0.03 ppm (s, 12H, SiMe); 0.62 (d, J=2 Hz, 3H, H-18); 0.81 and 0.82 (2x s; 9H, Si-t-butyl each); 1.50 (d, J=21 Hz, 3H, H-21); 3.22 (s, 3H, N-Me); 3.68 (s, 3H, N-OMe); 4.03 (m, 2H, H-1 and H-3); 5.77 and 6.11 (2x d, J=11 Hz; 1H H-6 and H-7 each); 6.53 (d, J=15.5 Hz, 1H, H-23); 6.90 (dd, J=21, 15.5 Hz, 1H, H-22).

101) (7E,22E)-(1R,3R,20S)-1,3-Bis[[dimethyl(1,1-dimethylethyl)silyl]oxy]-20-fluoro-19-nor-9,10-secochola-5,7,22-trien-24-al 102

440 mg (0.66 mmol) of 101 is reacted with 3.3 mmol of DIBAH solution analogously to 3. and 340 mg of the title compound is obtained as colorless foam.

$^1$H-NMR(CDCl$_3$) : δ=0.02 ppm (s, 12H, SiMe); 0.62 (d, J=2 Hz, 3H, H-18); 0.83 and 0.84 (2x s; 9H, Si-t-butyl each); 1.52 (d, J=21 Hz, 3H, H-21); 4.03 (m, 2H, H-1 and H-3); 5.78 and 6.11 (2x d, J=11 Hz; 1H H-6 and H-7 each); 6.22 (d, J=15.5, 8 Hz, 1H, H-23); 6.78 (dd, J=21, 15.5 Hz, 1H, H-22); 9.54 (dbr., J=8 Hz, 1H, H-24).

EXAMPLE 33

102) (7E,22E) - (1R,3R,20S)-1,3-Bis[[dimethyl(1,1-dimethylethyl)silyl]oxy]-20-fluoro-24-hydroxy-19-nor-9,10- secocholesta-5,7,22-triene-25-carboxylic acid ethyl ester 103

Analogously to 41) 700 mg (1.15 mmol) of 102 is reacted with 7.8 mmol of LDA and 1.2 ml (7.8 mmol) of isobutyric acid ethyl ester and 200 mg of the title compound is obtained as colorless foam (1:1 diastereomers relative to C-24).

$^1$H-NMR(CDCl$_3$): δ=0.02 ppm (s, 12H, SiMe); 0.62 (d, J=2 Hz, 3H, H-18); 0.83 and 0.84 (2x s; 9H, Si-t-butyl each); 1.12/1.16 and 1.21/1.16 (2x s; 3H, H-26 and H-27 each); 1.22 (t, J=7 Hz, 3H, COOEr); 1.47 (d, J=21 Hz, 3H, H-21); 4.04 (m, 1H, H-24); 4.13 (q, J-7 Hz, 2H, COOEt); 4.13 (m, 1H, H-24); 5.61 (d, J=15.5, 7 Hz, 1H, H-23); 5.75/5.78 (dd, J=21, 15.5 Hz, 1H, H-22); 5.78 and 6.12 (2x d, J=11 Hz; 1H, H-6 and H-7 each).

103) (7E,22E) - (1R,3R,20S) -20-Fluoro-1,3,24-trihydroxy-19-nor-9,10-secocholesta-5,7,22-triene-25-carboxylic acid ethyl ester 104

150 mg (0.2 mmol) of 103 in 20 ml of THF is stirred with 630 mg (2 mmol) of tetrabutylammoniumfluoride overnight at room temperature and then heated for 30 minutes to 40° C. After cooling sodium chloride solution is added, extracted with ethyl acetate, washed with sodium chloride solution, dried on sodium sulfate and concentrated by evaporation. The residue is chromatographed several times on silica gel with hexane/ethyl acetate and 17.3 mg of the title compound is obtained as colorless foam (1:1 diastereomers relative to C-24).

$^1$H-NMR(CD$_2$Cl$_2$): δ=0.60 ppm (d, J=2 Hz, 3H, H-18); 1.07 and 1.09/1.12 (2x s; 3H, H-26 and H-27 each); 1.18 (t, J=7 Hz, 3H, COOEt); 1.40 (d, J=21 Hz, 3H, H-21); 3.99 (m, 2H, H-1 and H-3); 4.05 (q, J-7 Hz, 2H, COOEt); 4.08 (m, 1H, H-24); 5.55/5.56 (dd, J=15.5, 7 Hz, 1H, H-23); 5.71 and 5.72 (dd, J=21, 15.5 Hz, 1H, H-22); 5.78 and 6.20 (2x d, J=11 Hz; 1H, H-6 and H-7 each). Initial materials in the 20-α-fluorine series 104) [1S-[1α[S-(E)],3aβ,4α,7aα]]-4-[4-[[Dimethyl(1,1-dimethylethyl)silyl]oxy]-7a-methyl -octahydro-1H-inden-1-yl]-4-fluoro-N-methoxy-N-methyl-2-pentene amide 105

2.03 g (5.9 mmol) of 97 is reacted analogously to 39) and 2.4 g of the title compound is obtained as colorless oil.

$^1$H-NMR(CDCl$_3$): δ=0.06 ppm (s, 6H, SiMe); 0.88 (s, 9H, Si-t-butyl); 1.00 (d, J=4.5 Hz, 3H, H-18); 1.40 (d, J=21 Hz, 3H, H-21); 3.29 (s, 3H, N-Me); 3.72 (s, 3H, N-OMe); 4.01 (m, 1H, H-8); 6.62 (d, J=15.5 Hz, 1H, H-23); 6.99 (d, J=15.5 Hz, 1H, H-22).

105) [1S- [1α[S*-(E)],3aβ,4α,7aα]]-4-Fluoro-4-(4-hydroxy-7a -methyloctahydro-1H-inden-1-yl)-N-methoxy-N-methyl-2-pentene amide 106

2.4 g (5.6 mmol) of 105 is reacted analogously to 98) and 1 g of the title compound is obtained as colorless oil.

$^1$H-NMR(CDCl$_3$) : δ=0.97 ppm (d, J=4.5 Hz, 3H, H-18); 1.40 (d, J=21 Hz, 3H, H-21); 3.25 (s, 3H, N-Me); 3.72 (s, 3H, N-OMe); 4.02 (m, 1H, H-8); 6.57 (d, J=15.5 Hz, H-23); 6.92 (d, J=25 Hz, 15.5 Hz, 1H, H-22).

106) [1S-[1α[S*-(E)],3aβ,7aα]]-4-Fluoro-N-methoxy-N-methyl-4-(7a-methyl-4-oxo-octahydro-4H-inden-1-yl)-2-pentene amide 107

1 g (3.19 mmol) of 106 is reacted analogously to 99) and 800 mg of the title compound is obtained as colorless oil.

$^1$H-NMR(CDCl$_3$): δ=0.70 ppm (d, J=4.5 Hz, 3H, H-18); 1.41 (d, J=21 Hz, 3H, H-21); 2.44 (dd, J=10.5, 7.5 Hz, 1H, H-14); 3.26 (s, 3H, N-Me); 3.73 (s, 3H, N-OMe); 6.62 (d, J=15.5 Hz, 1H, H-23); 6.98 (d, J=25 Hz, 15.5 Hz, 1H, H-22).

107) (7E,22E) - (1R,3R,20R)-1,3-Bis[[dimethyl(1,1-dimethylethyl)silyl]oxy]-20-fluoro-N-methoxy-N-methyl-19-nor-9,10-secochola-5,7-triene-24-amide 108

600 mg (2.5 mmol) of 107 is reacted analogously to 70) and 470 mg of the title compound is obtained as colorless foam.

$^1$H-NMR(CDCl$_3$): δ=0.03 ppm (s, 12H, SiMe); 0.60 (d, J=4.5 Hz, 3H, H-18); 0.81 and 0.82 (2x s; 9H, Si-t-butyl each); 1.45 (d, J=21 Hz, 3H, H-21); 3.24 (s, 3H, N-Me); 3.72 (s, 3H, N-OMe); 4.03 (m, 2H, H-1 and H-3); 5.77 and 6.12 (2x d, J=11 Hz; 1H H-6 and H-7 each); 6.57 (d, J=15.5 Hz, 1H, H-23); 6.98 (dd, J=25, 15.5 Hz, 1H, H-22).

108) (7E,22E) - (1R,3R,20R)-1,3-Bis [[dimethyl(1,1-dimethylethyl)silyl]oxy]-20-fluoro-19-nor-9,10-secochola-5,7,22-trien-24-al 109

440 mg (0.66 mmol) of 108 is reacted with 3.3 mmol of DIBAH solution analogously to 40) and 294 mg of the title compound is obtained as colorless foam.

$^1$H-NMR(CDCl$_3$) : δ=0.02 ppm (s, 12H, SiMe); 0.58 (d, J=4.5 Hz, 3H, H-18); 0.82 and 0.83 (2x s; 9H, Si-t-butyl each); 1.45 (d, J=21 Hz, 3H, H-21); 4.03 (m, 2H, H-1 and H-3); 5.78 and 6.11 (2x d, J=11 Hz; 1H H-6 and H-7 each); 6.29 (dd, J=15.5, 8 Hz, 1H, H-23); 6.84 (dd, J=25, 15.5 Hz, 1H, H-22); 9.62 (dbr, J=8 Hz, 1H, H-24).

EXAMPLE 34

109) (7E,22E)-(1R,3R,20R,24S)-1,3-Bis [[dimethyl(1,1-dimethylethyl)silyl]oxy]-20-fluoro-24-hydroxy-19-nor-9,10-secocholesta-5,7,22-triene-25-carboxylic acid ethyl ester 110

Analogously to 41) 240 mg (0.39 mmol) of 109 is reacted with 3.9 mmol of LDA and 0.52 ml (3.9 mmol) of isobutyric acid ethyl ester and 160 mg of the title compound is obtained as colorless foam.

$^1$H-NMR(CD$_2$Cl$_2$): δ=0.01 ppm (s, 12H, SiMe); 0.55 (d, J=4.5 Hz, 3H, H-18); 0.82 and 0.83 (2x s; 9H, Si-t-butyl each); 1.11 and 1.13 (2x s; 3H, H-26 and H-27 each); 1.22 (t, J=7 Hz, 3H, COOEt); 1.46 (d, J=21 Hz, 3H, H-21); 4.02 (m, 2H, H-1 and H-3); 4.08 (q, J-7 Hz, 2H, COOEt); 4.13 (m, 1H, H-24); 5.63 (dd, J=15.5, 7 Hz, 1H, H-23); 5.83 (dd, J=25, 15.5 Hz, 1H, H-22); 5.79 and 6.13 (2x d, J=11 Hz; 1H, H-6 and H-7 each).

110) (7E,22E) - (1R,3R,20R,24S)-20-Fluoro-1,3,24-trihydroxy-19-nor-9,10- secocholesta-5,7,22-triene-25-carboxylic acid ethyl ester 111

150 mg (0.2 mmol) of 110 is reacted analogously to 103) and 25 mg of the title compound is obtained as colorless foam.

$^1$H-NMR(CD$_2$Cl$_2$): δ=0.60 ppm (d, J=4.5 Hz, 3H, H-18); 1.15 and 1.18 (2x s; 3H, H-26 and H-27 each); 1.23 (t, J=7 Hz, 3H, COOEt); 1.35 (d, J=21 Hz, 3H, H-21); 3.99 and 4.08 (2x m; 1H, H-1 and H-3 each); 4.12 (q, J-7 Hz, 2H, COOEr); 4.18 (d, J=7 Hz, 1H, H-24); 5.68 (dd, J=15.5, 7 Hz, 1H, H-23); 5.88 (dd, J=25, 15.5 Hz, 1H, H-22); 5.83 and 6.28 (2x d, J=11 Hz; 1H, H-6 and H-7 each).

Derivatives in the standard series (supplement to EM 50741)

EXAMPLE 35

111) (5E,7E,22E) - (1S,3R) -1,3-Bis[[dimethyl (1,1dimethylethyl)silyl]oxy]-24-hydroxy-9,10-secocholesta-5,7,10(19),22-tetraene-25-carboxylic acid butyl ester 112

500 mg (0.91 mmol) of (5E,7E,22E) - (1S, 3R) -1,3-bis [[dimethyl(1,1-dimethylethyl)silyl]oxy]-9,10-secochola-5,7,10(19),22-trien-24-al 3 is reacted with 4.5 mmol of LDA and 0.76 ml (4.5 mmol) of isobutyric acid butyl ester analogously to 41) and 677 mg of the title compound is obtained as colorless foam (1:1 diastereomers relative to C-24).

$^1$H-NMR(CDCl$_3$): δ=0.04 ppm (s, 12H, SiMe); 0.53 (s, 3H, H-18); 0.88 and 0.90 (2x s; 9H, Si-t-butyl each); 0.99 (t, J=7 Hz, 3H COOBu); 1.02 (d, J=7 Hz, 3H, H-21); 1.13/1.4 and 1.15/1.16 (2x s; 3H, C-26 and C-27 each); 4.07 (t, J=7 Hz, 2H COOBu); 4.09 (m, 1H, H-24); 4.19 (m, 1H, H-3); 4.51 (m, 1H, H-1); 4.92 and 4.97 (2x s; 1H, H-19 each); 5.36/5.38 (dd, J=15, 7 Hz, 1H, H-23); 5.52/5.57 (dd, J=15, 9 Hz, 1H, H-22); 5.80 and 6.43 (2x d, J=11 Hz; 1H, H-6 and H-7 each).

112) (5Z,7E,22E)-(1S,3R,24R)-1,3-Bis[[dimethyl(1,1-dimethylethyl)silyl]oxy]-24 -hydroxy-9,10-secocholesta-5,7,10 (19), 22-tetraene-25-carboxylic acid butyl ester 113a and (5Z,7E,22E) - (1S,3R,24S)-1,3-bis[[dimethyl (1,1dimethylethyl)silyl]oxy]-24-hydroxy-9,10-secocholesta-5,7, 10(19), 22-tetraene-25-carboxylic acid butyl ester 113b 670 mg (0.90 mmol) of 112 is dissolved in 80 ml of toluene and the solution is irridated in the presence of 180 mg (0.96 mmol) anthracene and 0.1 ml of triethylamine in a pyrex-immersion reactor with a mercury high-pressure lamp (Philips HPK 125) under nitrogen for 10 minutes. The solvent is removed and the residue is purified chromatographically on silica gel with hexane/ethyl acetate and 102 mg of 113a and 158 mg of 113b accumulate as colorless foams.

$^1$H-NMR(CDCl$_3$) : δ=0.06 ppm (s, 12H, SiMe); 0.54 (s, 3H, H-18); 0.88 (s, 18H, Si-t-butyl); 0.96 (t, J=7 Hz, 3H COOBu); 1.05 (d, J=7 Hz, 3H, H-21); 1.16 and 1.17 (2x s; 3H, H-26 and H-27 each); 2.60 (d, J=6 Hz, 1H, OH); 4.06 (dd, J=7, 6 Hz, 1H, H-24); 4.10 (t, J=7 Hz, 2H COOBu); 4.20 (m, 1H, H-3); 4.38 (m, 1H, H-1); 4.87 and 5.18 (2x s; 1H, H-19 each); 5.36 (dd, J=15, 7 Hz, 1H, H-23); 5.52 (dd, J=15, 9 Hz, 1H, H-22); 6.01 and 6.23 (2x d, J=11 Hz; 1H, H- 6 and H- 7 each)

$^1$H-NMR(CDCl$_3$): δ=0.06 ppm (s, 12H, SiMe); 0.53 (s, 3H, H-18); 0.88 (s, 18H, Si-t-butyl); 0.94 (t, J=7 Hz, 3H COOBu); 1.03 (d, J=7 Hz, 3H, H-21); 1.17 and 1.18 (2x s; 3H, H-26 and H-27 each); 2.58 (d, J=6 Hz, 1H, OH); 4.10 (dd, J=7, 6 Hz, 1H, H-24); 4.10 (t, J=7 Hz, 2H COOBu); 4.18 (m, 1H, H-3); 4.37 (m, 1H, H-I); 4.87 and 5.18 (2x s, 1H, H-19 each); 5.38 (dd, J=15, 7 Hz, 1H, H-23); 5.59 (dd, J=15, 9 Hz, 1H, H-22 ); 6.01 and 6.23 (2x d, J=11 Hz 1H, H-6 and H-7 each).

113) (5Z,7E,22E) - (1S,3R,24R) -1,3,24-Trihydroxy-9,10-secocholesta-5,7,10 (19),22-tetraene-25-carboxylic acid butyl ester 114a 100 mg (0.13 mmol) of 113a is reacted analogously to 73) and 39 mg of the title compound is obtained as colorless foam.

$^1$H-NMR(CD$_2$Cl$_2$): δ=0.57 ppm (s, 3H, H-18); 0.93 (t, J=7 Hz, 3H COOBu); 1.04 (d, J=7 Hz, 3H, H-21); 1.12 (s; 3H, H-26 and H-27 each); 2.45 (d, J=6 Hz, 1H, OH); 4.02 (dd, J=7, 6 Hz, 1H, H-24); 4.06 (t, J=7 Hz, 2H COOBu); 4.17 (m, 1H, H-3); 4.38 (m, 1H, H-1); 4.95 and 5.28 (2x s; 1H, H-19 each); 5.35 (dd, J=15, 7 Hz, 1H, H-23); 5.51 (dd, J=15, 9 Hz, 1H, H-22); 6.01 and 6.36 (2x d, J=11 Hz; 1H, H- 6 and H- 7 each) .

114) (5Z,7E,22E) - (1S,3R,24S)-1,3,24-Trihydroxy-9,10-secooholesta-5,7,10(19),22-tetraene-25-carboxylic acid butyl ester 114b 155 mg (0.21 mmol) of 113b is reacted analogously to 73) and 69 mg of the title compound is obtained as colorless foam.

$^1$H-NMR(CD$_2$Cl$_2$) : δ=0.56 ppm (s, 3H, H-18); 0.94 (t, J=7 Hz, 3H COOBu); 1.03 (d, J=7 Hz, 3H, H-21); 1.12 (s; 3H, H-26 and H-27 each); 2.46 (d, J=6 Hz, 1H, OH); 4.08 (m, 1H, H-24); 4.08 (t, J=7 Hz, 2H COOBu); 4.17 (m, 1H, H-3); 4.39 (m, 1H, H-1); 4.96 and 5.29 (2x s; 1H, H-19 each); 5.37 (dd, J=15, 7 Hz, 1H, H-23); 5.57 (dd, J=15, 9 Hz, 1H, H-22); 6.01 and 6.36 (2x d, J=11 Hz; 1H, H-6 and H-7 each) .

EXAMPLE 36

115) (5E,7E,22E) - (1S,3R)-1,3-Bis[[dimethyl(1,1dimethylethyl)silyl]oxy]-24 -hydroxy-9,10 -secocholesta-5,7, 10(19), 22-tetraene-25-carboxylic acid-2-methylpropyl ester 115

500 mg (0.91 mmol) of (5E,7E,22E) - (1S,3R)-1,3-bis [[dimethyl(1,1-dimethylethyl)silyl]oxy]-9,10-secochola-5, 7,10(19),22-trien-24-al 3 is reacted with 4.5 mmol of LDA and 0.76 ml (4.5 mmol) of isobutyric acid butyl ester analogously to 41) and 400 mg of the title compound is obtained as colorless foam (1:1 diastereomers relative to C-24).

$^1$H-NMR(CDCl$_3$): δ=0.03 ppm (s, 12H, SiMe); 0.57 (s, 3H, H-18); 0.89 (s, 18H, Si-t-butyl); 0.90 and 0.92 (2x d, J=7 Hz; 6H COOiBu each); 1.04/1.05 (d, J=7 Hz, 3H, H-21); 1.17 and 1.18 (2x s; 3H, H-26 and H-27 each); 4.10 (m, 1H, H-24); 4.23 (m, 1H, H-3); 4.53 (m, 1H, H-I); 4.94 and 4.99 (2x s; 1H, H-19 each); 5.37/5.39 (dd, J=15, 7 Hz, 1H, H-23); 5.53/5.59 (dd, J=15, 9 Hz, 1H, H-22); 5.81 and 6.46 (2x d, J=11 Hz; 1H, H-6 and H-7 each).

116) (5Z,7E,22E) - (1S,3R,24R)-1,3-Bis[[dimethyl(1,1-dimethylethyl)silyl]oxy]-24-hydroxy-9,10-secocholesta-5, 7,10(19), 22-tetraene-25-carboxylic acid-2 -methylpropyl ester 116a and (5Z,7E,22E) - (1S,3R,24S) -1,3-bis [[dimethyl (1,1-dimethylethyl)silyl]oxy]-24-hydroxy-9,10-secocholesta-5,7,10(19), 22 -tetraene-25-carboxylic acid-2-methylpropyl ester 116b 400 mg (0.54 mmol) of 115 is reacted analogously to 112) and 102 mg of 116a and 200 mg of 116b are obtained as colorless foams.

$^1$H-NMR (CDCl$_3$): 116a: δ=0.05 ppm (s, 12H, SiMe); 0.55 (s, 3H, H-18); 0.89 (s, 18H, Si-t-butyl); 0.95 (d, J=7 Hz, 6H COOiBu); 1.05 (d, J=7 Hz, 3H, H-21); 1.19 and 1.20 (2x s; 3H, H-26 and H-27 each); 2.60 (d, J=6 Hz, 1H, OH); 3.89 (d, J=7 Hz, 2H COOiBu); 4.08 (dd, J=7, 6 Hz, 1H, H-24); 4.19 (m, 1H, H-3); 4.38 (m, 1H, H-1); 4.87 and 5.18 (2x s; 1H, H-19 each); 5.37 (dd, J=15, 7 Hz, 1H, H-23); 5.52 (dd, J=15, 9 Hz, 1H, H-22); 6.02 and 6.23 (2x d, J=11 Hz; 1H, H-6 and H-7 each).

116b: δ=0.05 ppm (s, 12H, SiMe); 0.54 (s, 3H, H-18); 0.89 (s, 18H, Si-t-butyl); 0.96 (d, J=7 Hz, 6H COOiBu); 1.04 (d, J=7 Hz, 3H, H-21); 1.18 and 1.19 (2x s; 3H, H-26 and H-27 each); 2.59 (d, J=7 Hz, 1H, OH); 3.89 (d, J=7 Hz, 2H COOiBu); 4.10 (t, J=7, 6 Hz, 1H, H-24); 4.19 (m, 1H, H-3); 4.38 (m, 1H, H-1); 4.87 and 5.18 (2x s; 1H, H-19 each); 5.39 (dd, J=15, 7 Hz, 1H, H-23); 5.59 (dd, J=15, 9 Hz, 1H, H-22); 6.02 and 6.23 (2x d, J=11 Hz; 1H, H- 6 and H- 7 each) .

117) (5Z,7E,22E) - (1S,3R,24R) -1,3,24-Trihydroxy-9, 10-secocholesta-5,7,10 (19),22-tetraene-25-carboxylic acid-2-methylpropyl ester 117a 98 mg (0.13 mmol) of 116a is reacted analogously to 73) and 48 mg of the title compound is obtained as colorless foam.

$^1$H-NMR(CD$_2$Cl$_2$): δ=0.57 ppm (s, 3H, H-18); 0.95 (d, J=7 Hz, 6H COOiBu); 1.04 (d, J=7 Hz, 3H, H-21); 1.12 and 1.13 (2x s; 3H, H-26 and H-27 each); 2.44 (d, J=6 Hz, 1H, OH); 3.85 (d, J=7 Hz, 2H COOiBu); 4.04 (dd, J=7, 6 Hz, 1H, H-24); 4.17 (m, 1H, H-3); 4.38 (m, 1H, H-I); 4.95 and 5.28 (2x s; 1H, H-19 each); 5.36 (dd, J=15, 7 Hz, 1H, H-23); 5.52 (dd, J=15, 9 Hz, 1H, H-22); 6.01 and 6.37 (2x d, J=11 Hz; 1H, H-6 and H-7 each).

118) (5Z,7E,22E) - (1S,3R,24S) -1,3,24-Trihydroxy-9,10-secocholesta-5,7,10 (19),22-tetraene-25-carboxylic acid-2-methylpropyl ester 117b 193 mg (0.26 mmol) of 116b is reacted analogously to 73) and 105 mg of the title compound is obtained as colorless foam.

$^1$H-NMR(CD$_2$Cl$_2$): δ=0.56 ppm (s, 3H, H-18); 0.95 (d, J=7 Hz, 6H COOiBu); 1.03 (d, J=7 Hz, 3H, H-21); 1.14 (s; 3H, H-26 and H-27 each); 2.46 (d, J=6 Hz, 1H, OH); 3.84 (d, J=7 Hz, 2H COOiBu); 4.08 (dd, J=7, 6 Hz, 1H, H-24); s; 1H, H-19 each); 5.38 (dd, J=15, 7 Hz, 1H, H-23); 5.58 (dd, J=15, 9 Hz, 1H, H-22); 6.00 and 6.37 (2x d, J=11 Hz; 1H, H-6 and H-7 each).

EXAMPLE 37

119) (5E,7E,22E)-(1S,3R)-1,3-Bis[[dimethyl(1,1-dimethylethyl)silyl]oxy]-24-hydroxy-9,10-secocholesta-5,7,10(19),22 -tetraene-25-carboxylic acid pentyl ester 500 mg (0.91 mmol) of (5E,7E,22E) - (1S,3R)-bis[[dimethyl (1,1-dimethylethyl)silyl]oxy]-9,10-secochola-5,7,10(19),22-trien-24-al 3 is reacted with 4.5 mmol of LDA and 0.76 ml (4.5 mmol) of isobutyric acid pentyl ester analogously to 41) and 550 mg of the title compound is obtained as colorless foam (1:1 diastereomers relative to C-24).

$^1$H-NMR(CDCl$_3$) : δ=0.03 ppm (s, 12H, SiMe); 0.52 (s, 3H, H-18); 0.88 (t, J=7 Hz, 3H, COOPent); 0.90 (s, 18H, Si-t-butyl); 1.01/1.02 (d, J=7 Hz, 3H, H-21); 1.14 and 1.15 (2x s; 3H, H-26 and H-27 each); 2.51 (quint, J-7 Hz, 2H, COOPent); 4.02 (t, J-7 Hz, 2H, COOPent); 4.08 (m, 1H, H-24); 4.20 (m, 1H, H-3); 4.52 (m, 1H, H-1); 4.93 and 4.98 (2x s; 1H, H-19 each); 5.35/5.39 (dd, J=15, 7 Hz, 1H, H-23); 5.52/5.57 (dd, J=15, 7 Hz, 1H, H-22); 5.80 and 6.43 (2x d, J=11 Hz; 1H, H-6 and H-7 each).

120) (5Z,7E,22E) - (1S,3R,24R)-1,3-Bis[[dimethyl(1,1-dimethylethyl)silyl]oxy]-24-hydroxy-9,10-secocholesta-5,7,10(19),22-tetraene-25-carboxylic acid pentyl ester 119a and (5Z,7E,22E) - (1S,3R,24S)-1,3 -bis [[dimethyl(1,1-dimethylethyl)silyl]oxy]-24-hydroxy-9,10-secocholesta-5,7,10(19), 22-tetraene-25-carboxylic acid pentyl ester 119b 500 mg (0.71 mmol) of 118 is reacted analogously to 112) and 156 mg of 119a and 174 mg of 119b are obtained as colorless foams.

$^1$H-NMR(CDCl$_3$): 119a: δ=0.03 ppm (s, 12H, SiMe); 0.53 (s, 3H, H-18); 0.87 (s, 18H, Si-t-butyl); 0.89 (t, J=7 Hz, 3H, COOPent); 1.02 (d, J=7 Hz, 3H, H-21); 1.17 and 1.18 (2x s; 3H, H-26 and H-27 each); 2.60 (d, J=6 Hz, 1H, OH); 4.08 (m, 1H, H-24); 4.09 (t, J=7 Hz, 2H, COOPent); 4.18 (m, 1H, H-3); 4.35 (m, 1H, H-1); 4.85 and 5.16 (2x s; 1H, H-19 each); 5.36 (dd, J=15, 7 Hz, 1H, H-23); 5.53 (dd, J=15, 7 Hz, 1H, H-22); 6.00 and 6.23 (2x d, J=11 Hz; 1H, H-6 and H-7 each).

119b: δ=0.03 ppm (s, 12H, SiMe); 0.52 (s, 3H, H-18); 0.86 (s, 18H, Si-t-butyl); 0.88 (t, J=7 Hz, 3H, COOPent); 1.01 (d, J=7 Hz, 3H, H-21); 1.15 and 1.16 (2x s; 3H, H-26 and H-27 each); 2.57 (d, J=6 Hz, 1H, OH); 4.08 (m, 1H, H-24); 4.08 (t, J=7 Hz, 2H, COOPent); 418 (m, 1H, H-3); 4.34 (m, 1H, H-1); 4.83 and 5.14 (2x s; 1H, H-19 each); 5.37 (dd, J=15, 7 Hz, 1H, H-23); 5.56 (dd, J=15, 9 Hz, 1H, H-22); 5.98 and 6.22 (2x d, J=11 Hz; 1H, H-6 and H-7 each).

121) (5Z,7E,22E) - (1S,3R,24R) -1,3,24-Trihydroxy9,10-secocholesta-5,7,10 (19) , 22 -tetraene-25-carboxylic acid pentyl ester 120a 150 mg (0.2 mmol) of 119a is reacted analogously to 73) and 75 mg of the title compound is obtained as colorless foam.

$^1$H-NMR(CD$_2$Cl$_2$): δ=0.58 ppm (s, 3H, H-18); 0.90 (t, J=7 Hz, 2H, COOPent); 1.04 (d, J=7 Hz, 3H, H-21); 2.43 (d, J=6 Hz, 1H, OH); 4.05 (t, J=7 Hz, 2H, COOPent); 4.08 (m, 1H, H-24); 4.17 (m, 1H, H-3); 4.38 (m, 1H, H-1) 4.95 and 5.28 (2x s; 1H, H-19 each); 5.35 (dd, J=15, 7 Hz, 1H, H-23); 5.52 (dd, J=15, 9 Hz, 1H, H-22); 6.01 and 6.37 (2x d, J=11 Hz; 1H, H-6 and H-7 each).

122) (5Z,7E,22E) - (1S,3R,24S) -1,3,24-Trihydroxy9,10-secocholesta-5,7,10(19),22-tetraene-25-carboxylic acid pentyl ester 120b 169 mg (0.22 mmol) of 119b is reacted analogously to 73) and 86 mg of the title compound is obtained as colorless foam.

$^1$H-NMR(CD$_2$Cl$_2$): δ=0.57 ppm (s, 3H, H-18); 0.91 (t, J=7 Hz, 3H, COOPent); 1.02 (d, J-7 Hz, 3H, H-21); 2.44 (d, J=6 Hz, 1H, OH); 4.03 (t, J=7 Hz, 2H, COOPent); 4.06 (m, 1H, H-24); 4.18 (m, 1H, H-3); 4.38 (m, 1H, H-I); 4.95 and 5.29 (2x s; 1H, H-19 each); 5.38 (dd, J=15, 7 Hz, 1H, H-23); 5.56 (dd, J=15, 9 Hz, 1H, H-22); 6.01 and 6.37 (2x d, J=11 Hz; 1H, H-6 and H-7 each).

Cyclobutyl Series

EXAMPLE 38

123) (5E,7E,22E) - (1S,3R)-1,3-Bis[[dimethyl(1,1-dimethylethyl)silyl]oxy]-24-hydroxy-26a,27-cyclo-26a-homo-9,10-secocholesta-5,7,10(19),22-tetraene-25carboxylic acid ethyl ester 121

400 mg (0.72 mmol) of (5E,7E,22E) - (1S,3R)-bis[[dimethyl (1,1-dimethylethyl)silyl]oxy]-9,10-secochola-5,7,10 (19) ,22-trien-24-al 3 is reacted with 2.2 mmol of LDA and 281 mg (2.2 mmol) of cyclobutane carboxylic acid ethyl ester analogously to 41) and 300 mg of the title compound is obtained as colorless foam (1:1 diastereomers relative to C-24).

$^1$H-NMR(CDCl$_3$): δ=0.02 ppm (s, 12H, SiMe); 0.50 (s, 3H, H-18); 0.83 and 0.86 (2x s; 9H, Si-t-butyl each); 0.98/0.99 (d, J=7 Hz, 3H, H-21); 1.25 (t, J-7 Hz, 2H, COOEt); 4.17 (q, J-7 Hz, 2H, COOEr); 4.18 (m, 2H, H-3 and H-24); 4.49 (m, 1H, H-1); 4.89 and 4.92 (2x s; 1H, H-19 each)/5.35/5.38 (dd, J=15, 6 Hz, 1H, H-23); 5.52 and 5.57 (dd, J=15, 7 Hz, 1H, H-22); 5.76 and 6.40 (2x d, J=11 Hz; 1H, H-6 and H-7 each).

124) (5Z,7E,22E)-(1S,3R,24R)-1,3-Bis[[dimethyl(1,1-dimethylethyl)silyl]oxy]-24-hydroxy-26a,27-cyclo-26a-homo-9,10-secocholesta-5,7,10(19),22-tetraene-25-carboxylic acid ethyl ester 122a and (5E,7E,22E) (1S,3R,24S)-1,3-bis[[dimethyl(1,1-dimethylethyl)silyl]oxy]-24-hydroxy-26a,27-cyclo-26a -homo-9,10-secocholesta-5,7,10 (19), 22-tetraene-25carboxylic acid ethyl ester 122b 300 mg (0.41 mmol) of 121 is reacted analogously to 112) and 43 mg of 122a and 67 mg of 122b are obtained as colorless foams.

$^1$H-NMR(CDCl$_3$): 122a: δ=0.06 ppm (s, 12H, SiMe); 0.53 (s, 3H, H-18); 0.89 (s, 18H, Si-t-butyl); 1.02 (t, J=7 Hz, 3H, H-21); 1.30 (t, J=7 Hz, 3H, COOEr); 2.67 (d, J=6 Hz, 1H, OH); 4.19 (q, J=7 Hz, 2H, COOEt); 4.20 (m, 2H, H-3 and H-24); 4.37 (m, 1H, H-1); 4.85 and 5.18 (2x s; 1H, H-19 each); 5.38 (dd, J=15, 7 Hz, 1H, H-23); 5.58 (dd, J=15, 7 Hz, 1H, H-22); 6.00 and 6.23 (2x d, J=11 Hz; 1H, H-6 and H-7 each).

122b: δ=0.06 ppm (s, 12H, SiMe); 0.53 (s, 3H, H-18); 0.89 (s, 18H, Si-t-butyl); 1.02 (t, J=7 Hz, 3H, H-21); 1.30 (t, J=7 Hz, 3H, COOEt); 2.64 (d, J=6 Hz, 1H, OH); 4.18 (q, J=7 Hz, 2H, COOEt); 4.20 (m, 2H, H-3 and H-24); 4.22 (m, 1H, H-24); 4.37 (m, 1H, H-1); 4.85 and 5.18 (2x s; 1H, H-19 each); 5.40 (dd, J=15, 7 Hz, 1H, H-23); 5.61 (dd, J=15, 7 Hz, 1H, H-22); 6.00 and 6.23 (2x d, J=11 Hz; 1H, H-6 and H-7 each).

125) (5Z,7E,22E) - (1S,3R,24R)-1,3,24-Trihydroxy-26a,27-cyclo-26a-homo-9,10-secocholesta-5,7,10(19), 22-tetraene-25-carboxylic acid ethyl ester 123a 43 mg (0.059 mmol) of 122a is reacted analogously to 73) and 15 mg of the title compound is obtained as colorless foam.

$^1$H-NMR (CD$_2$Cl$_2$): δ=0.52 ppm (s, 3H, H-18); 1.01 (d, J=7 Hz, 3H, H-21); 1.23 (t, J=7 Hz, 3H, COOEr); 4.13 (q, J=7 Hz, 2H, COOEt); 4.13 (m, 2H, H-3 and H-24); 4.33 (m, 1H, H-1); 4.91 and 5.25 (2x s; 1H, H-19 each); 5.34 (dd, J=15, 7 Hz, 1H, H-23); 5.53 (dd, J=15, 7 Hz, 1H, H-22); 5.96 and 6.32 (2x d, J=11 Hz; 1H, H-6 and H-7 each).

126) (5Z,7E,22E) - (1S, 3R,24S) -1, 3,24-Trihydroxy-26a,27-cyclo-26a-homo-9,10-secocholesta-5,7,10(19), 22-tetraene-25-carboxylic acid ethyl ester 123b 43 mg (0.059 mmol) of 122b is reacted analogously to 73) and 26 mg of the title compound is obtained as colorless foam.

$^1$H-NMR(CD$_2$Cl$_2$): δ=0.52 ppm (s, 3H, H-18); 1.00 (d, J=7 Hz, 3H, H-21); 1.24 (t, J=7 Hz, 3H, COOEt); 4.12 (q, J=7 Hz, 2H, COOEt); 4.13 (m, 2H, H-3 and H-24); 4.34 (m, 1H, H-1); 4.92 and 5.26 (2x s; 1H, H-19 each); 5.38 (dd, J=15, 7 Hz, 1H, H-23 ); 5.57 (dd, J=15, 7 Hz, 1H, H-22 ); 5.97 and 6.33 (2x d, J=11 Hz; 1H, H-6 and H-7 each).

C-24 Ketones (standard series)

EXAMPLE 39

127) (5Z,7E,22E) - (1S,3R) -1,3-Bis[[dimethyl(1,1-dimethylethyl)silyl]oxy]-24-oxo-9,10-secocholesta-5,7,10(19), 22-tetraene-25-carboxylic acid methyl ester 124

200 mg (0.3 mmol) of 14a is reacted analogously to 78) and 135 mg of the title compound is obtained as colorless foam.

$^1$H-NMR(CDCl$_3$): δ=0.01 ppm (s, 12H, SiMe); 0.50 (s, 3H, H-18); 0.82 (s, 18H, Si-t-butyl); 1.02 (d, J=7 Hz, 3H, H-21); 1.33 (s; 6H, C-26 and C-27 each); 3.64 (s, 3H, COOMe); 4.12 (m, 1H, H-3); 4.31 (m, 1H, H-1); 4.89 and 5.12 (2x s; 1H, H-19 each); 5.95 and 6.18 (2x d, J=11 Hz, 1H, H-6 and H-7); 6.08 (d, J=15 Hz, 1H, H-23 ); 6.78 (dd, J=15, 9.5 Hz, 1H, H-22).

128) (5Z,7E,22E) - (1S,3R) -1,3-Dihydroxy-24-oxo-9,10-secocholesta-5,7,10(19),22-tetraene-25-carboxylic acid methyl ester 125

130 mg (0.19 mmol) of 124 is reacted analogously to 73) and 31 mg of the title compound is obtained as colorless foam.

$^1$H-NMR(CD$_2$Cl$_2$) : δ=0.55 ppm (s, 3H, H-18); 1.06 (d, J=7 Hz, 3H, H-21); 1.33 (3, 6H, C-26 and C-27); 3.65 (s, 3H, COOMe); 4.14 (m, 1H, H-3); 4.35 (m, 1H, H-1); 4.93 and 5.25 (2x s; 1H, H-19 each); 5.98 and 6.34 (2x d, J=11 Hz, 1H, H-6 and H-7); 6.13 (d, J=15 Hz, 1H, H-23); 6.76 (dd, J=15, 9.5 Hz, 1H, H-22).

EXAMPLE 40

129) (5Z,7E,22E) - (1S,3R) -1,3-Bis[[dimethyl(1,1-dimethylethyl)silyl]oxy]-24-oxo-9,10-secocholesta-5,7,10(19),22-tetraene-25-carboxylic acid ethyl ester 420 mg (0.59 mmol) of 5a is reacted analogously to 78) and 350 mg of the title compound is obtained as colorless foam.

$^1$H-NMR(CDCl$_3$): δ=0.01 ppm (s, 12H, SiMe); 0.50 (s, 3H, H-18); 0.82 (s, 18H, Si-t-butyl); 1.02 (d, J=7 Hz, 3H, H-21); 1.18 (t, J=7 Hz, 3H, COOEt); 1.20 and 1.30 (2x s; 3H, C-26 and C-27 each); 4.10 (q, J=7 Hz, 2H, COOEt); 4.12 (m, 1H, H-3); 4.30 (m, 1H, H-1); 4.89 and 5.10 (2x s; 1H, H-19 each); 5.95 and 6.18 (2x d, J=11 Hz, 1H, H-6 and H-7); 6.08 (d, J=15 Hz, 1H, H-23); 6.78 (dd, J=15, 9.5 Hz, 1H, H-22).

130) (5Z,7E,22E) - (1S,3R)-1,3-Dihydroxy-24-oxo-9,10-secocholesta-5,7,10(19),22-tetraene-25-carboxylic acid ethyl ester 127

50 mg (0.07 mmol) of 126 is reacted analogously to 73) and 23 mg of the title compound is obtained as colorless foam.

$^1$H-NMR(CD$_2$Cl$_2$): δ=0.55 ppm (s, 3H, H-18); 1.06 (d, J=7 Hz, 3H, H-21); 1.30 (t, J=7 Hz, 3H, COOEr); 1.32 (s, 6H, C-26 and C-27); 4.13 (q, J=7 Hz, 3H, COOEt); 4.14 (m, 1H, H-3); 4.35 (m, 1H, H-1); 4.93 and 5.27 (2x s; 1H, H-19 each); 5.98 and 6.34 (2x d, J=11 Hz; 1H, H-6 and H-7 each); 6.13 (d, J=15 Hz, 1H, H-23); 6.78 (dd, J=15, 9 Hz, 1H, H-22).

EXAMPLE 41

131) (5Z,7E,22E)-(1S,3R)-1,3-Bis[[dimethyl(1,1dimethylethyl)silyl]oxy]-24-oxo-9,10-secocholesta-5,7,10(19),22-tetraene-25-carboxylic acid propyl ester 204 mg (0.3 mmol) of compound 18a (EM 50741) is reacted analogously to 78) and 155 mg of the title compound is obtained as colorless foam.

$^1$H-NMR(CDCl$_3$) : δ=0.01 ppm (s, 12H, SiMe); 0.50 (s, 3H, H-18); 0.83 (s, 18H, Si-t-butyl); 0.84 (t, J=7 Hz, 3H, COOPr); 1.02 (d, J=7 Hz, 3H, H-21); 1.19 and 1.30 (2x s; 3H, C-26 and C-27 each); 4.02 (m, Hz, 2H, COOPr); 4.13 (m, 1H, H-3); 4.30 (m, 1H, H-1); 4.90 and 5.11 (2x s; 1H, H-19 each); 5.95 and 6.19 (2x d, J=11 Hz; 1H, H-6 and H-7 each); 6.08 (d, J=15 Hz, 1H, H-23 ); 6.77 (dd, J=15, 9 Hz, 1H, H-22).

132) (5Z,7E,22E)-(1S,3R)-1,3-Dihydroxy-24-oxo-9,10-secocholesta-5,7,10(19),22-tetraene-25-carboxylic acid propyl ester 129

145 mg (0.2 mmol) of 128 is reacted analogously to 73) and 56 mg of the title compound is obtained as colorless foam.

$^1$H-NMR(CD$_2$Cl$_2$): δ=0.55 ppm (s, 3H, H-18); 0.80 (t, J=7 Hz, 3H, COOPr); 1.08 (d, J=7 Hz, 3H, H-21); 1.32 (3, 6H, C-26 and C-27); 4.03 (t, J=7 Hz, 2H, COOPr); 4.17 (m, 1H, H-3); 4.38 (m, 1H, H-I); 4.95 and 5.29 (2x s; 1H, H-19 each); 6.00 and 6.35 (2x d, J=11 Hz; 1H, H-6 and H-7 each); 6.15 (d, J=15 Hz, 1H, H-23); 6.79 (dd, J=15, 9 Hz, 1H, H-22).

EXAMPLE 42

133) (5Z,7E,22E) - (1S,3R)-1,3-Bis[[dimethyl(1,1-dimethylethyl)silyl]oxy]-24-oxo-9,10-secocholesta-5,7,10(19), 22-tetraene-25-carboxylic acid-1-methyl ethyl ester 130

800 mg (1.14 mmol) of 12a is reacted analogously to 78) and 630 mg of the title compound is obtained as colorless foam.

¹H-NMR(CDCl₃): δ=0.01 ppm (s, 12H, SiMe); 0.50 (s, 3H, H-18); 0.83 (s, 18H, Si-t-butyl); 1.03 (d, J=7 Hz, 3H, H-21); 1.18 (d, J=7 Hz, 6H, COOiPr); 1.31 (s, 6H, C-26 and C-27); 4.13 (m, 1H, H-3); 4.32 (m, 1H, H-1); 4.95 (hept. J=7 Hz, 1H, COOiPr); 4.89 and 5.12 (2x s; 1H, H-19 each); 5.95 and 6.17 (2x d; J=11 Hz, 1H, H-6 and H-7 each); 6.08 (d, J=15 Hz, 1H, H-23); 6.79 (dd, J=15, 9.5 Hz, 1H, H-22).

134) (5Z,7E,22E) - (1S,3R)-1,3-Dihydroxy-24-oxo-9,10-secocholesta-5,7,10(19),22-tetraene-25-carboxylic acid-1-methyl ethyl ester 131

130 mg (0.18 mmol) of 130 is reacted analogously to 73) and 64 mg of the title compound is obtained as colorless foam.

¹H-NMR(CD₂Cl₂): δ=0.55 ppm (s, 3H, H-18); 1.06 (d, J=7 Hz, 3H, H-21); 1.22 (d, J=7 Hz, 6H, COOiPr); 1.31 (3, 6H, C-26 and C-27); 4.14 (m, 1H, H-3); 4.36 (m, 1H, H-1); 4.99 (hept. J=7 Hz, 1H, COOiPr); 4.94 and 5.28 (2x s; 1H, H-19 each); 5.99 and 6.35 (2x d, J=11 Hz; 1H, H-6 and H-7 each); 6.13 (d, J=15 Hz, 1H, H-23); 6.78 (dd, J=15, 9 Hz, 1H, H-22).

EXAMPLE 43

135) (5Z,7E,22E) - (1S,3R) -1,3-Bis[[dimethyl (1,1-dimethylethyl)silyl]oxy]-24-oxo-9,10-secocholesta-5,7,10(19),22-tetraene-25-carboxylic acid butylester 180 mg (0.23 mmol) of 113a/113b is reacted analogously to 78) and 100 mg of the title compound is obtained as colorless foam.

¹H-NMR(CDCl₃) : δ=0.04 ppm (s, 12H, SiMe); 0.53 (s, 3H, H-18); 0.89 (s, 18H, Si-t-butyl); 0.90 (t, J=7 Hz, 3H COOBu); 1.06 (d, J=7 Hz, 3H, H-21); 1.36 (s, 6H, C-26 and C-27); 4.08 (t, J=7 Hz, 3H COOBu); 4.18 (m, 1H, H-3); 4.38 (m, 1H, H-1); 4.85 and 5.18 (2x s; 1H, H-19 each); 6.00 and 6.22 (2x d, J=11 Hz; 1H, H-6 and H-7 each); 6.14 (d, J=15 Hz, 1H, H-23); 6.82 (dd, J=15, 9 Hz, 1H, H-22).

136) (5Z,7E,22E) - (1S,3R) -1,3-Dihydroxy-24-oxo-9,10-secocholesta-5,7,10 (19) , 22-tetraene-25-carboxylic acid butyl ester 133

95 mg (0.13 mmol) of 132 is reacted analogously to 73) and 35 mg of the title compound is obtained as colorless foam.

¹H-NMR(CD₂Cl₂) : δ=0.56 ppm (s, 3H, H-18); 0.89 (t, J=7 Hz, 3H, COOBu); 1.08 (d, J=7 Hz, 3H, H-21); 1.32 (3, 6H, C-26 and C-27); 4.08 (tbr, J=7 Hz, 2H, COOBu); 4.17 (m, 1H, H-3); 4.38 (m, 1H, H-1); 4.95 and 5.29 (2x s; 1H, H-19 each); 6.00 and 6.36 (2x d, J=11 Hz; 1H, H-6 and H-7 each); 6.15 (d, J=15 Hz, 1H, H-23 ); 6.80 (dd, J=15, 9 Hz, 1H, H-22).

EXAMPLE 44

137) (5Z,7E,22E) - (1S,3R) -1,3-Bis[[dimethyl(1,1dimethylethyl)silyl]oxy]-24-oxo-9,10-secocholesta-5,7,10(19),22-tetraene-25-carboxylic acid-2-methylpropyl ester 134

205 mg (0.28 mmol) of 116a/116b is reacted analogously to 78) and 120 mg of the title compound is obtained as colorless foam.

¹H-NMR(CDCl₃): δ=0.01 ppm (s, 12H, SiMe); 0.50 (s, 3H, H-18); 0.82 (s, 18H, Si-t-butyl); 0.86 (t, J=7 Hz, 6H COOiBu); 1.04 (d, J=7 Hz, 3H, H-21); 1.32 (s, 6H, C-26 and C-27); 3.87 and 3.90 (2x dd, J=10, 7 Hz; 1H, COOiBu each); 4.14 (m, 1H, H-3); 4.33 (m, 1H, H-1); 4.89 and 5.11 (2x s, 1H, H-19 each); 5.95 and 6.17 (2x d, J=11 Hz; 1H, H-6 and H-7 each); 6.09 (d, J=15 Hz, 1H, H-23); 6.78 (dd, J=15, 9.5 Hz, 1H, H-22).

138) (5Z,7E,22E) - (1S,3R)-1,3-Dihydroxy-24-oxo-9,10-secocholesta-5,7,10 (19),22-tetraene-25-carboxylic acid-2-methylpropyl ester 135

115 mg (0.15 mmol) of 134 is reacted analogously to 73) and 54 mg of the title compound is obtained as colorless foam.

¹H-NMR(CD₂Cl₂): δ=0.56 ppm (s, 3H, H-18); 0.89 (d, J=7 Hz, 6H, COOiBu); 1.08 (d, J=7 Hz, 3H, H-21); 1.34 (3, 6H, C-26 and C-27); 3.84 and 3.89 (2x dd, J=10, 6 Hz; 1H, COOiBu each); 4.17 (m, 1H, H-3); 4.38 (m, 1H, H-1); 4.95 and 5.29 (2x s; 1H, H-19 each); 6.00 and 6.35 (2x d, J=11 Hz; 1H, H-6 and H-7 each); 6.16 (d, J=15 Hz, 1H, H-23); 6.80 (dd, J=15, 9 Hz, 1H, H-22).

EXAMPLE 45

139) (5Z,7E,22E) - (1S,3R) -1,3-Bis[[dimethyl(1,1-dimethylethyl)silyl]oxy]-24-oxo-9,10-secocholesta-5,7,10(19),22-tetraene-25-carboxylic acid pentyl ester 136

190 mg (0.25 mmol) of 119a/119b is reacted analogously to 78) and 108 mg of the title compound is obtained as colorless foam.

¹H-NMR(CDCl₃): δ=0.04 ppm (s, 12H, SiMe); 0.55 (s, 3H, H-18); 0.89 (s, 18H, Si-t-butyl); 0.89 (t, J=7 Hz, 3H COOPent); 1.08 (d, J=7 Hz, 3H, H-21); 1.36 (s, 6H, C-26 and C-27); 4.09 (t, J=7 Hz, 3H COOPent); 4.19 (m, 1H, H-3); 4.38 (m, 1H, H-1); 4.85 and 5.18 (2x s; 1H, H-19 each); 6.01 and 6.22 (2x d, J=11 Hz; 1H, H-6 and H-7 each); 6.14 (d, J=15 Hz, 1H, H-23); 6.83 (dd, J=15, 9.5 Hz, 1H, H-22).

140) (5Z,7E,22E) - (1S,3R) -1,3-Dihydroxy-24-oxo-9,10-secocholesta-5,7,10(19), 22-tetraene-25-carboxylic acid pentyl ester 137

103 mg (0.14 mmol) of 136 is reacted analogously to 73) and 42 mg of the title compound is obtained as colorless foam.

¹H-NMR(CD₂Cl₂): δ=0.56 ppm (s, 3H, H-18); 0.88 (t, J=7 Hz, 3H COOPent); 1.08 (d, J=7 Hz, 3H, H-21); 1.32 (3, 6H, C-26 and C-27); 4.08 (t, J=7 Hz, 2H COOPent); 4.17 (m, 1H, H-3); 4.38 (m, 1H, H-1); 4.95 and 5.30 (2x s; 1H, H-19 each); 6.00 and 6.35 (2x d, J=11 Hz; 1H, H-6 and H-7 each); 6.15 (d, J=15 Hz, 1H, H-23 ); 6.80 (dd, J=15, 9 Hz, H, H-22).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A 25-carboxylic acid compound of formula I,

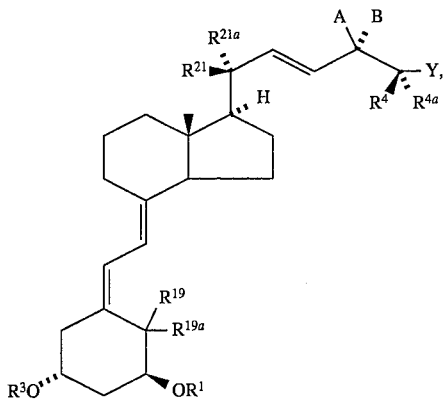

in which
- $R^1$ and $R^3$ independently of one another are each a hydrogen atom, a straight-chain or branched-chain saturated alkanoyl group with 1 to 9 carbon atoms or an aroyl group;
- $R^{19}$ and $R^{19a}$ are each a hydrogen atom or together form an exocyclic methylene group;
- A and B together are a keto oxygen atom or A is a group $OR^{24}$ and B is a hydrogen atom, or A is a hydrogen atom and B is a group $OR^{24}$;
- $R^{24}$ is a hydrogen atom or a straight-chain or branched-chain saturated alkanoyl group with up to 9 carbon atoms or an aroyl group;
- $R^{21}$ and $R^{21a}$ independently of one another are each a hydrogen atom, a chlorine or fluorine atom, an alkyl group with 1 to 4 carbon atoms, together are a methylene group, or together with carbon atom 20 are a 3–7 membered, saturated or unsaturated carbocyclic ring;
- $R^4$ and $R^{4a}$ simultaneously are each a hydrogen atom, chlorine or fluorine atom, a trifluoromethyl group, a straight-chain or branched-chain, saturated or unsaturated hydrocarbon radical with up to 4 carbon atoms, or $R^4$ and $R^{4a}$ together with carbon atom 25 are a 3 to 7 membered, saturated or unsaturated carboxylic ring;
- Y is $-C(O)-NR^5-R^{5'}$, $-C(O)OR^6$, $-C(O)SR^6$, or $-CN$; and
- $R^5$ and $R^{5'}$, independently of one another, are each a hydrogen atom or a linear or branched alkyl group with up to 8 carbon atoms; and
- $R^6$ is a hydrogen atom, a linear or branched alkyl group with up to 8 carbon atoms, an unsaturated, linear or branched hydrocarbon radical with 3 to 8 carbon atoms or

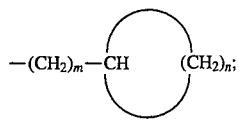

m is 0 or 1; and
n is 2, 3, 4, 5 or 6, and if m is 1 n can also be 1.

2. A compound of formula I according to claim 1 wherein $R^1$, $R^3$ and $R^{24}$ each mean a hydrogen atom.

3. A compound of formula I according to claim 1, wherein $R^1$, $R^3$ and $R^{24}$ each stand for a acetyl, propionyl, n-butyryl, iso-butyryl, pivaloyl or valeryl radical.

4. A compound of formula I according to claim 1, wherein $R^1$, $R^3$ and $R^{24}$ each stand for a benzoyl radical.

5. A compound of formula I according to claim 1, wherein $R^4$ and $R^{4a}$ each stand for methyl, ethyl, n-propyl, n-butyl, i-propyl, i-butyl or tert-butyl radical.

6. A compound of formula I according to claim 1, wherein $R^{21}$ stands for a hydrogen atom and $R^{21a}$ stands for a methyl group.

7. A compound of formula I according to claim 1, wherein substituent $R^{21}$ or $R^{21a}$ stands for a methyl, ethyl, n-propyl, n-butyl, i-propyl, i-butyl or tert-butyl radical and the other substituent for a methyl group.

8. A compound of formula I according to claim 1, wherein $R^{21}$ or $R^{21a}$ together with tertiary carbon atom 20 form a cyclopropyl ring.

9. A compound of formula I according to claim 1, wherein R21 or $R^{21a}$ together stand for a methylene group.

10. A compound of formula I according to claim 1, wherein $R^{21}$ means a fluorine atom and $R^{21a}$ means a methyl group or R21 means a methyl group and $R^{21a}$ means a fluorine atom.

11. A compound of formula I according to claim 1, wherein $R^4$ and $R^{4a}$ each mean a methyl or ethyl group or together with tertiary carbon atom 25 form a cyclopropyl, cyclobutyl, cyclopentyl or cyclohexyl ring.

12. A compound according to claim 1, wherein said compound is:

(5Z,7E,22E)-(1S,3R,24R)-1,3,24-Trihydroxy-9,10-secocholesta-5,7,10(19),22-tetraene-25-carboxylic acid ethyl ester, (5Z,7E,22E) - (1S,3R,24R)-26,27-Dimethyl-1,3,24-trihydroxy-9,10-secocholesta-5,7,10 (19),22-tetraene-25-carboxylic acid methyl ester, (5Z,7E,22E) - (1S,3R,24R) -1,3,24-Trihydroxy-9,10-secocholesta-5,7,10 (19),22-tetraene-25-carboxylic acid-1-methyl ethyl esters, (5Z,7E,22E) - (1S,3R,24R)-1,3,24-Trihydroxy-9,10-secocholesta-5,7,10(19), 22-tetraene-25-carboxylic acid methyl ester, (5Z,7E,22E) - (1S,3R,24S)-1,3,24-Trihydroxy-9,10-secochola-5,7,10(19),22-tetraene-24-acetic acid methyl ester, (5Z,7E,22E) - (1S,3R,24R)-1,3,24-Trihydroxy-9,10-secocholesta-5,7,10(19),22-tetraene-25-carboxylic acid nitrile, (5Z,7E,22E) - (1S,3R,24R)-1,3,24-Trihydroxy-9,10-secocholesta-5,7,10(19),22-tetraene-25-carboxylic acid propyl ester, (5Z,7E,22E) - (1S,3R,24R)-1,3,24-Trihydroxy-9,10-secocholesta-5,7,10(19),22-tetraene-25-carboxylic acid, (5Z,7E,22E) - (1S,3R,24R)-1,3,24-Trihydroxy-26,27-cyclo-9,10-secocholesta-5,7,10(19),22-tetraene-25-carboxylic acid methyl ester, (5Z,7E,22E) - (1S,3R,24R)-1,3,24-Trihydroxy-26,27-cyclo-9,10-secocholesta-5,7,10 (19),22-tetraene-25-carboxylic acid ethyl ester, (5Z,7E,22E) - (1S,3R,24R)-1,3,24-Trihydroxy-26,27-cyclo-9,10-secocholesta-5,7,10(19),22-tetraene-25-carboxylic acid propyl ester, (5Z,7E,22E) - (1S,3R,24R)-1,3,24-Trihydroxy-26,27-cyclo-9,10-secocholesta-5,7,10(19),22-tetraene-25-carboxylic acid butyl ester, (5Z,7E,22E) - (1S,3R,24R)-1,3,24-Trihydroxy-26,27-cyclo-9,10-secocholesta-5,7,10(19),22-tetraene-25-carboxylic acid-2methyl propyl ester, (5Z,7E,22E) - (1S,3R,24R)-1,3,24-Trihydroxy-26,27-cyclo-9,10-secocholesta-5,7,10(19),22-tetraene-25-carboxylic acid pentyl ester, (5Z,7E,22E) - (1S,3R,24R)-1,3,24-Trihydroxy-26,27-cyclo-9,10-secocholesta-5,7,10(19),22-tetraene-25-carboxylic acid hexyl ester, (5Z,7E,22E) - (1S,3R,24R)-1,3,24-Trihydroxy-9,10-secocholesta-5,7,10(19),22-tetraene-25-carboxylic acid dimethyl amide, (5Z,7E,22E) - (1S,3R,24R)-1,3,24-Trihydroxy-9,10-secocholesta-5,7,10 (19), 22 -tetraene-25 -carboxylic acid diethyl amide, (5Z,7E,22E) - (1S,3R,24R)-1,3,24-Trihydroxy-26,27-cyclo-9,10-secocholesta-5,7,10(19),22-tetraene-25-carboxylic acid diethyl amide, (5Z,7E,22E) - (1S,3R)-1,3-Dihydroxy-24-oxo-26,27-cyclo-9,10-secocholesta-5,7,10(19),22-tetraene-25-carboxylic acid-n-butylamide, (5Z,7E,22E) - (1S,3R,24R)-20-Methyl-1,3,24-trihydroxy-9,10-secocholesta-5,7,10(19),22-tetraene-25-carboxylic acid methyl ester, (5Z,7E,22E) - (1S,3R,24S)-20-Methyl-1,3,24-trihydroxy-9,10-secocholesta-5,7,10(19),22-tetraene-25-carboxylic acid methyl ester, (5Z,7E,22E) - (1S,3R,24R)-20-Methyl-1,3,24-trihydroxy-9,10-secocholesta-5,7,10(19),22-tetraene-25-carboxylic acid ethyl ester, (5Z,7E,22E) - (1S,3R,24S)-20-Methyl-1,3,24-trihydroxy-9,10-secocholesta-5,7,10(19),22-tetraene-25-carboxylic acid ethyl ester, (5Z,7E,22E) - (1S,3R,24R)-20-Methyl-1,3,24-trihydroxy-9,10-secocholesta-5,7,10(19),22-tetraene-25-carboxylic acid propyl ester, (5Z,7E,22E) - (1S,3R,24S)-20-Methyl-1,3,24-trihydroxy-9,10-secocholesta-5,7,10(19 ),22 -tetraene-25 -carboxylic acid propyl ester, (5Z,7E,22E) - (1S,3R,24R)-20-Methyl-1,3,24-trihydroxy-9,10-secocholesta-5,7,10(19),22-tetraene-25-carboxylic acid-1-methyl ethyl ester, (5Z,7E,22E) - (1S,3R,24S)-20-Methyl-1,3,24-trihydroxy-9,10-secocholesta-5,7,10(19),22-tetraene-25-carboxylic acid-1-methyl ethyl esters, (5Z,7E,22E) - (1S,3R,24R)-20-Methyl-1,3,24-trihydroxy-9,10-secocholesta-5,7,10(19),22-tetraene-25-carboxylic acid butyl ester, (5Z,7E,22E) - (1S,3R,24S)-20-Methyl-1,3,24-trihydroxy-9,10-secocholesta-5,7,10(19),22-tetraene-25-carboxylic acid butyl ester, (5Z,7E,22E) - (1S,3R,24R)-1,3,24-Trihydroxy-9,10-secocholesta-5,7,10(19),20,22-pentaene-25-carboxyllc acid methyl ester, (5Z,7E,22E) - (1S,3R,24S)-1,3,24-Trihydroxy-9,10-secocholesta-5,7,10(19),20,22-pentaene-25-carboxyllc acid methyl ester, (5Z,7E,22E) - (1S,3R,24R)-1,3,24-Trihydroxy-9,10-secocholesta-5,7,10(19),20,22-pentaene-25-carboxylic acid ethyl ester, (5Z,7E,22E) - (1S,3R,24R)-1,3,24-Trihydroxy-9,10-secocholesta-5,7,10(19),20,22-pentaene-25-carboxylic acid ethyl esters, (5Z,7E,22E) - (1S,3R,24R)-1,3,24-Trihydroxy-9,10-secocholesta-5,7,10(19),20,22-pentaene-25-carboxylic acid propyl esters, (5Z,7E,22E) - (1S,3R,24S)-1,3,24-Trihydroxy-9,10-secocholesta-5,7,10(19),20,22-pentaene-25-carboxyllc acid propyl esters, (5Z,7E,22E) - (1S,3R,24R)-1,3,24-Trihydroxy-9,10-secocholesta-5,7,10(19),20,22-pentaene-25-carboxylic acid-1-methyl ethyl ester, (5Z,7E,22E) - (1S,3R,24S)-1,3,24-Trihydroxy-9,10-secocholesta-5,7,10(19),20,22-pentaene-25-carboxyllc acid-1-methyl ethyl ester, (5Z,7E,22E) - (1S,3R,24R)-1,3,24-Trihydroxy-9,10-secocholesta-5,7,10(19),20,22 -pentaene-25-carboxylic acid butyl ester, (5Z,7E,22E) - (1S,3R,24S)-1,3,24-Trihydroxy-9,10-secocholesta-5,7,10(19),20,22-pentaene-25-carboxylic acid butyl ester, (5Z,7E,22E) - (1S,3R,24R)-20,21-Methylene-1,3,24-trihydroxy-9,10-secocholesta-5,7,10(19),22-tetraene-25-carboxylic acid methyl ester, (5Z,7E,22E) - (1S,3R,24S)-20,21-Methylene-1,3,24-trihydroxy-9,10-secocholesta-5,7,10(19),22-tetraene-25-carboxyllc acid methyl ester, (5Z,7E,22E) - (1S,3R,24R)-20,21-Methylene-1,3,24-trihydroxy-9,10-secocholesta-5,7,10(19),22-tetraene-25-carboxylic acid ethyl ester, (5Z,7E,22E) - (1S,3R,24S)-20,21-Methylene-1,3,24-trihydroxy-9,10-secocholesta-5,7,10(19),22-tetraene-25-carboxylic acid ethyl ester, (5Z,7E,22E) - (1S,3R,24R)-20,21-Methylene-1,3,24-trihydroxy-9,10-secocholesta-5,7,10(19),22-tetraene-25-carboxylic acid propyl ester, (5Z,7E,22E) - (1S,3R,24S)-20,21-Methylene-1,3,24-trihydroxy-9,10-secocholesta-5,7,10(19),22-tetraene-25-carboxylic acid propyl ester, (5Z,7E,22E) - (1S,3R,24R)-20,21-Methylene-1,3,24-trihydroxy-9,10-secocholesta-5,7,10(19),22-tetraene-25-carboxylic acid-1methyl ethyl ester, (5Z,7E,22E) - (1S,3R,24S)-20,21-Methylene-1,3,24-trihydroxy-9,10-secocholesta-5,7,10(19),22-tetraene-25-carboxylic acid-1methyl ethyl ester, (5Z,7E,22E) - (1S,3R,24R)-20,21-Methylene-1,3,24-trihydroxy-9,10-secocholesta-5,7,10(19),22-tetraene-25-carboxylic acid butyl ester, (5Z,7E,22E) - (1S,3R,24S)-20,21-Methylene1,3,24-trihydroxy9,10-secocholesta-5,7,10(19),22-tetraene-25-carboxylic acid butyl ester, (7E,22E) - (1R,3R,24R)-1,3,24-Trihydroxy-19-nor-9,10-secocholesta-5,7,22-triene-25-carboxylic acid methyl ester, (7E,22E) - (1R,3R,24S)-1,3,24-Trihydroxy-19-nor-9,10-secocholesta-5,7,22-triene-25-carboxylic acid methyl ester, (7E,22E) - (1R,3R,24R)-1,3,24-Trihydroxy-19-nor-9,10-secocholesta-5,7,2 2-triene-25-carboxylic acid ethyl ester, (7E,22E) - (1R,3R,24S)-1,3,24-Trihydroxy-19-nor-9,10-secocholesta-5,7,2 2-triene-25-carboxylic acid ethyl ester, (7E,22E) - (1R,3R,24R)-1,3,24-Trihydroxy-19-nor-9,10-secocholesta-5,7,2 2-triene-25-carboxylic acid propyl ester, (7E,22E) - (1R,3R,24S)-1,3,24-Trihydroxy-19-nor-9,10-secocholesta-5,7,2 2-triene-25-carboxylic acid propyl ester, (7E,22E) - (1R,3R,24R)-1,3,24-Trihydroxy-19-nor-9,10-secocholesta-5,7,2 2-triene-25-carboxylic acid-1-methyl ethyl ester, (7E,22E) - (1R,3R,24S)-1,3,24-Trihydroxy-19-nor-9,10-secocholesta-5,7,22-triene-25-carboxylic acid-1-methyl ethyl ester, (7E,22E) - (1R,3R,24R)-1,3,24-Trihydroxy-19-nor-9,10-secocholesta-5,7,22-triene-25-carboxylic acid butyl ester, (7E,22E) - (1R,3R,24S)-1,3,24-Trihydroxy-19-nor-9,10-secocholesta-5,7,2 2-triene-25-carboxylic acid butyl ester, (7E,22E) - (1R,3R,24R)-1,3,24-Trihydroxy-19-nor-9,10-secocholesta-5,7,20,22-tetraene-25-carboxylic acid methyl ester, (7E,22E)-(1R,3R,24S)-1,3,24-Trihydroxy-19-nor-9,10-secocholesta-5,7,20,22-tetraene-25-carboxylic acid methyl ester, (7E,22E)-(1R,3R,24R)-1,3,24-Trihydroxy-19-nor-9,10-secocholesta-5,7,20,22-tetraene-25-carboxylic acid ethyl ester, (7E,22E)-(1R,3R,24S)-1,3,24-Trihydroxy-19-nor-9,10-secocholesta-5,7,20,22-tetraene-25-carboxylic acid ethyl ester, (7E,22E)-(1R,3R,24R)-1,3,24-Trihydroxy-19-nor-9,10-secocholesta-5,7,20,22-tetraene-25-carboxylic acid propyl ester, (7E,22E)-(1R,3R,24S)-1,3,24-Trihydroxy-19-nor-9,10-secocholesta-5,7,20,22-tetraene-25-carboxylic acid propyl ester, (7E,22E)-(1R,3R,24R)-1,3,24-Trihydroxy-19-nor-9,10-secocholesta-5,7,20,22-tetraene-25-carboxylic acid-1-methyl ethyl ester, (7E,22E) - (1R,3R,24S)-1,3,24-Trihydroxy-19-nor-9,10-secocholesta-5,7,20,22-tetraene-25-carboxylic acid-1-methyl ethyl ester, (7E,22E) - (1R,3R,24R)-1,3,24-Trihydroxy-19-nor-9,10-secocholesta-5,7,20,22-tetraene-25-carboxylic acid butyl ester, (7E,22E) - (1R,3R,24S)-1,3,24-Trihydroxy-19-nor-9,10-secocholesta-5,7,20,22-tetraene-25-carboxylic acid butyl ester, (7E,22E) - (1R,3R)-1,3-Dihydroxy-24-oxo-19-nor-9,10-secocholesta-5,7,2 2-triene-25-carboxylic acid methyl ester, (7E,22E) - (1R,3R)-1,3-Dihydroxy-24-oxo-19-nor-9,10-secocholesta-5,7,2 2-triene-25-carboxylic acid ethyl ester, (7E,22E) - (1R,3R)-1,3-Dihydroxy-24-oxo-19-nor-9,10-secocholesta-5,7,2 2-triene-25-carboxylic acid propyl ester, (7E,22E) - (1R,3R)-1,3-Dihydroxy-24-oxo-19-nor-9,10-secocholesta-5,7,2 2-triene-25-carboxylic acid-1-methyl ethyl ester, (7E,22E) - (1R,3R)-1,3-Dihydroxy-24-oxo-19-nor-9,10-secocholesta-5,7,22-triene-25-carboxylic acid butyl ester, (7E,22E) - (1R,3R)-1,3-Dihydroxy-24-oxo-19-nor-9,10-secocholesta-5,7,20,22-tetraene-25-carboxylic acid methyl ester, (7E,22E) - (1R,3R)-1,3-Dihydroxy-24-oxo-19-nor-9,10-secocholesta-5,7,20,22-tetraene-25-carboxylic acid ethyl ester, (7E,22E) - (1R,3R)-1,3-Dihydroxy-24-oxo-19-nor-9,10-secocholesta-5,7,20,22-tetraene-25-carboxylic acid propyl ester, (7E,22E) - (1R,3R)-1,3-Dihydroxy-24-oxo-19-nor-9,10-secocholesta-5,7,20,22-tetraene-25-carboxylic acid-1-methyl ethyl ester, (7E,22E) - (1R,3R)-1,3-Dihydroxy-24-oxo-19-nor-9,10-secocholesta-5,7,20,22-tetraene-25-carboxylic acid butyl ester, (7E,22E) - (1R,3R,20S,24R)-20-Fluoro-1,3,24-trihydroxy-19-nor-9,10-secocholesta-5,7,22-triene-25-carboxylic acid ethyl ester, (7E,22E) - (1R,3R,20S,24S)-20-Fluoro-1,3,24-trihydroxy-19-nor-9,10-secocholesta-5,7,22-triene-25-carboxylic acid ethyl ester, (7E,22E) - (1R,3R,20R,24R)-20-Fluoro-1,3,24-trihydroxy-19-nor-9,10-secocholesta-5,7,22-triene-25-carboxyllc acid ethyl ester, (7E,22E) - (1R,3R,20R,24S)-20-Fluoro-1,3,24-trihydroxy-19-nor-9,10-secocholesta-5,7,22-triene-25-carboxylic acid ethyl ester, (7E,22E) - (1R,3R,20S,24R)-20-Fluoro-1,3,24-trihydroxy-19-nor-9,10-secocholesta-5,7,22-triene-25-carboxylic acid-1-methyl ethyl ester, (7E,22E) - (1R,3R,20S,24S)-20-Fluoro-1,3,24-trihydroxy-19-nor-9,10-secocholesta-5,7,22-triene-25-carboxylic acid-1-methyl ethyl ester, (7E,22E) - (1R,3R,20R,24R)-20-Fluoro-1,3,24-trihydroxy-19-nor-9,10-secocholesta-5,7,22-triene-25-carboxylic acid-1-methyl ethyl ester, (7E,22E) - (1R,3R,20R,24S)-20-Fluoro-1,3,24-trihydroxy-19-nor-9,10-secocholesta-5,7,22-triene-25-carboxylic acid ethyl-1methyl ester, (5Z,7E,22E) - (1S,3R,24R)-1,3,24-Trihydroxy-9,10-secocholesta-5,7,10(19),22-tetraene-25-carboxylic acid butyl ester, (5Z,7E,22E) - (1S,3R,24S)-1,3,24-Trihydroxy-9,10-secocholesta-5,7,10(19),22-tetraene-25-carboxylic acid butyl ester, (5Z,7E,22E) - (1S,3R,24R)-1,3,24-Trihydroxy-9,10-secocholesta-5,7,10(19),22-tetraene-25-carboxylic acid-2-methyl propyl ester, (5Z,7E,22E) - (1S,3R,24S)-1,3,24-Trihydroxy-9,10-secocholesta-5,7,10(19),22-tetraene-25-carboxylic acid-2-methyl propyl ester, (5Z,7E,22E) - (1S,3R,24R)-1,3,24-Trihydroxy-9,10-secocholesta-5,7,10(19),22-tetraene-25-carboxylic acid pentyl ester, (5Z,7E,22E) - (1S,3R,24S)-1,3,24-Trihydroxy-9,10-secocholesta-5,7,10(19),22-tetraene-25-carboxylic acid pentyl ester, (5Z,7E,22E) - (1S,3R)-1,3-Dihydroxy-24-oxo-9,10-secocholesta-5,7,10(19),22-tetraene-25-carboxylic acid methyl ester, (5Z,7E,22E) - (1S,3R)-1,3-Dihydroxy-24-oxo-9,10-secocholesta-5,7,10(19),22-tetraene-25-carboxylic acid ethyl ester, (5Z,7E,22E) - (1S,3R)-1,3-Dihydroxy-24-oxo-9,10-secocholesta-5,7,10(19),22 -tetraene-25 -carboxylic acid propyl ester, (5Z,7E,22E) - (1S,3R)-1,3-Dihydroxy-24-oxo-9,10-secocholesta-5,7,10(19),22-tetraene-25-carboxylic acid-1-methyl ethyl ester, (5Z,7E,22E) - (1S,3R)-1,3-Dihydroxy-24-oxo-9,10-secocholesta-5,7,10(19),22-tetraene-25-carboxylic acid butyl ester, (5Z,7E,22E) - (1S,3R)-1,3-Dihydroxy-24-oxo-9,10-secocholesta-5,7,10(19),22-tetraene-25-carboxylic acid-2-methyl propyl ester, (5Z,7E,22E) - (1S,3R)-1,3-Dihydroxy-24-oxo-9,10-secocholesta-5,7,10(19),22-tetraene-25-carboxylic acid pentyl ester, (5Z,7E,22E) - (1S,3R)-1,3-Dihydroxy-20-methyl-24-oxo-9,10-secocholesta-5,7,10(19),22-tetraene-25-carboxylic acid ethyl ester, (5Z,7E,22E) - (1S,3R)-1,3-Dihydroxy-20-methyl-24-oxo-9,10-secocholesta-5,7,10(19),22-tetraene-25-carboxyllc acid-1-methyl ethyl ester, (5Z,7E, 22 E) - (1S,3R,24R)-1,3,24-Trihydroxy-26a,27-cyclo-26a-homo-9,10-secocholesta-5,7,10(19),22-tetraene-25-carboxylic acid ethyl ester, (5Z,7E, 22 E) - (1S,3R,24S)-1,3,24-Trihydroxy-26a,27-cyclo-26a-homo-9,10- secocholesta-5,7,10(19),22-tetraene-25-carboxylic acid ethyl ester, (5Z,7E, 22 E) - (1S,3R,24R)-1,3,24-Trihydroxy-26a,27-cyclo-26a-homo-9,10-secocholesta-5,7,10(19),22-tetraene-25-carboxylic-1-methyl ethyl ester, or (5Z,7E,22E) - (1S,3R,24S)-1,3,24-Trihydroxy-26a,27-cyclo-a-homo-9,10-secocholesta-5,7,10(19),22-tetraene-25-carboxylic-1-methyl ethyl ester.

13. A compound of formula I according to claim 1, wherein $R^{19}$ and $R^{19a}$ each stand for a hydrogen atom.

14. A compound of claim 13, wherein $R^{21}$ stands for a hydrogen atom and $R^{21a}$ stands for a methyl group.

15. A compound of claim 13, wherein $R^{21}$ and $R^{21a}$ together stand for a methylene group.

16. A compound of claim 13, wherein $R^{21}$ and $R^{21a}$ each stand for a methyl group.

17. A compound of claim 13, wherein $R^{21}$ stands for a hydrogen atom and $R^{21a}$ stands for a fluorine atom or vice versa.

18. A compound of formula I according to claim 1, wherein $R^{19}$ and $R^{21a}$ together stand for a methylene group.

19. A compound of claim 18, wherein $R^{21}$ stands for a hydrogen atom and $R^{21a}$ stands for a methyl group.

20. A compound of claim 18, wherein $R^{21}$ and $R^{21a}$ together stand for a methylene group.

21. A compound of claim 18, wherein $R^{21}$ and $R^{21a}$ each stand for a methyl group.

22. A compound of formula I according to claim 1, wherein at least, one of $R^5$, $R^{5'}$ and $R^6$ a methyl, ethyl, n-propyl, n-butyl, i-propyl, i-butyl or tert.-butyl group.

23. A compound according to claim 1, wherein $R^5$ is methyl, ethyl, n-propyl, n-butyl, i-propyl, i-butyl or tert-butyl;

$R^{5'}$ is methyl, ethyl, n-propyl, n-butyl, i-propyl, i-butyl or tert-butyl; and $R^6$ is methyl, ethyl, n-propyl, n-butyl, i-propyl, i-butyl or tert-butyl.

24. A pharmaceutical composition comprising at least one compound according to claim 1 and a pharmaceutically compatible vehicle.

25. A composition according to claim 24, wherein said composition contains 0.1–1,000 μg.

26. A composition according to claim 24, wherein said composition contains 1–500 μg.

* * * * *